(12) United States Patent
Pestell

(10) Patent No.: US 10,952,415 B2
(45) Date of Patent: Mar. 23, 2021

(54) PROSTATE CANCER CELL LINES, GENE SIGNATURES AND USES THEREOF

(75) Inventor: Richard G. Pestell, Philadelphia, PA (US)

(73) Assignee: Richard G. Pestell, Philadelphia, PA (US)

(*) Notice: Subject to any disclaimer, the term of this patent is extended or adjusted under 35 U.S.C. 154(b) by 0 days.

(21) Appl. No.: 14/003,384

(22) PCT Filed: Mar. 9, 2012

(86) PCT No.: PCT/US2012/028546
§ 371 (c)(1),
(2), (4) Date: Nov. 19, 2013

(87) PCT Pub. No.: WO2012/122499
PCT Pub. Date: Sep. 13, 2012

(65) Prior Publication Data
US 2014/0109245 A1   Apr. 17, 2014

Related U.S. Application Data

(60) Provisional application No. 61/450,767, filed on Mar. 9, 2011.

(51) Int. Cl.
| | | |
|---|---|---|
| *A61K 31/46* | (2006.01) | |
| *A01K 67/027* | (2006.01) | |
| *C12N 5/09* | (2010.01) | |
| *A61K 31/506* | (2006.01) | |
| *C12Q 1/6886* | (2018.01) | |
| *G01N 33/574* | (2006.01) | |

(52) U.S. Cl.
CPC .......... *A01K 67/0275* (2013.01); *A61K 31/46* (2013.01); *A61K 31/506* (2013.01); *C12N 5/0693* (2013.01); *C12Q 1/6886* (2013.01); *G01N 33/574* (2013.01)

(58) Field of Classification Search
CPC ............................ A01K 67/0275; A01K 31/46
USPC ......................................................... 435/7.23
See application file for complete search history.

(56) References Cited

U.S. PATENT DOCUMENTS

| | | |
|---|---|---|
| 5,587,458 A | 12/1996 | King et al. |
| 5,877,305 A | 3/1999 | Huston et al. |
| 6,586,430 B1 | 7/2003 | Armour et al. |
| 6,596,746 B1 | 7/2003 | Das et al. |
| 6,667,314 B2 | 12/2003 | Perros et al. |
| 6,689,765 B2 | 2/2004 | Baroudy et al. |
| 7,384,944 B2 | 6/2008 | Baroudy |
| 7,872,027 B2 | 1/2011 | Metallo et al. |
| 2002/0048786 A1 | 4/2002 | Rosen et al. |
| 2002/0182624 A1 | 12/2002 | Zlotnik |
| 2004/0151719 A1 | 8/2004 | Li et al. |
| 2006/0251651 A1 | 11/2006 | Shibayama et al. |
| 2007/0270429 A1 | 11/2007 | Shibayama et al. |
| 2009/0118175 A1 | 5/2009 | Macina |
| 2009/0131403 A1 | 5/2009 | Kusuda et al. |
| 2010/0184046 A1 | 7/2010 | Klass et al. |

FOREIGN PATENT DOCUMENTS

| | | |
|---|---|---|
| JP | 2005124588 A | 5/2005 |
| JP | 2009512705 A | 3/2009 |
| WO | 9519970 A1 | 7/1995 |
| WO | 9610028 A1 | 4/1996 |
| WO | 9713760 A1 | 4/1997 |
| WO | 9716452 A1 | 5/1997 |
| WO | 9728161 A1 | 8/1997 |
| WO | 9732879 A1 | 9/1997 |
| WO | 9749706 A1 | 12/1997 |
| WO | 9802434 A1 | 1/1998 |
| WO | 9802437 A1 | 1/1998 |
| WO | 9935132 A1 | 7/1999 |
| WO | 9935146 A1 | 7/1999 |
| WO | 0062778 A1 | 10/2000 |
| WO | 200206771 A3 | 9/2002 |
| WO | 0281449 A1 | 10/2002 |
| WO | 06067584 A1 | 6/2006 |

(Continued)

OTHER PUBLICATIONS

Gil et al., Cancer Res., 65(6): 2179-2185, 2005.*
Fatkenheuer et al (Nat Med, 2005, 11(11): 1170-1172).*
Milenic et al (MAbs, 2010, 2(5): 550-560).*
Benjamin et al (Am Fam Phys, 2002, 65(9): 1834-1840).*
Thirkill TL, Lowe K, Vedagiri H, Blankenship TN, Barakat AI, Douglas GC. Macaque trophoblast migration is regulated by RANTES. Exp Cell Res 2005; 305: 355-64.
Abel S, van der Ryst E, Rosario MC, Ridgway CE, Medhurst CG, Taylor-Worth RJ, et al. Assessment of the pharmacokinetics, safety and tolerability of maraviroc, a novel CCR5 antagonist, in healthy volunteers. Br J Clin Pharmacol 2008; 65 Suppl 1: 5-18.
Vaday GG, Peehl DM, Kadam PA, Lawrence DM. Expression of CCL5 (RANTES) and CCR5 in prostate cancer. Prostate 2006; 66: 124-34.

(Continued)

*Primary Examiner* — Sean E Aeder
(74) *Attorney, Agent, or Firm* — Seed IP Law Group LLP

(57) ABSTRACT

The present disclosure, in part, is directed to a mammalian prostate cancer cell line comprising at least one or a set of primary mammalian epithelial cells which have been infected with a retroviral vector carrying an oncogene selected from the group consisting of c-Myc, Ha-Ras, NeuT, c-Src and combinations thereof and in which said gene is expressed. Applications of the pro-state cell lines, including immune competent animal models of prostate cancer, a method for the in vitro production of immortalized primary mammalian epithelial cells, a method of determining whether a human subject having prostate cancer is suffering from or at risk for developing metastasis, a method of preventing cancer or inhibiting metastasis of cancer susceptible to treatment in a subject at risk for developing cancer or metastasis of cancer, and method of identifying a candidate compound that selectively interferes with proliferation or viability of a cancer cell that has elevated levels of CCR5 and/or of at least one of its ligands.

7 Claims, 28 Drawing Sheets

(56) References Cited

FOREIGN PATENT DOCUMENTS

| WO | 2006067584 A1 | 6/2006 |
| WO | 2009101533 A1 | 8/2009 |
| WO | 12122499 A2 | 9/2012 |
| WO | 2012122499 A2 | 9/2012 |

OTHER PUBLICATIONS

Perret GY, Crepin M. New pharmacological strategies against metastatic spread. Fundam Clin Pharmacol 2008; 22: 465-92.

Sugasawa H, Ichikura T, Tsujimoto H, Kinoshita M, Morita D, Ono S, et al. Prognostic significance of expression of CCL5/RANTES receptors in patients with gastric cancer. J Surg Oncol 2008; 97: 445-50.

Thompson, I.M., et al. ("Prevalence of prostate cancer among men with a prostate-specific antigen level < or = 4.0 ng per milliliter," New England Journal of Medicine 2004, 350(22), 2239-2246.

Smith, D.S., et al. ("The early detection of prostatecarcinoma with prostate specific antigen: The Washington University experience," Cancer 1997, 80(9), 1853-1856.

Scher, H. I., et al., J Clin Oncol 2005, 23, 8253-8261.

Schindler, T., et al. In Molecular Cell, 1999 (3), 639, 647.

Hamby, J., et al., J. Med. Chem. 40, 1997, 2296-2303.

Panek, R. L., et al., J. Pharmacal. Exp. Ther. 283, 1997, 1433-1444.

Klutchko, S.R., et al., J. Med. Chem. 41, 1998, 3276-3292.

Gamse, R., et al.—J. Bone Miner. Res. 14 (Suppl 1) 1999, S487.

Zhang, X., et al., 'Anibamine, a natural product CCR5 antagonist, as a novel lead for the development of anti-prostate cancer agents', Bioorganic & Medicinal Chemistry Letters, 2010, vol. 20, pp. 4627-4630.

Chidiac C., et al., "Maraviroc: resultats des etudes cliniques", Medecine Et Maladies Infectieuses, Societe Francaise D'Editions Medicales, Paris, FR, val. 38, Mar. 1, 2008, pp. 17-23.

Tsibris, Athe M. N., et al., "Lymphoma Diagnosis and Plasma Epstein-Barr Virus Load during Vicriviroc Therapy: Results of the AIDS Clinical Trials Group A5211 ", Clinical Infectious Diseases, val. 48, No. 5, Mar. 1, 2009 (Mar. 1, 2009 ), pp. 642-649.

Bland, Kirby I., et al., "Oncogene Protein Co-Expression Value of Haras, c-myc, c-fos, and p53 as Prognostic Discriminants for Breast Carcinoma", Annals of Surgery, val. 221, No. 6, Jun. 1, 1995 (Jun. 1, 1995 ), pp. 706-720.

Potter, et al. "Systemic chemokine Levels in Breast Cancer Patients and their Relationship with Circulating Menstrual Hormones," Breast Cancer Res Treat 115, 2009, pp. 279-287.

Pestell, The Role of Cyclin D1 and Androgen Receptor (AR) Mutations in Prostate Cancer. Thomas Jefferson University, Annual Progress Report: 2005 Formula Grant [online]. 2009, pp. 29-39, especially p. 31 to 32; [retrieved on Aug. 27, 2012) Jan. 6, 2018 Retrieved from the internet: <URL : http://lwebserver.health.state. pa.us/pdf/cure/2008-2009/thomas jefferson university/2005f grant ann prg rep sfy08 thorn jeff.pdf.

Watson et al. Context-Dependent Hormone-Refractory Progression Revealed through Characterization of a Novel Murine Prostate Cancer Cell Line. Cancer Res., 2005, vol. 65, Iss 24, pp. 11565-11571; abstract; p. 11565, col. 2, para 3-4; p. 11566, col. 1, para 5; col. 2, para 3.

Gil et al. Immortalization of Primary Human Prostate Epithelial Cells by c-Myc. Cancer Res., 2005, vol. 65, Iss 6, pp. 2179-2185; entire document.

Nagy et al. Overexpression of CD24, c-myc and Phospholipase 2A in Prostate Cancer Tissue Samples Obtained by Needle Biopsy. Pathol. Oncol. Res., 2008, vol. 15, pp. 279-283; entire document.

International Searching Authority, PCT Office of USPTO, PCT International Search Report regarding corresponding PCT Application No. PCT/US2012/028546 dated Sep. 14, 2012, pp. 1-6.

Jemal, A., et al., Cancer statistics, 2003. CA Cancer J Clin, 2003. 53(1): p. 5-26.

Singh, D., et al., Gene expression correlates of clinical prostate cancer behavior. Cancer Cell, 2002. 1(2): p. 203-9.

Lapointe, J., et al., Gene expression profiling identifies clinically relevant subtypes of prostate cancer. Proc Natl Acad Sci USA, 2004. 101(3): p. 811-6.

Kattan, M.W., T.M. Wheeler, and P.T. Scardino, Postoperative nomogram for disease recurrence after radical prostatectomy for prostate cancer. J Clin Oncol, 1999. 17(5): p. 1499-507.

Kattan, M.W., et al., A preoperative nomogram for disease recurrence following radical prostatectomy for prostate cancer. J Natl Cancer Inst, 1998. 90(10): p. 766-71.

Graefen, M., et al., Early prostate-specific antigen relapse after radical retropubic prostatectomy: prediction on the basis of preoperative and postoperative tumor characteristics. Eur Urol, 1999. 36(1): p. 21-30.

Dhanasekaran, S.M., et al., Delineation of prognostic biomarkers in prostate cancer. Nature, 2001. 412(6849): p. 822-6.

Varambally, S., et al., The polycomb group protein EZH2 is involved in progression of prostate cancer. Nature, 2002. 419(6907): p. 624-9.

Henshall, S.M., et al., Survival analysis of genome-wide gene expression profiles of prostate cancers identifies new prognostic targets of disease relapse. Cancer Res, 2003. 63(14): p. 4196-203.

LaTulippe, E., et al., Comprehensive gene expression analysis of prostate cancer reveals distinct transcriptional programs associated with metastatic disease. Cancer Res, 2002. 62(15): p. 4499-506.

Glinsky, G.V., et al., Gene expression profiling predicts clinical outcome of prostate cancer. J Clin Invest, 2004. 113(6): p. 913-23.

Jenkins, R.B., et al., Detection of c-Myc oncogene amplification and chromosomal anomloies in metastatic prostatic carcinoma by fluorescence in situ hybridization. Cancer Res., 1997. 57(3): p. 524-31.

Qian, J., R.B. Jenkins, and D.G. Bostwick, Detection of chromosomal anomalies and c-myc gene amplification in the cribriform pattern of prostatic intraepithelial neoplasia and carcinoma by fluorescence in situ hybridization. Mod Pathol, 1997. 10(11): p. 1113-9.

Ellwood-Yen, K., et al., Myc-driven murine prostate cancer shares molecular features with human prostate tumors. Cancer Cell, 2003. 4(3): p. 223-38.

Creighton, C.J., Multiple oncogenic pathway signatures show coordinate expression patterns in human prostate tumors. PLoS One, 2008. 3(3): p. e1816.

Gumerlock, P.H., et al., Activated ras alleles in human carcinoma of the prostate are rare. Cancer Res, 1991. 51(6): p. 1632-7.

Carter, B.S., J.I. Epstein, and W.B. Isaacs, ras gene mutations in human prostate cancer. Cancer Res, 1990. 50(21): p. 6830-2.

Uzgare, A.R., P.J. Kaplan, and N.M. Greenberg, Differential expression and/or activation of P38MAPK, erkl/2, and jnk during the initiation and progression of prostate cancer. Prostate, 2003. 55(2): p. 128-39.

Le Page, C., et al., Expression and localisation of Akt-1, Akt-2 and Akt-3 correlate with clinical outcome of prostate cancer patients. Br J Cancer, 2006. 94(12): p. 1906-12.

Taylor, B.S., et al., Integrative genomic profiling of human prostate cancer. Cancer Cell, 2010. 18(1): p. 11-22.

Weber, M.J. and D. Gioeli, Ras signaling in prostate cancer progression. J Cell Biochem, 2004. 91(1): p. 13-25.

Ware, J.L., et al., Differential reactivity with anti-c-erbB-2 antiserum among human malignant and benighn prostatic tissue [abstract]. Proc Am Assoc Cancer Res, 1989. 30: p. 1737.

Hughes, C., et al., Molecular pathology of prostate cancer. J Clin Pathol, 2005. 58(7): p. 673-84.

Paronetto, M.P., et al., Expression of a truncated form of the c-Kit tyrosine kinase receptor and activation of Src kinase in human prostatic cancer. Am J Pathol, 2004. 164(4): p. 1243-51.

Bull, J.H., et al., Identification of potential diagnostic markers of prostate cancer and prostatic intraepithelial neoplasia using cDNA microarray. Br J Cancer, 2001. 84(11): p. 1512-9.

Cohen, S. and B.S. Rabin, Psychologic stress, immunity, and cancer. J Natl Cancer Inst, 1998. 90(1): p. 3-4.

Lawson, D.A., et al., Isolation and functional characterization of murine prostate stem cells. Proc Natl Acad Sci USA, 2007. 104(1): p. 181-6.

Huang, E.S., et al., Gene expression phenotypes of oncogenic signaling pathways. Cell Cycle, 2003. 2(5): p. 415-7.

(56) References Cited

OTHER PUBLICATIONS

Catalona, W.J., et al., Selection of optimal prostate specific antigen cutoffs for early detection of prostate cancer: receiver operating characteristic curves. J Urol, 1994. 152(6 Pt 1): p. 2037-42.
Thompson, I.M., et al., Effect of finasteride on the sensitivity of PSA for detecting prostate cancer. J Natl Cancer Inst, 2006. 98(16): p. 1128-33.
Akimoto, S., et al., Relationship between prostate-specific antigen, clinical stage, and degree of bone metastasis in patients with prostate cancer: comparison with prostatic acid phosphatase and alkaline phosphatase. Int J Urol, 1997. 4(6): p. 572-5.
Hanley, J.A. and B.J. McNeil, The meaning and use of the area under a receiver operating characteristic (ROC) curve. Radiology, 1982. 143(1): p. 29-36.
Sharma, A., et al., Novel functions of the retinoblastoma tumor suppressor in controlling lethal tumor phenotypes. (In Press). J Clin Invest, 2010: p. (In Press).
Neve, R.M., et al., A collection of breast cancer cell lines for the study of functionally distinct cancer subtypes. Cancer Cell, 2006. 10(6): p. 515-27.
Chin, K., et al., Genomic and transcriptional aberrations linked to breast cancer pathophysiologies. Cancer Cell, 2006. 10(6): p. 529-41.
Welsh, J.B., et al., Analysis of gene expression identifies candidate markers and pharmacological targets in prostate cancer. Cancer Res, 2001. 61(16): p. 5974-8.
Mori, S., et al., Utilization of genomic signatures to identify phenotype-specific drugs. PLoS One, 2009. 4(8): p. e6772.
Sato, K., et al., Clinical significance of alterations of chromosome 8 in high-grade, advanced, nonmetastatic prostate carcinoma. J Natl Cancer Inst, 1999. 91(18): p. 1574-80.
Casimiro, M., et al., ErbB-2 induces the cyclin D1 gene in prostate epithelial cells in vitro and in vivo. Cancer Res, 2007. 67(9): p. 4364-72.
Gioeli, D., S. Kraus, and M.J. Weber, Signal Transduction by the Ras-MAP Kinase Pathway in Prostate Cancer Progression, in Prostate cancer: signaling networks, genetics, and new treatment strategies, R.G. Pestell and M.T. Nevalainen, Editors. 2008, Humana Press: Totowa, NJ. p. 223-256.
Scherl, A., et al., Prostatic intraepithelial neoplasia and intestinal metaplasia in prostates of probasin-RAS transgenic mice. Prostate, 2004. 59(4): p. 448-59.
Ilio, K.Y., et al., The primary culture of rat prostate basal cells. J Androl, 1998. 19(6): p. 718-24.
Li, Z., et al., Cyclin D1 regulates cellular migration through the inhibition of thrombospondin 1 and ROCK signaling. Mol Cell Biol, 2006. 26(11): p. 4240-56.
Liu, M., et al., p21CIP1 attenuates Ras- and c-Myc-dependent breast tumor epithelial mesenchymal transition and cancer stem cell-like gene expression in vivo. Proc Natl Acad Sci USA, 2009. 106(45): p. 19035-9.
Irizarry, R.A., et al., Summaries of Affymetrix GeneChip probe level data. Nucleic Acids Res, 2003. 31(4): p. e15.
Huang, E., et al., Gene expression phenotypic models that predict the activity of oncogenic pathways. Nat Genet, 2003. 34(2): p. 226-230.
Dai, M., et al., Evolving gene/transcript definitions significantly alter the interpretation of GeneChip data. Nucleic Acids Res, 2005. 33(20): p. e175.
Chen, R., L. Li, and A.J. Butte, AILUN: reannotating gene expression data automatically. Nat Methods, 2007. 4(11): p. 879.
Parkin DM, Fernandez LM. Use of statistics to assess the global burden of breast cancer. Breast J 2006; 12 Suppl 1: S70-80.
Group EBCTC. Effects of chemotherapy and hormonal therapy for early breast cancer on recurrence and 15-year survival: an overview of the randomised trials. Lancet 2005; 365: 1687-717.
Meyers MO, Klauber-Demore N, Ollila DW, Amos KD, Moore DT, Drobish AA, et al. Impact of breast cancer molecular subtypes on locoregional recurrence in patients treated with neoadjuvant chemotherapy for locally advanced breast cancer. Ann Surg Oncol 2011; 18: 2851-7.
Kennecke H, Yerushalmi R, Woods R, Cheang MC, Voduc D, Speers CH, et al. Metastatic behavior of breast cancer subtypes. J Clin Oncol 2010; 28: 3271-7.
Perou CM, Sorlie T, Eisen MB, van de Rijn M, Jeffrey SS, Rees CA, et al. Molecular portraits of human breast tumours. Nature 2000; 406: 747-52.
Reis-Filho JS, Lakhani SR. Breast cancer special types: why bother? J Pathol 2008; 216: 394-8.
Kakinuma T, Hwang ST. Chemokines, chemokine receptors, and cancer metastasis. J Leukoc Biol 2006; 79: 639-51.
Muller A, Homey B, Soto H, Ge N, Catron D, Buchanan ME, et al. Involvement of chemokine receptors in breast cancer metastasis. Nature 2001; 410: 50-6.
Luboshits G, Shina S, Kaplan O, Engelberg S, Nass D, Lifshitz-Mercer B, et al. Elevated expression of the CC chemokine regulated on activation, normal T cell expressed and secreted (RANTES) in advanced breast carcinoma. Cancer Res 1999; 59: 4681-7.
Niwa Y, Akamatsu H, Niwa H, Sumi H, Ozaki Y, Abe A. Correlation of tissue and plasma RANTES levels with disease course in patients with breast or cervical cancer. Clin Cancer Res 2001; 7: 285-9.
Zhang Y, Yao F, Yao X, Yi C, Tan C, Wei L, et al. Role of CCL5 in invasion, proliferation and proportion of CD44+/CD24− phenotype of MCF-7 cells and correlation of CCL5 and CCR5 expression with breast cancer progression. Oncol Rep 2009; 21: 1113-21. Medline.
Jiao X, Katiyar S, Willmarth NE, Liu M, Ma X, Flomenberg N, et al. c-Jun induces mammary epithelial cellular invasion and breast cancer stem cell expansion. J Biol Chem 2010; 285: 8218-26.
Karnoub AE, Dash AB, Vo AP, Sullivan A, Brooks MW, Bell GW, et al. Mesenchymal stem cells within tumour stroma promote breast cancer metastasis. Nature 2007; 449: 557-63.
Locati M, Deuschle U, Massardi ML, Martinez FO, Sironi M, Sozzani S, et al. Analysis of the gene expression profile activated by the CC chemokine ligand 5/RANTES and by lipopolysaccharide in human monocytes. J Immunol 2002; 168: 3557-62.
Robinson SC, Scott KA, Balkwill FR. Chemokine stimulation of monocyte matrix metalloproteinase-9 requires endogenous TNF-alpha. Eur J Immunol 2002; 32: 404-12.
Robinson SC, Scott KA, Wilson JL, Thompson RG, Proudfoot AE, Balkwill FR. A chemokine receptor antagonist inhibits experimental breast tumor growth. Cancer Res 2003; 63: 8360-5.
Manes S, Mira E, Colomer R, Montero S, Real LM, Gomez-Mouton C, et al. CCR5 expression influences the progression of human breast cancer in a p53-dependent manner. J Exp Med 2003; 198: 1381-9.
Murooka TT, Rahbar R, Fish EN. CCL5 promotes proliferation of MCF-7 cells through mTOR-dependent mRNA translation. Biochem Biophys Res Commun 2009; 387: 381-6.
Stormes KA, Lemken CA, Lepre JV, Marinucci MN, Kurt RA. Inhibition of metastasis by inhibition of tumor-derived CCL5. Breast Cancer Res Treat 2005; 89: 209-12.
Jayasinghe MM, Golden JM, Nair P, O'Donnell CM, Werner MT, Kurt RA. Tumor-derived CCL5 does not contribute to breast cancer progression. Breast Cancer Res Treat 2008; 111: 511-21.
Ertel A, Dean JL, Rui H, Liu C, Witkiewicz AK, Knudsen KE, et al. RB-pathway disruption in breast cancer: differential association with disease subtypes, disease-specific prognosis and therapeutic response. Cell Cycle 2010; 9: 4153-63.
Wilkin TJ, Su Z, Krambrink A, Long J, Greaves W, Gross R, et al. Three-year safety and efficacy of vicriviroc, a CCR5 antagonist, in HIV-1-infected treatment-experienced patients. J Acquir Immune Defic Syndr 2010; 54: 470-6.
Barrett T, Troup DB, Wilhite SE, Ledoux P, Rudnev D, Evangelista C, et al. NCBI GEO: mining tens of millions of expression profiles-database and tools update. Nucleic Acids Res 2007; 35: D760-5.
Brazma A, Parkinson H, Sarkans U, Shojatalab M, Vilo J, Abeygunawardena N, et al. ArrayExpress—a public repository for microarray gene expression data at the EBI. Nucleic Acids Res 2003; 31: 68-71.

(56) References Cited

OTHER PUBLICATIONS

Hu Z, Fan C, Oh DS, Marron JS, He X, Qaqish BF, et al. The molecular portraits of breast tumors are conserved across microarray platforms. Bmc Genomics 2006; 7: 96.
Nguyen DH, Taub D. Cholesterol is essential for macrophage inflammatory protein 1 beta binding and conformational integrity of CC chemokine receptor 5. Blood 2002; 99: 4298-306.
Janowski E, Jiao X, Katiyar S, Lisanti MP, Liu M, Pestell RG, et al. c-Jun is required for TGF-beta-mediated cellular migration via nuclear Ca(2) signaling. Int J Biochem Cell Biol 2011; 43: 1104-13.
Velasco-Velazquez MA, Agramonte-Hevia J, Barrera D, Jimenez-Orozco A, Garcia-Mondragon MJ, Mendoza-Patino N, et al. 4-Hydroxycoumarin disorganizes the actin cytoskeleton in B16-F10 melanoma cells but not in B82 fibroblasts, decreasing their adhesion to extracellular matrix proteins and motility. Cancer Lett 2003; 198: 179-86.
Liu H, Patel MR, Prescher JA, Patsialou A, Qian D, Lin J, et al. Cancer stem cells from human breast tumors are involved in spontaneous metastases in orthotopic mouse models. Proc Natl Acad Sci USA 2010; 107: 18115-20.
Zahler MH, Irani A, Malhi H, Reutens AT, Albanese C, Bouzahzah B, et al. The application of a lentiviral vector for gene transfer in fetal human hepatocytes. J Gene Med 2000; 2: 186-93.
Walker DK, Abel S, Comby P, Muirhead GJ, Nedderman AN, Smith DA. Species differences in the disposition of the CCR5 antagonist, UK-427,857, a new potential treatment for HIV. Drug Metab Dispos 2005; 33: 587-95.
Wu K, Katiyar S, Li A, Liu M, Ju X, Popov VM, et al. Dachshund inhibits oncogene-induced breast cancer cellular migration and invasion through suppression of interleukin-8. Proc Natl Acad Sci USA 2008; 105: 6924-9.
Charafe-Jauffret E, Ginestier C, Monville F, Finetti P, Adelaide J, Cervera N, et al. Gene expression profiling of breast cell lines identifies potential new basal markers. Oncogene 2006; 25: 2273-84.
Riaz M, Elstrodt F, Hollestelle A, Dehghan A, Klijn JG, Schutte M. Low-risk susceptibility alleles in 40 human breast cancer cell lines. BMC Cancer 2009; 9: 236.
Hollestelle A, Nagel JH, Smid M, Lam S, Elstrodt F, Wasielewski M, et al. Distinct gene mutation profiles among luminal-type and basal-type breast cancer cell lines. Breast Cancer Res Treat 2010; 121:53-64.
Kao J, Salari K, Bocanegra M, Choi YL, Girard L, Gandhi J, et al. Molecular profiling of breast cancer cell lines defines relevant tumor models and provides a resource for cancer gene discovery. PLoS One 2009; 4: e6146.
Mueller A, Mahmoud NG, Goedecke MC, McKeating JA, Strange PG. Pharmacological characterization of the chemokine receptor, CCR5. Br J Pharmacol 2002; 135: 1033-43.
Petkovic Y, Moghini C, Paoletti S, Uguccioni M, Gerber B. I-TAC/CXCL11 is a natural antagonist for CCR5. J Leukoc Biol 2004; 76: 701-8.
Miyashita M, Smith MW, Willey JC, Lechner JF, Trump BF, Harris CC. Effects of serum, transforming growth factor type beta, or 12-O-tetradecanoyl-phorbol-13-acetate on ionized cytosolic calcium concentration in normal and transformed human bronchial epithelial cells. Cancer Res 1989; 49: 63-7.
Prescher JA, Contag CH. Guided by the light: visualizing biomolecular processes in living animals with bio luminescence. Curr Opin Chem Biol 2010; 14: 80-9.
Yaal-Hahoshen N, Shina S, Leider-Trejo L, Bamea I, Shabtai EL, Azenshtein E, et al. The chemokine CCL5 as a potential prognostic factor predicting disease progression in stage II breast cancer patients. Clin Cancer Res 2006; 12: 4474-80.
Shideman CR, Hu S, Peterson PK, Thayer SA. CCL5 evokes calcium signals in microglia through a kinase-, phosphoinositide-, and nucleotide-dependent mechanism. J Neurosci Res 2006; 83: 1471-84.
Dorr P, Westby M, Dobbs S, Griffin P, Irvine B, Macartney M, et al. Maraviroc (UK-427,857), a potent, orally bioavailable, and selective small-molecule inhibitor of chemokine receptor CCR5 with broad-spectrum anti-human immunodeficiency virus type 1 activity. Antimicrob Agents Chemother 2005; 49: 4721-32.
Strizki JM, Tremblay C, Xu S, Wojcik L, Wagner N, Gonsiorek W, et al. Discovery and characterization of vicriviroc (SCH 417690), a CCR5 antagonist with potent activity against human immunodeficiency virus type 1. Antimicrob Agents Chemother 2005; 49: 4911-9.
Isik N, Hereld D, Jin T. Fluorescence resonance energy transfer imaging reveals that chemokine-binding modulates heterodimers of CXCR4 and CCR5 receptors. PLoS ONE 2008; 3: e3424.
Mira E, Lacalle RA, Gonzalez MA, Gomez-Mouton C, Abad JL, Bernad A, et al. A role for chemokine receptor transactivation in growth factor signaling. EMBO Rep 2001; 2: 151-6.
Rakha et al. (Journal of Clinical Oncology, 2008, 26:2568-2581).
Kim et al Clinicopathologic significance of the basal-like subtype of breast cancer: a comparison with hormone receptor and Her2/neu-overexpressing phenotypes, Human Pathology, 2006, 37:1217-1226.
Tan et al Disruption of CCR5-Dependent homing of Regulatory T Cells Inhibits Tumor Growth in a Murine Model of Pancreatic Cancer, Journal of Immunology, 2009, 182:1746-1755.
Cambien, B. et al., "CCL5 Neutralization Restricts Cancer Growth and Potentiates the Targeting of PDGFRI3 in Colorectal Carcinoma", PLoS ONE, Dec. 2011, vol. 6, Issue 12, e28842-1 to e28842-11.
Van Deventer, H. W. et al., "C-C Chemokine Receptor 5 on Stromal Cells Promotes Pulmonary Metastasis", cancer Res 2005; 65: (8), Apr. 15, 2005, 3374-3379.
Momse, K et al., "Close Resembleance between Chemokine Receptor Expression Profiles of Lymphoproliferative 3 pisease of Granular Lymphocytes and Their Normal Counterparts in Association with Elevated Serum Concentrations of IP-10 and MIG", International Journal of Hematology, 86 (2007), 174-179.
Makishima, H. et al., "Significance of chemokine receptor expression in aggressive NK cell leukemia", Leukemia (2005)19, 1169-1174.
Partial European Search Report dated Mar. 7, 2016 for corresponding European Patent Application No. 13790117.9.
Isik, N., et al., Fluorescence resonance energy transfer imaging reveals that chemokine-binding modulates heterodimers of CXCR4 and CCR5 receptors. PLoS ONE 2008; 3: e3424.
International Searching Authority, PCT Office of USPTO. PCT International Search Report regarding corresponding PCT Application No. PCT/US2013/040917 dated Oct. 21, 2013, pp. 1-5.
Kusuma et al., "Laminin a5-derived peptides modulate the properties of metastatic breast tumour cells", Clin Exp Metastasis (2011) 28:909-921.
Kusuma, N. et al., "Laminin a5-derived peptides modulate the properties of metastatic breast tumour cells", Cin Exp Metastasis (2011) 28:909-921.
McNiff, T. et al., "CCR5 antagonists in the treatment of HIV-infected persons: is their cancer risk increased, decreased, or unchanged." AIDS Read (2009) 19, 218-222, 224.
Non-final Office Action dated Nov. 13, 2018 in U.S. Appl. No. 15/275,050.
Pouliot et al., "investigating Metastasis Using In Vitro Platforms—Madame Curie Bioscience Database—NCBI Bokshellf", (2013) XP055427418, https://www.ncbi.nlm.nih.gov/books/NBK100379.
Van Deventer, H. et al., "C-C Chemokine Receptor 5 on Stromal Cells Promotes Pulmonary Metastasis", Cancer Res (2005) 65: (8) 3374-3379.
Wu, X. et al., "Chemokine Receptors as Targets for Cancer Therapy", Current PHarmaceutical Design. (2009) 15, 742-757.
Schramek, D. et al., "The stress kinase MKK7 couples oncogenic stress to p53 stability and tumor suppression", Nature Genetics, vol. 43, No. 3, Feb. 13, 2011, p. 212-219.
Notice of Reasons for Rejection dated Feb. 24, 2016 for corresponding Japanese Patent Application No. 2013-557917.

* cited by examiner vWF

A

B

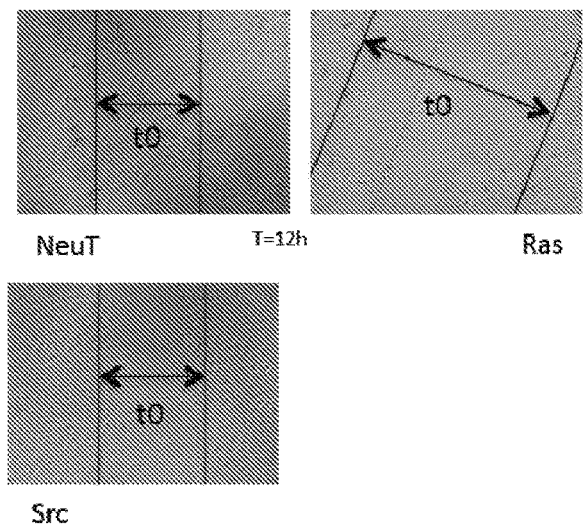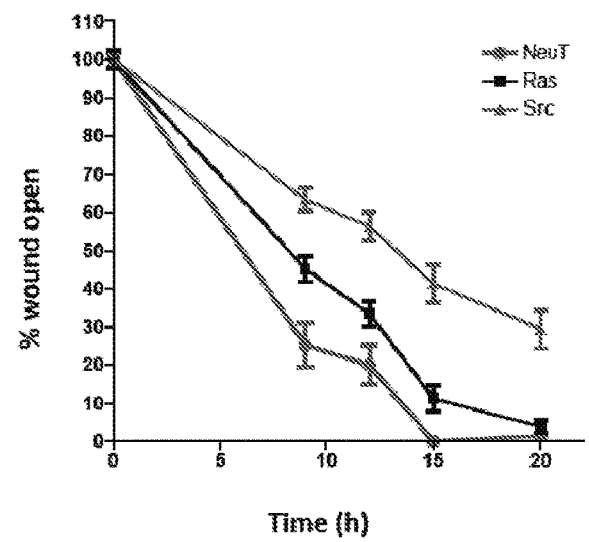
Figure 10A
Figure 10B
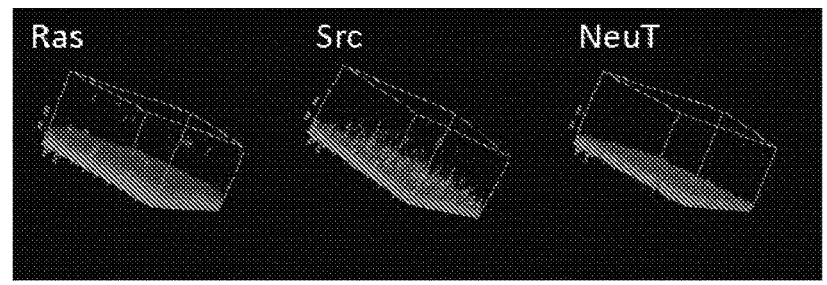
Figure 10C
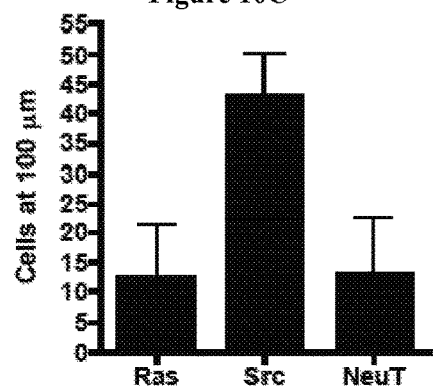
Figure 10D

LIVER

KIDNEY
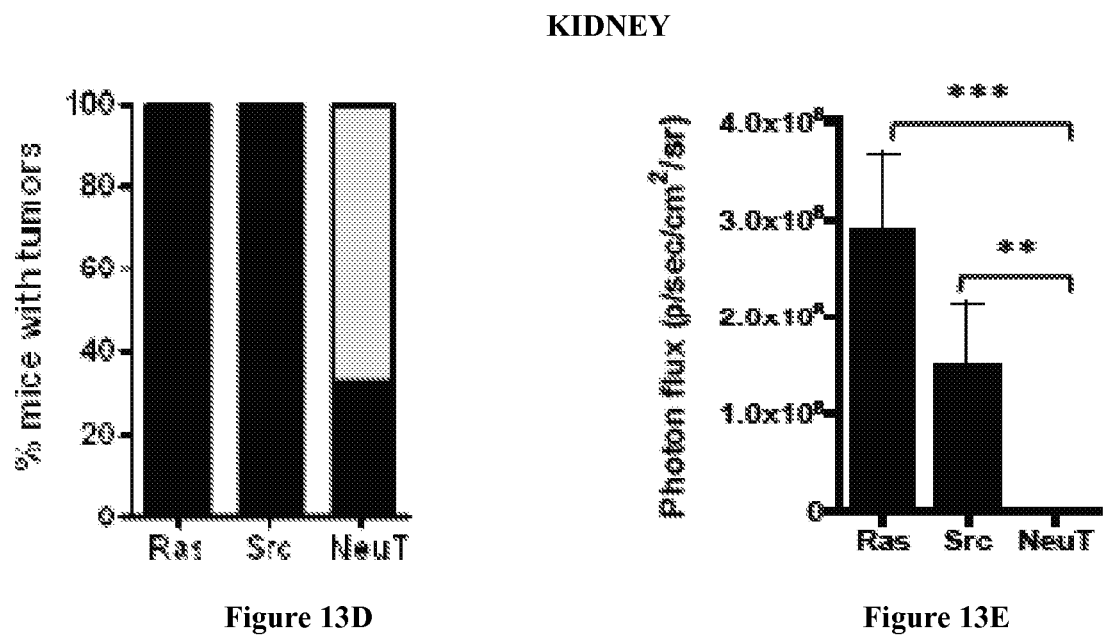
Figure 13D
Figure 13E
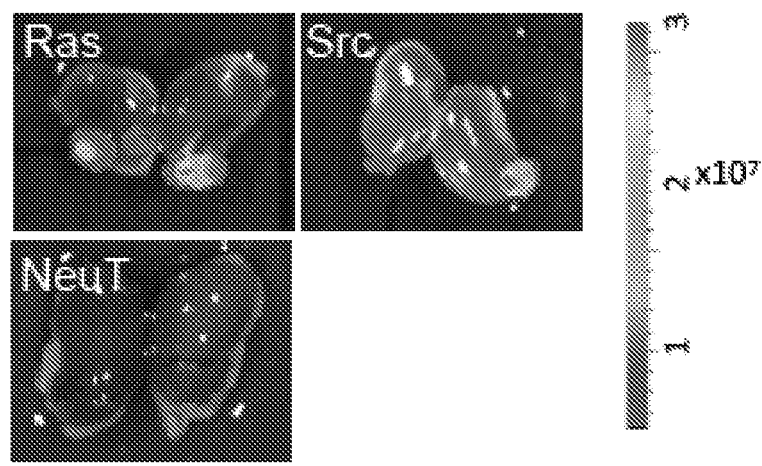
Figure 13F

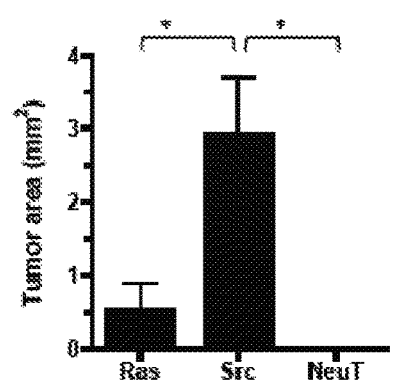 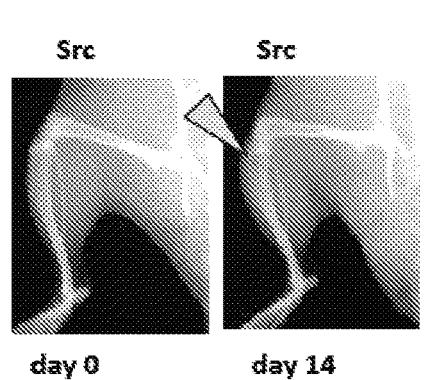 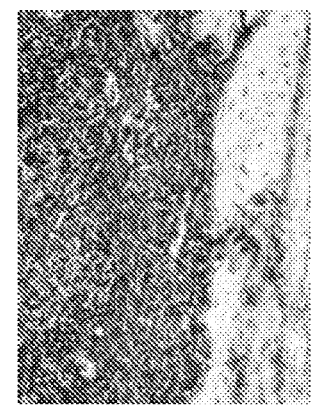
Figure 15A  Figure 15B  Figure 15C
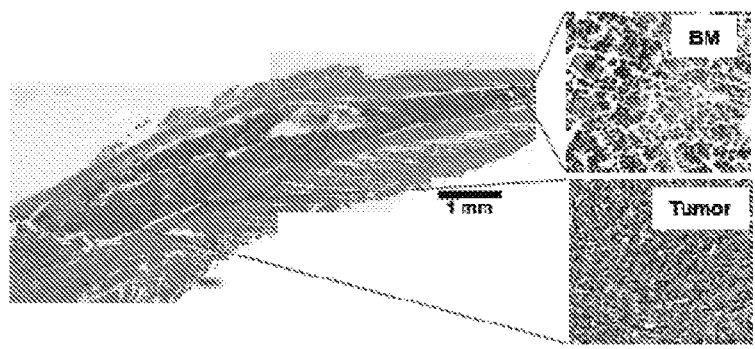
Figure 15D
Figure 15E
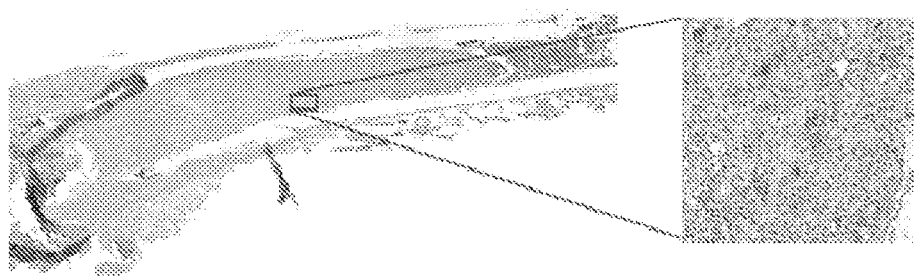
Figure 15

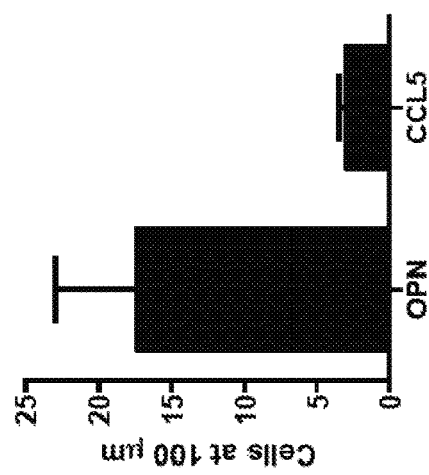
Figure 16E
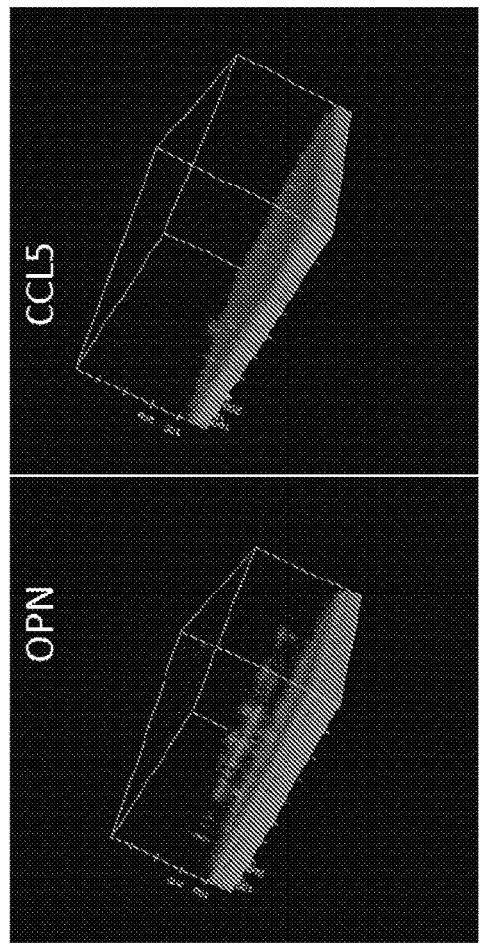
Figure 16D
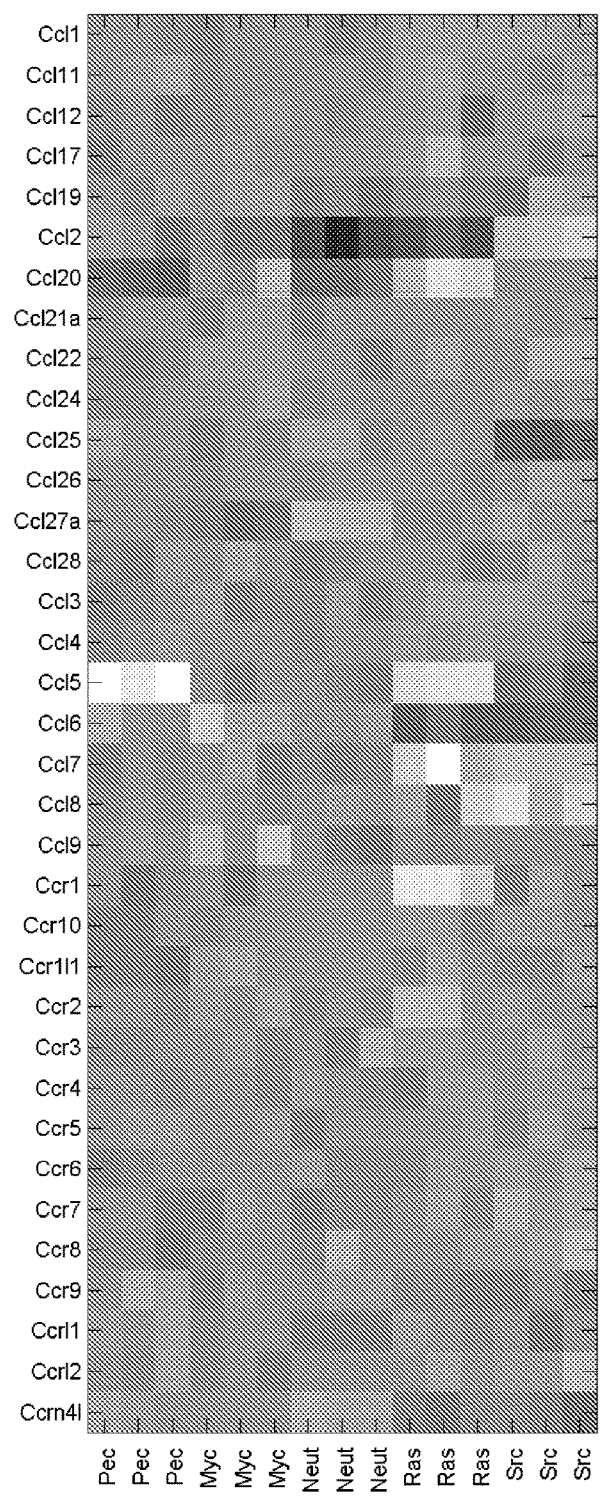
Figure 16F

Figure 17 C
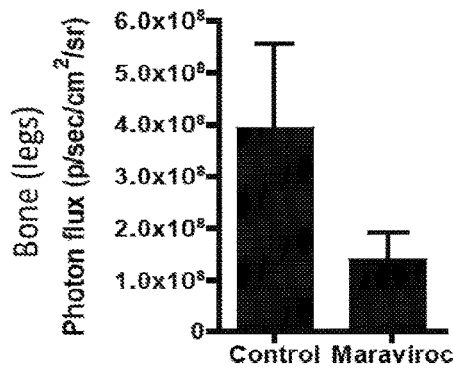
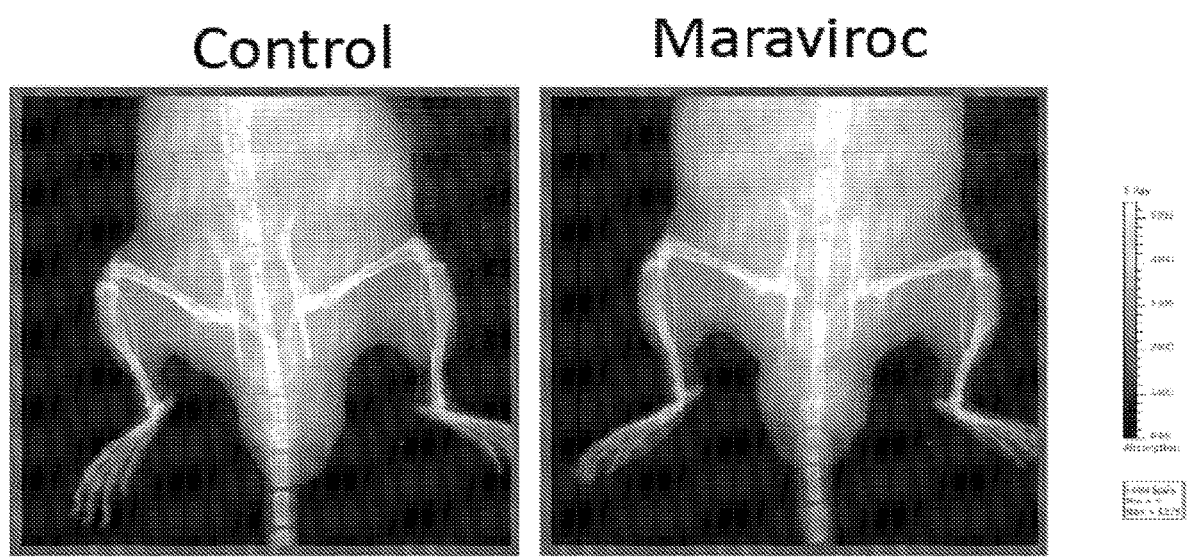
Figure 17D

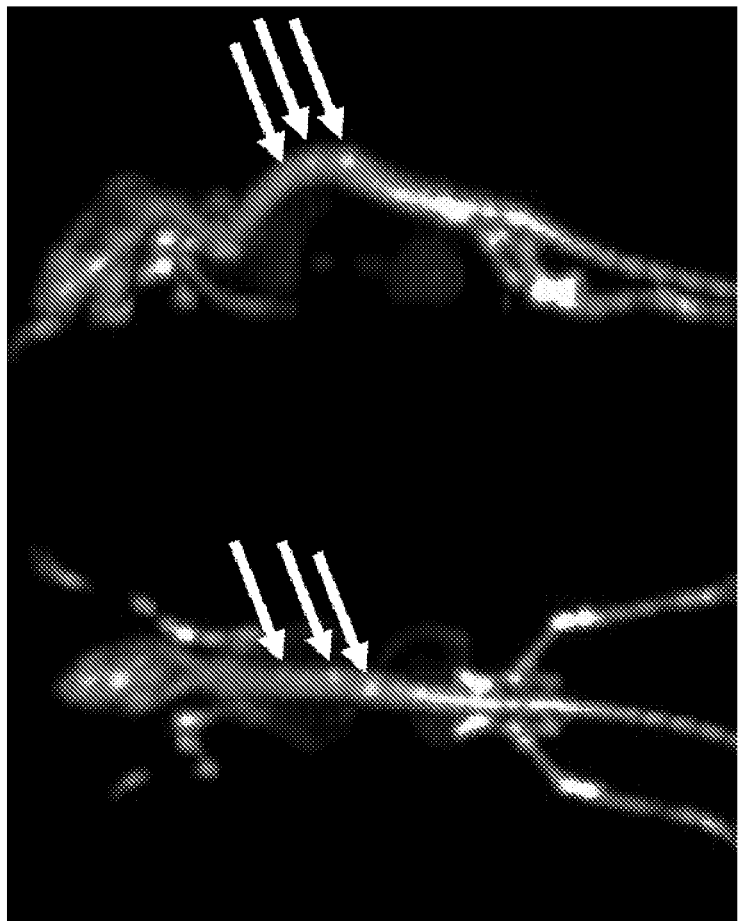
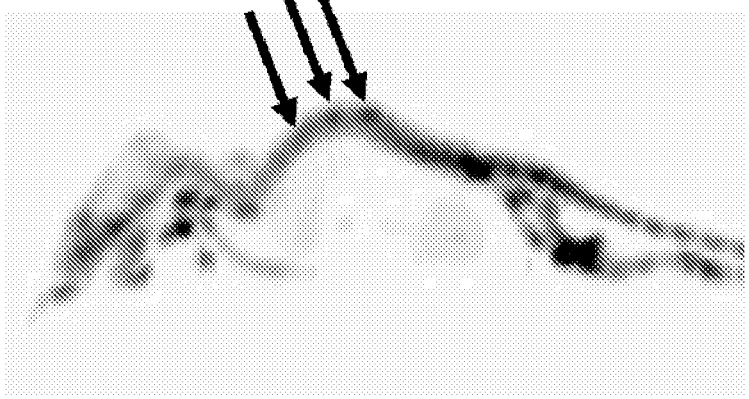
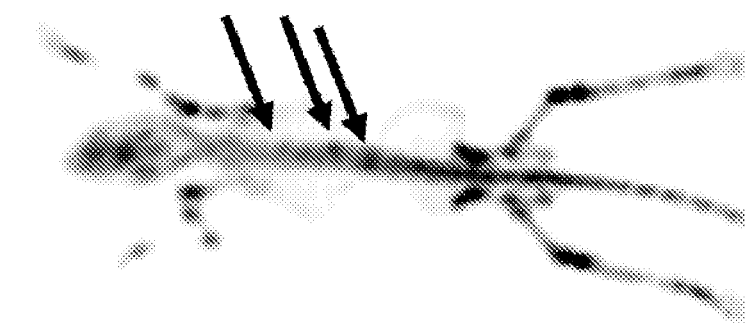
Figure 18A  Figure 18B  Figure 18C  Figure 18D

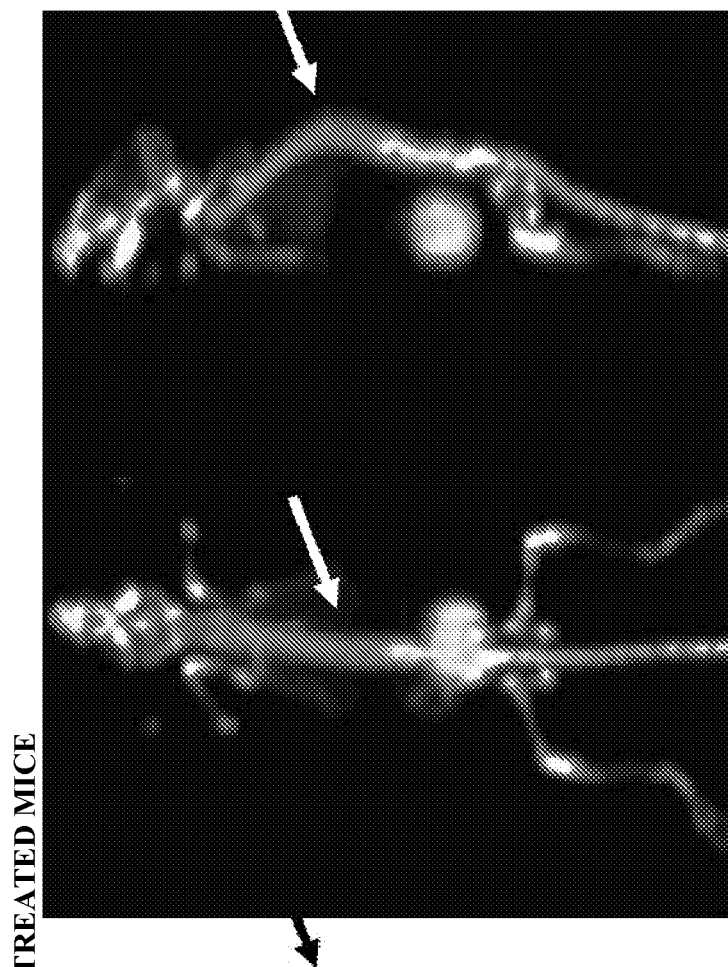
Figure 18H
Figure 18G
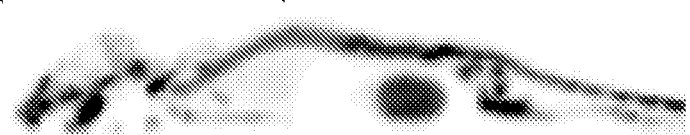
Figure 18F
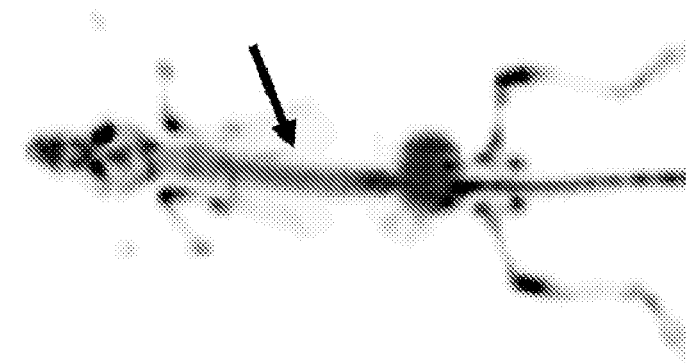
Figure 18E

UNTREATED MICE

TREATED MICE

DATA FRPOM TPEC CELL LINE MICROARRAY

| | | Myc FC | Myc P | Neut FC | Neut P | Ras FC | Ras P | Src FC | Src P |
|---|---|---|---|---|---|---|---|---|---|
| Ccr1 | chemokine (C-C motif) receptor 1 | 1.014198095 | 0.370653451 | 1.079653791 | 0.170581362 | 2.248091085 | 0.001762398 | 1.121698047 | 0.153773025 |
| Ccrl1 | chemokine (C-C motif) receptor 1-like 1 | 1.278404003 | 0.001915931 | 1.192997475 | 0.002904869 | 1.211613809 | 0.025677095 | 1.163781114 | 0.014221878 |
| Ccr8 | chemokine (C-C motif) receptor 8 | 1.115749164 | 0.060464299 | 1.226749716 | 0.064113911 | 1.199219818 | 0.027892145 | 1.383014405 | 0.002036917 |
| | | 0.866653571 | 0.211698255 | 0.479609371 | 0.001018562 | 19.13298288 | 6.101143 | | |
| Ccl2 | chemokine (C-C motif) ligand 2 | 1.526337798 | 0.008259944 | 1.015071961 | 0.408219585 | 7.317501169 | 0 | 1.430072892 | 0.000222585 |
| Ccl20 | chemokine (C-C motif) ligand 20 | 1.190935896 | 0.002041387 | 1.043967609 | 0.309482402 | 1.135892229 | 0.073192107 | 1.266326049 | 0.012633923 |
| Ccl22 | chemokine (C-C motif) ligand 22 | 0.878226778 | 0.257047917 | 1.028638047 | 0.403664413 | 0.953086405 | 0.517867088 | 0.605133822 | 0 |
| Ccl25 | chemokine (C-C motif) ligand 25 | 0.815333352 | 0.002638799 | 1.287082023 | 0.001080676 | 0.969360548 | 0.497511096 | 1.047860034 | 0.233945977 |
| Ccl27a | chemokine (C-C motif) ligand 27A | 0.306188 | 0.295023 | | | 1.353974 | 0.004346 | 0.252512 | |
| Ccl5 | chemokine (C-C motif) ligand 5 | 1.187246921 | 0.135416 | 0.929596076 | 0.418556 | 0.630127381 | 0.004352863 | 0.620339944 | 0 |
| Ccl6 | chemokine (C-C motif) ligand 6 | 1.086205817 | 0.201387524 | 0.970472424 | 0.413858 91 | 5.400849498 | 0.001354193 | 1.508023012 | 0.000116215 |
| Ccl7 | chemokine (C-C motif) ligand 7 | 1.068983036 | 0.145213706 | 1.083141783 | 0.091766 82 | 1.330116 01 | 0.239660095 | 1.789665 76 | 0 |
| Ccl8 | chemokine (C-C motif) ligand 8 | 258 | 171 | 38 | 088 | 582 | 525 | 489 | 509 |

Figure 20

PROSTATE CANCER CELL LINES, GENE SIGNATURES AND USES THEREOF

CROSS REFERENCE TO RELATED APPLICATIONS

This application is a U.S. national phase application filed under 35 U.S.C. § 371 of International Application No. PCT/US2012/028546, which was filed Mar. 9, 2012, and which claims the benefit of the filing date of U.S. Provisional Application No. 61/450,767, which was filed Mar. 9, 2011.

GOVERNMENT LICENSE RIGHTS

This invention was made with government support under grant numbers R01CA70896, 10 R01CA75503, R01CA86072, P30CA56036, and R01CA132115-02 awarded by the National Institutes of Health. The government has certain rights in the invention.

FIELD OF THE INVENTION

Methods and compositions for diagnosing and treating cancer, including prostate cancer, are provided. Particular aspects of the present invention relate to methods and compositions useful for prostate cancer diagnostics, research, treatment stratification, and treatment. Also provided in the invention are cells and transgenic, non-human mammals that can be used in these methods.

BACKGROUND OF THE INVENTION

Cancer is a significant health problem throughout the world. Although advances have been made in detection and therapy of cancer, no vaccine or other universally successful method for prevention and/or treatment is currently available. Current therapies, which are generally based on a combination of chemotherapy or surgery and radiation, continue to prove inadequate in many patients.

Prostate cancer, for example, is a significant health problem for men in the United States and throughout the world. Although advances have been made in the detection and treatment of the disease, prostate cancer remains an important cause of cancer-related deaths in men, affecting more than 221,000 men in the United States each year. For men in North America, the life-time odds of getting prostate cancer are now 19.6%, with a 4.6% risk of death. Prostate cancer was the cause of approximately 250,000 deaths worldwide in 2009.

No vaccine or other universally successful method for the prevention or treatment of prostate cancer is currently available. Management of the disease currently relies on a combination of early diagnosis (through routine Prostate-Specific Antigen ("PSA") test) and aggressive treatment, which may include one or more of a variety of treatments such as surgery, radiotherapy, chemotherapy and hormone therapy. The course of treatment for a particular Prostate cancer is often selected based on a variety of prognostic parameters, including an analysis of histology and disease spread. However, the use of PSA, which is the current standard for screening, results in less than optimal treatment decisions because the PSA test has high false positive and false negative rates. Approximately 45 million PSA were conducted in 2009 min the USA, with a specificity of approximately 27%. Approximately 1 million biopsies of the prostate were undertaken last year in the USA based on elevated PSA, from which 250,000 tumors were identified.

The high mortality observed in prostate cancer patients indicates that improvements are needed in the treatment, diagnosis and prevention of the disease.

Another complicating factor with the use of PSA test is that doctors' recommendations for PSA screening vary. Some encourage yearly screening for men over age 50, and some advise men who are at a higher risk for prostate cancer to begin screening at age 40 or 45. Yet others caution against routine screening. Typically, PSA level below 4.0 ng/mL is considered as normal. However, the referenced PSA level seem arbitrary and useless in view of two reports, one by Thompson I M et al. ("Prevalence of prostate cancer among men with a prostate-specific antigen level < or =4.0 ng per milliliter," New England Journal of Medicine 2004, 350(22), 2239-2246) and the other by Smith D S et al. ("The early detection of prostate carcinoma with prostate specific antigen: The Washington University experience," Cancer 1997, 80(9), 1853-1856). According to Thompson I M et al. prostate cancer was diagnosed in 15.2 percent of men with a PSA level at or below 4.0 ng/mL. Fifteen percent of those men, or approximately 2.3 percent overall, had high-grade cancers. According to Smith D S et al. 25 to 35 percent of men who had a PSA level between 4.1 and 9.9 ng/mL and who underwent a prostate biopsy were found to have prostate cancer, while 65 to 75 percent of the remaining men did not have prostate cancer. Thus, there is no specific normal or abnormal PSA level.

Also, molecular mechanisms contributing to prostate cancer recurrence and therapy resistance are poorly understood. Androgen ablation therapy results in 60% to 80% initial response rate (see Scher, H. I., and Sawyers, C. L., J Clin Oncol 2005, 23, 8253-8261). The majority of patients undergoing androgen antagonist therapy however subsequently relapse. Early diagnosis may provide an opportunity for curative surgery, however ~30% of men who receive radical prostatectomy relapse, attributed to micrometastatic disease. Therefore, a need exists medical interventions that can detect and/or forestall molecular drivers of metastatic malignancy at early stages of the disease.

SUMMARY OF THE INVENTION

In one aspect, the present invention provides a mammalian prostate cancer cell line comprising at least one or more of a set of primary mammalian epithelial cells which have been infected with a retroviral vector carrying an oncogene. In certain embodiments, the oncogene is selected from the group consisting of c-Myc, Ha-Ras, NeuT, c-Src and combinations thereof and in which said oncogene or combination of genes is expressed. The mammalian prostate cancer cell line can include any suitable mammalian cell, including primary murine epithelial cells. The primary mammalian epithelial cells may be derived from any immune competent mammal, including immune competent rodents, including rats and mice.

In another aspect, the present invention provides an animal model of cancer comprising an immune competent mammal implanted with a cancer cell line transformed with one or more of a set of oncogenes selected from the group consisting of c-Myc, Ha-Ras, NeuT, c-Src and combinations thereof.

In one embodiment, an immunocompetent transgenic mouse created using the mammalian prostate cancer cell line of the present invention develops a prostate tumor capable of producing a detectable molecular genetic signature based on an expression level of one or more of a set of oncogenes selected from the group consisting of c-Myc, Ha-Ras, NeuT, c-Src and combinations thereof.

In yet another aspect, the present invention provides a method for the in vitro production of immortalized primary mammalian epithelial cells, the method comprising infecting primary mammalian epithelial cells with a retroviral vector carrying an oncogene selected from the group consisting of c-Myc, Ha-Ras, NeuT, c-Src and combinations thereof to provide infected cells, wherein said primary mammalian epithelial cells are capable of being infected by said retroviral vector and under conditions whereby the c-Myc, Ha-Ras, NeuT, c-Src and combinations thereof are expressed in said infected cells.

In a further aspect, the present invention provides a method for diagnosing a prostate cancer, the method comprising: (a) providing a biological test sample from a subject afflicted with a prostate cancer or suspected of having prostate cancer or at risk for developing prostate cancer; (b) determining a level of at least one biological marker or a molecular genetic signature based on a gene expression pattern or activity of one or more of a set of genes in the test sample, wherein the one or more set of genes are selected from the group consisting of c-Myc, Ha-Ras, NeuT, c-Src and combinations thereof; (c) comparing the level of said at least one biological marker or said molecular genetic signature in said test sample to the level of the biological marker or the level of the molecular genetic signature in a control sample, wherein an elevated level of the biological marker or the molecular genetic signature in said test sample relative to the level of the biological marker or the molecular genetic signature in said control sample is a diagnostic indicator of the presence of prostate cancer in said subject.

In yet another aspect, the present invention provides a method of classifying a cancer tumor, including a prostate tumor, the method comprising: (a) providing a cancer tumor or a prostate tumor sample; (b) detecting a molecular genetic signature derived from gene expression pattern or activity of one or more of a set of genes in the sample, wherein the genes are selected from the group consisting of c-Myc, Ha-Ras, NeuT, c-Src and combinations thereof; and (c) classifying the prostate tumor as belonging to a tumor subclass based on the results of the detecting step (b).

In a further aspect, the present invention provides a method of stratifying a subject having a cancer tumor, including a prostate tumor, for a clinical trial, the method comprising: (a) providing a sample derived from a subject having the cancer tumor or the prostate tumor; (b) detecting a molecular genetic signature derived from gene expression pattern or activity of one or more of a set of genes in the sample, wherein the genes are selected from the group consisting of c-Myc, Ha-Ras, NeuT, c-Src, ErbB2 and combinations thereof; and (c) stratifying the subject for a clinical trial based on the results of the detecting step.

In another aspect, the present invention provides a method of selecting a treatment for a subject having a prostate tumor, the method comprising: (a) providing a sample derived from a subject having a prostate tumor; (b) detecting a molecular genetic signature derived from a gene expression pattern or activity of one or more of a set of genes in the sample, wherein the genes are selected from the group consisting of c-Myc, Ha-Ras, NeuT, c-Src and combinations thereof; and (c) selecting a treatment based on the results of the detecting step.

In yet another aspect, the present invention provides a non-naturally occurring cell produced by transforming a cell with one or more exogenous oncogenes, allowing the cell to divide at least once, wherein the cell is a mammalian cell transformed by a vector containing the one or more exogenous oncogenes, wherein the one or more exogenous oncogenes are selected from the group consisting of c-Myc, Ha-Ras, NeuT, c-Src and combinations thereof.

It has been discovered that oncogene transformation of prostate epithelial cells induces metastatic cells associated with increased expression of chemokine receptor type 5 ("CCR5") and its ligands (CCL5, CCL8, CCL7). The CCR5 receptor is functionally relevant to the bony metastasis as evidenced by the reduction in metastasis with daily oral CCR5 antagonist Maraviroc.

BRIEF DESCRIPTION OF THE DRAWINGS

FIG. 10 illustrates Src enhancement of 3D Matrigel invasion of isogenic prostate cancer cell lines, wherein:

FIG. 10A illustrates wounding assay of cellular migration showing wound,

FIG. 10B illustrates quantitation of closure for N=3 separate experiments,

FIG. 10C illustrates 3-D invasion assay using prostate cancer cell lines in matrigel, and FIG. 10D illustrates mean distances of invasion±SEM from 3 independent experiments for PEC lines (PEC-NeuT, PEC-Ras, and PEC-Src);

FIG. 11 illustrates isogenic prostate cancer cell line tumors are vascular, wherein:

FIG. 12 illustrates prostate cancer lines develop metastasis. Results from an experiment wherein PEC lines transduced with vectors expressing the Luc2-Tomato-Red fusion protein were injected into the ventricle of FVB mice and the in vivo bioluminescent signal was quantified weekly, presented as follows:

FIG. 13 illustrates liver metastasis of prostate tumor cell lines. Results from an experiment wherein isogenic PEC lines expressing the Luc2-Tomato-Red fusion protein were injected into the ventricle of FVB mice and the in vivo bioluminescent signal quantified are presented as follows:

FIG. 13D illustrates the percentage of mice with kidney tumors,

FIG. 13E illustrates size of kidney tumors by photon flux, and

FIG. 13F illustrates representative images of kidney metastasis;

FIG. 14 illustrates isogenic prostate cancer cell lines develop osteolytic bone metastases:

FIG. 15 illustrates Src enhancement of osteolytic prostate cancer bone metastases. Results from an experiment wherein FVB mice 2 weeks after PEC-Src intracardiac injection developed osteolytic bone lesions presented as follows:

FIG. 15A illustrates that tumor area in bones was significantly increased in the PEC-Src group compared with PEC-Ras and PEC-NeuT, FIG. 15B illustrates representative X-Rays before (t0) and 14 days (t14) after intracardiac injection of cells, FIG. 15C illustrates Tartrate-Resistant Acid Phosphatase ("TRAP") staining, corroborating the presence of osteoblast (arrows) in the bone-tumor interface, FIG. 15D illustrates H&E staining of bone metastasis formed after, FIG. 15E illustrates CK14 staining and, FIG. 15F illustrates CK8 staining, and both corroborate the presence of epithelial cells within bone;

FIG. 16 illustrates osteolytic prostate cancer cell lines express function CCL5 and osteopontin ("OPN") receptors:

FIG. 16D illustrates Matrigel invasion assays of the PEC-Src line conducted using OPN as CD44 ligand and CCL5 as CCR5 ligand, and FIG. 16E illustrates Matrigel invasion of the PEC-Src line quantified as mean±SEM, and FIG. 16F illustrates chemokine receptor and ligand gene expression of prostate tumor cell lines in tissue culture.

FIG. 17 illustrates CCR5 antagonists blocking spinal osteolytic prostate cancer metastasis. Results from an experiment wherein PEC lines transduced with vectors expressing the Luc2-Tomato-Red fusion protein were injected into the ventricle of FVB mice and the in vivo bioluminescent signal was quantified after 2 weeks are shown in FIGS. 17A-17D:

FIG. 17C illustrates lower limb bony mass in the mice (Data are mean±SEM for N=8 separate mice in each group, $P<0.05$); and FIG. 17D shows representative X-ray images of lower limb bony mass in the mice.

FIGS. 18A-18H illustrate flurine-18, sodium fluoride ("F-18-NaF") imaging correlated with X-ray analysis demonstrated the presence of spine metastasis;

FIG. 20 illustrates data from tPEC cell line microarray.

DETAILED DESCRIPTION OF THE INVENTION

Figure 1:
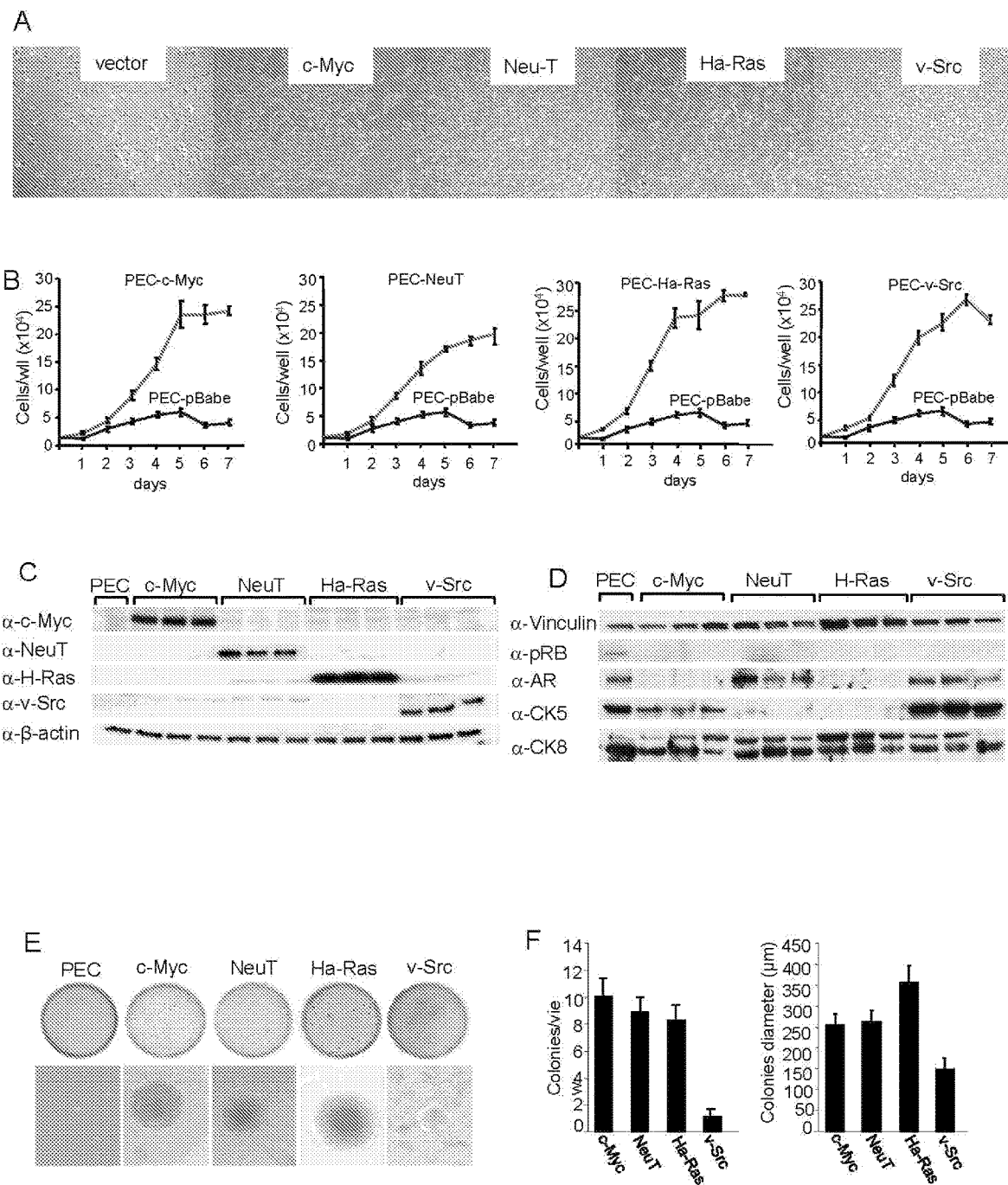
FIG. 1 illustrates oncogene transduced PEC lines form colonies in soft agar.

The present subject matter will now be described more fully hereinafter with reference to the accompanying Figures and Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entirety.

I. Animal Models and Cell Lines:

New treatments for diseases, such as cancer and in particular prostate cancer, require new testing regimes in animals. These testing regimes have been limited by the lack of prostate cancer cell lines that can be implanted in immune competent (or "immunocompetent") animals. This is important because the immune system plays an important role in the onset and progression of human prostate cancer. To screen of new drugs useful for treating patients with prostate cancer it is necessary to develop prostate cancer cell lines that can be studied in immune competent animals, which reflect the human disease by histology, and undergo the same type of behavior in vivo, including metastasis to the lungs and bones as occurs in human disease.

Accordingly, an aspect of the present invention provides cancer cell lines that can be implanted in immune competent, or immunocompetent, animals, including humans and non-human animals, including mammals. Exemplary non-human mammals include, for example, rodents such as rats, guinea pigs, and mice, and faint animals such as pigs, sheep, goats, horses, and cattle.

As any type of cell in the body may be a source of cancer, any suitable type of cancer cell line may be used in the present invention. A suitable cancer type includes carcinoma (cancer of the epithelial cells), sarcoma (cancer of the bone, muscle or other connective tissues), lymphoma (cancer of the lymphatic system), leukemia (cancer of blood cells or blood precursor cells) and melanoma (cancer of the pigment-providing cells).

In one embodiment, a prostate cancer cell line is provided, wherein the prostate cell line comprises at least one or more of a set of primary mammalian epithelial cells which have been infected with a retroviral vector carrying an oncogene selected from the group consisting of c-Myc, Ha-Ras, NeuT, c-Src and combinations thereof, and wherein said oncogene or combinations of genes are expressed.

In one embodiment, a mouse prostate cancer cell line is provided, wherein murine prostate cells are trunsduced with an oncogene selected from the group consisting of c-Myc, Ha-Ras, NeuT, c-Src and combinations thereof. Suitable mouse prostate cell line can be obtained by infecting the primary murine epithelial cells with a retroviral vector carrying the oncogene under conditions that allow the oncogene to be expressed in the primary murine epithelial cells.

Transgenic immunocompetent mouse models of human cancers, for example, have the potential to be more reflective of human cancers than xenograft models because, inter alia, transgenic mice form tumors in situ, (i.e., in an environment more similar to the human tumor and in the setting of a normal immune system). Therefore, in some embodiments of the present invention, immunocompetent non-human mammals are engineered to express one or more of the oncogenes described herein, including c-Myc, Ha-Ras, NeuT, c-Src or combinations thereof, and to develop cancer There several advantages to using transgenic mouse models of human cancer in research. For example, small-animal X-ray computed tomography (microCT) could be used to monitor progression of tumor relatively cheaply and also as highly quantitative three-dimensional method for visualizing blood vessels and angiogenesis preclinically. Using such a method it is possible to achieve rapid and accurate assessment of vascularity during preclinical therapeutic trials in living mice. Tumor assessment with microCT enables rapid qualitative visual renderings of data as well as quantitative analysis of tumor blood volume, vessel density, vessel caliber, degree of branching, and tortuosity using segmentation analysis.

Examples of immunocompetent mice that are suitable for use in the present invention include (random bred CD1, Charles River Laboratories, St. Constant, PQ), C57BI/6J (B6), C57BI/6×129/J F1 (F1, Jackson Laboratories, Bar Harbor, Me.), FVB/N, C57BV6, BALB/c and ND4.

In a preferred embodiment FVB/N mice are used to engineer the transgenic mouse models in accordance with the present invention. FVB/N mice are suitable for most transgenic experiments and genetic analyses contemplated and/or described herein. The inbred FVB/N strain is characterized by vigorous reproductive performance and consistently large litters and fertilized FVB/N eggs contain large and prominent pronuclei, which facilitate microinjection of DNA.

An immunocompetent transgenic mouse created using the mammalian prostate cancer cell line of the present invention develops a prostate tumor capable of producing a detectable molecular genetic signature based on an expression level of one or more of a set of oncogenes selected from the group consisting of c-Myc, Ha-Ras, NeuT, c-Src and combinations thereof.

Metastasis is the leading cause of death in cancer patients. Current chemotherapeutic anti-cancer treatments use cytotoxic, hormonal or immunomodulator drugs aimed at decreasing the number of cancer cells in the patient's body. However, a growing body of evidence suggests that most metastatic cells are resistant to anti-cancer drugs and therefore currently available drugs are not effectively stopping the dissemination of cancer cells to other tissues or organs. At present, there is no effective method for treating most metastatic tumors despite the numerous and diverse therapeutic innovations in the cancer therapeutic field.

A "vector" or "construct" refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus, adeno-associated virus (AAV), poxvirus, papillomavirus, lentivirus, herpesvirus, foamivirus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

Human Prostate cancer has embedded within the genetic makeup and signatures that reflect oncogenic signaling. The cell lines of the present invention advantageously reflect one or more of these oncogenic signaling pathways, thus facilitating, for example, the testing of oncogene specific compounds or nucleic acids based therapies. In particular, prostate cancer cell lines as provided herein are useful for the testing of and/or screening for oncogene specific compounds or nucleic acids based therapies.

Examples of suitable oncogene specific inhibitors include inhibitors for c-Myc, Ha-Ras c-Src, and ErbB2 oncogenes. Several suitable anti-cancer agents targeting the ErbBs, which are in clinical use or development, including those that fall in the categories of chimeric or humanised monoclonal antibodies against the ErbB family and Small Molecule ErbB Tyrosine Kinase Inhibitors. The chimeric or humanised monoclonal include antibodies that prevent ligand-binding and ligand-dependent receptor activation (e.g., Cetuximab that targets the ligand-binding subdomain III of ErbB1), antibodies that interfere with ligand-independent receptor activation (e.g., Trastuzumab that targets subdomain IV of ErbB2), and antibodies that prevent receptor heterodimerisation (e.g. the anti-ErbB2 antibody Pertuzumab that targets an area around the dimerisation loop in subdomain II of ErbB2). Exemplary Small molecule ErbB tyrosine kinase inhibitors include two ErbB1-specific tyrosine kinase inhibitors Gefitinib/Iressa and Erlotinib, which have been approved for the treatment of non-small cell lung cancer, and the dual ErbB1/ErbB2 inhibitor Lapatinib, which is marketed as TYKERB® and is indicated in combination with capecitabine for the treatment of patients with advanced or metastatic breast cancer; and in combination with letrozole for the treatment of postmenopausal women with hormone receptor positive metastatic breast cancer that overexpresses the HER2.

Other ErbB2 receptor inhibitors include GW-282974 (Glaxo Wellcome PLC), and the monoclonal antibodies AR-209 (Aronex Pharmaceuticals Inc. of The Woodlands, Tex., USA) and 2B-1 (Chiron). Exemplary ErbB2 inhibitors also include those described in WO 1998/02434 (published Jan. 22, 1998), WO 1999/35146 (published Jul. 15, 1999), WO 1999/35132 (published Jul. 15, 1999), WO 1998/02437 (published Jan. 22, 1998), WO 1997/13760 (published Apr. 17, 1997), WO 1995/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117, 346, filed Jan. 27, 1999, both of which are herein incorporated by reference in their entirety.

Examples of c-Src protein tyrosine kinase inhibitors that are useful in the present invention include, but are not limited to, the compounds which are generically and specifically disclosed in WO 1996/10028, WO 1997/28161, WO1997/32879 and WO1997/49706, including those belonging to the structure classes of pyrrolopyrimidines, especially pyrrolo[2,3-d]pyrimidines, purines, pyrazo-pyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Exemplary compounds include compounds of formulae I-IV below.

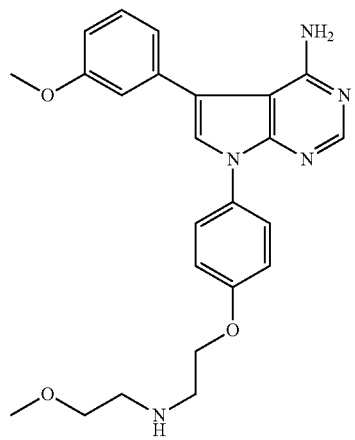

I

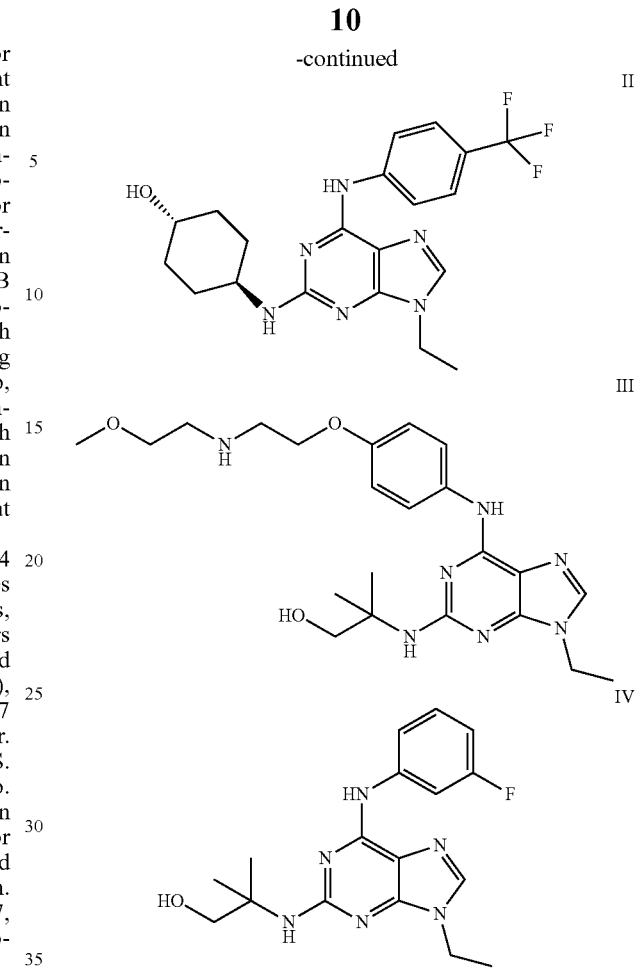

The above compounds can be prepared and administered as described in the cited documents. The compound of formula I can be prepared and formulated as described in WO 1996/10028. The compound of formula II and its preparation is disclosed in Example 111c3 of WO 1997/16452. The compound of formula IV can be prepared in analogy thereof. Both latter compounds can be formulated as described in WO 1997/16452. The compound of formula III is discussed by R. Gamse et al. in J. Bone Miner. Res. 14 (Suppl. 1), 1999, S487.

Additional useful compounds (e.g., PP1) are described by T. Schindler, F. Sicheri et al. in Molecular Cell, 1999 (3), 639, 647; J. M. Hamby et al., J. Med. Chem. 40, 1997, 2296-2303; R. L. Panek et al., J. Pharmacol. Exp. Ther. 283, 1997, 1433-1444; and S. R. Klutchko et al., J. Med. Chem. 41, 1998, 3276-3292.

Other src inhibitors include SKI606, also known as bosutinib (by Wyeth) and the compound dasatinib, also know as Spyrcel (by Bristol-Myers Squibb) which is disclosed in WO 2000/62778 and U.S. Pat. No. 6,596,746. All of these src inhibitors are incorporated herein in their entirety.

Small-molecule c-Myc inhibitors include 10074-G5, also known as Biphenyl-2-yl-(7-nitrobenzo[1,2,5]oxadiazol-4-ylamine; Quarfloxin (also known as CX-3543); and 10074-G5, also known as Biphenyl-2-yl-(7-nitrobenzo[1,2,5]oxadiazol-4-ylamine. CX-3543 reportedly suppresses c-Myc activity by binding to the c-Myc quadruplex, four-stranded DNA secondary structures that regulate transcription of specific oncogenes including c-Myc.

Other c-Myc inhibitors include the compounds disclosed in United States Patent Application Publication No. 2007/

0203188 (published Aug. 30, 2007). These c-Myc inhibitors are incorporated herein in their entirety.

In yet another aspect, the present invention provides a method for the in vitro production of immortalized primary mammalian epithelial cells, the method comprising infecting primary mammalian epithelial cells with a retroviral vector carrying an oncogene selected from the group consisting of c-Myc, Ha-Ras, NeuT, c-Src and combinations thereof to provide infected cells, wherein said primary mammalian epithelial cells are capable of being infected by said retroviral vector and under conditions whereby the c-Myc, Ha-Ras, NeuT, c-Src and combinations thereof are expressed in said infected cells.

Any suitable gene delivery system can be used in the present invention. Particular examples of suitable gene delivery systems include Retroviral and Adenoviral Expression Systems. Retroviral-mediated gene transfer is widely used to express proteins in a variety of cell lines, including hematopoietic cells for a variety of reasons, including analysis of their effects on blood cell proliferation, differentiation, and biological function. In particular, the Murine Stem Cell Virus ("MSCV") Retroviral Expression System (by Clontech Laboratories, Inc) contains vectors that are optimized for introducing and expressing target genes in pluripotent cell lines, including murine or human hematopoietic, embryonic stem (ES), and embryonal carcinoma (EC) cells. Particular examples of Adenoviral Expression Systems, include the ViraPower™ Adenoviral Expression System (by Life Technologies), which is useful, for example, for creation of a replication-incompetent adenovirus that can be used to deliver and transiently express target gene(s) of interest in either dividing or non-dividing mammalian cells.

II. Methods of Use:

In another aspect, the present invention provides a method for diagnosing a prostate cancer, the method comprising: (a) providing a biological test sample from a subject afflicted with a prostate cancer or suspected of having prostate cancer or at risk for developing prostate cancer; (b) determining a level of at least one biological marker or a molecular genetic signature based on a gene expression pattern in the test sample that is associated with the diagnosis of the prostate cancer; (c) comparing the level of said at least one biological marker or said molecular genetic signature in said test sample to the level of the biological marker or the level of the molecular genetic signature in a control sample, wherein an elevated level of the biological marker or the molecular genetic signature in said test sample relative to the level of the biological marker or the molecular genetic signature in said control sample is a diagnostic indicator of the presence of prostate cancer in said subject.

In an embodiment, biological specimens include nucleic acid derived from the tumor under obtained from the patient. Nucleic acid may be derived from the tumor either by biopsy, or from cells derived from the tumor in urine or proteins made as a consequence of the gene signature secreted into the patients blood.

In yet another aspect, the present invention provides a method of classifying a prostate tumor, the method comprising: (a) providing a prostate tumor sample; (b) detecting a molecular genetic signature derived from gene expression pattern or activity of one or more of a set of genes in the sample, wherein the genes are selected from the group consisting of c-Myc, Ha-Ras, NeuT, c-Src and combinations thereof; and (c) classifying the prostate tumor as belonging to a tumor subclass based on the results of the detecting step.

In an aspect, the present invention provides a method of stratifying a subject having a cancer tumor, including a prostate tumor, for a clinical trial, the method comprising: (a) providing a sample derived from a subject having the cancer tumor or the prostate tumor; (b) detecting a molecular genetic signature derived from gene expression pattern or activity of one or more of a set of genes in the sample, wherein the genes are selected from the group consisting of c-Myc, Ha-Ras, NeuT, c-Src, ErbB2 and combinations thereof; and (c) stratifying the subject for a clinical trial based on the results of the detecting step.

In some embodiments subjects are stratified into subcategories that are based on the presence of a molecular genetic signature and/or the functional pathways linked to the molecular genetic signature.

In one embodiment the molecular genetic signature is based on a gene expression pattern or activity of one or more of a set of genes in a test sample derived from a subject having a cancer tumor, in particular prostate cancer tumor, wherein the one or more set of genes are selected from the group consisting of c-Myc, Ha-Ras, NeuT, c-Src and combinations thereof.

In another aspect, the present invention provides a method of selecting a treatment for a subject having a prostate tumor, the method comprising: (a) providing a sample derived from a subject having a prostate tumor; (b) detecting a molecular genetic signature derived from gene expression pattern or activity of one or more of a set of genes in the sample, wherein the genes are selected from the group consisting of c-Myc, Ha-Ras, NeuT, c-Src and combinations thereof; and (c) selecting a treatment based on the results of the detecting step (b). (i.e. oncogene based therapies would be given based on the onco signature in the patients tumor)

In yet another aspect, the present invention provides a non-naturally occurring cell produced by transforming a cell with one or more exogenous oncogenes, allowing the cell to divide at least once, wherein the cell is a human cell transformed by a vector containing the one or more exogenous oncogenes, wherein the one or more exogenous oncogenes are selected from the group consisting of c-Myc, Ha-Ras, NeuT, c-Src and combinations thereof. The signature could be applied to genetic material derived from the prostate cancer—i.e. in biofluids related to the prostate including prostate, urine, blood or other biospecimens. The signature may also be applied to other cancer types in particular as shown for breast cancer. In the case of the c-Myc signature the signature is seen in both prostate tumors and in the breast tumors derived from transgenic expression of c-Myc in the mammary gland of transgenic mice (FIG. 7C).

In one embodiment, the present invention includes identifying a cancer by obtaining a biological sample from a subject afflicted with prostate cancer or suspected of having prostate cancer or at risk for developing prostate cancer and determining whether genetic material from the biological sample has a genetic signature as described herein. In an embodiment, the biological sample is derived from a prostate biopsy. In another embodiment, the biological sample is derived from biofluids related to the prostate, including prostate, urine, blood or other biospecimens. In another embodiment, the method of the present invention includes massaging a prostate prior to obtaining a urine sample for genetic signature identification. In another embodiment, the method includes other fluids as described above.

New treatments require new testing regimes in animals. These studies have been limited by the lack of prostate cancer cell lines that can be implanted in immune competent animals. The immune system plays an important role in the onset and progression of human prostate cancer. To enable screening of new drugs to treat patients with prostate cancer it is necessary to develop prostate cancer cell lines that can be studied in immune competent animals, that reflect the human disease by histology, and the same type of behavior in vivo, including metastasis to the lungs and bones as occurs in human disease. The methods related to the creation of these cell lines that can be used in immune competent mice is described in the supplement 3.

Oligonucleotide sequences can be introduced into cells as is known in the art. Transfection, electroporation, fusion, liposomes, colloidal polymeric particles and viral and non-viral vectors as well as other means known in the art may be used to deliver the oligonucleotide sequences to the cell. The method of delivery selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, viral vectors, or the like. Oncogenes can be introduced into cells by transduction or transfection. Transduction can conducted using either retroviral or other viral delivery systems

EXAMPLES

Mice, Cell Culture, Chemicals and Reagents.

Experimental procedures with transgenic mice were approved by the ethics committee of Thomas Jefferson University. Mice were in the FVB strain. Mouse prostate epithelial cell culture were isolated from prostate glands of 12 week old male mice and maintained as previously described [42] and analyzed after 25 passages with at least three lines of each genotype. Transduction of cells by the retroviral expression vector encoding either c-Myc, Ha-Ras, v-Src, NeuT, in the vector pBABE-IRES-GFP, was previously described [43, 44].

Cellular Growth Assays.

Cells were seeded in 24-well-plates at a concentration of $1 \times 10^4$ cells/well, each sample in triplicate×7 days. Growing transformed cells in DMEM medium with 10% FBS, while control PEC cells were cultured in prostate epithelial primary culture medium. Harvest cells every 24 hours, suspended cells in 100 µl PBS, added an equal volume of 0.4% Trypan blue, after 5 minutes counted cells by Countess™ Autocounted Cell Counter (C10227, Invitrogen Carlsbad, Calif.).

Colony Formation in Soft Agar.

Cells ($3 \times 10^3$/ml) were seeded into 0.3% soft agar Sigma) in a suspension dish (Nalgene Nunc International, Rochester, N.Y.). Colonies were stained by 0.04% crystal violet acetate and counted under a vertical microscope after 2 weeks of incubation.

Tumor Formation Assay I $1 \times 10^6$ cells in 100 µl volume were injected subcutaneously into 7-8 weeks FVB male mice. Cell suspension we mixed with a 20% by volume BD Matrigel (BD Biosciences, Bedford, Mass.), resulting in a final cell concentration of $10^{-7}$ cells/ml. Tumor growth was measured by vernier calipers twice a week. Tumor samples were harvested after 30 days (except NeuT-induced tumors which were harvested after 16 days).

Cell Culture, Transfection, Transduction, Expression Vectors

The PEC (prostate epithelial cells) lines transformed with Ha-Ras, v-Src, and NeuT oncogenes were generated and transfected with a lentiviral vector containing the luc2 gene to generate stable bioluminescent cancer cell lines. The Luc2-tomato red expression vector was previously described (Liu, H., et al., Proc Natl Acad Sci U.S.A. 2010, 107, 18115-18120). The isogenic PEC lines were maintained in Dulbecco's modified Eagle's medium (DMEM) supplemented with 10% fetal bovine serum (FBS) and 1% penicillin-Streptomycin and cultured in 5% CO2 at 37° C.

Wound Healing Assay

Cells were grown to confluence on 12-well plates in DMEM medium containing 10% FBS. The monolayers were wounded with a P10 micropipette tip. The cells were washed immediately after scoring with PBS and serum-free DMEM was added (16). The cell migration was monitored for 20 h, and pictures were taken at 9 h, 12 h, 15 h and 20 h time points using an Axiovert 200 Zeiss microscope system. Images were analyzed using ImageJ software.

Cytokine Array Analysis

Mouse cytokine arrays spotted on nitrocellulose membrane were obtained from Raybiotech. Conditioned medium was prepared by culturing cells in serum-free DMEM for 48 hours. Membranes were then processed according to the manufacture's instructions for assessment of secreted cytokines in conditioned medium (see Katiyar, S. et al., Mol Cell Biol 2007, 27, 1356-1369).

Tumor Formation Assay II

Male nu/nu mice, 12 weeks old, were anesthetized by exposure to 3% isoflurane. Anesthetized mice received $1 \times 10^6$ cells suspended in 50 µL of Dulbecco's Phosphate Buffer Saline lacking of calcium and magnesium (DPBS) and 50 µL of BD Matrigel Membrane Basement (BD Biosciences, Bedford, Mass.) by subcutaneous injection below one dorsal flank. The injection has been performed using 27G½ needle. Tumor progression has been followed by bioluminescence measurement once a week until tumor excision using as described previously (18). Three mice at a time were monitored dorsally. Regions of interest (ROI) from displayed images were drawn around the tumor sites or the metastatic lesion and quantified using the Living Image 3.0 software. (Caliper Life Sciences). Tumor samples were harvested after 3 weeks. All experiments involving mice were carried out under the approval of Thomas Jefferson University's IACUC.

Experimental Metastasis Assay

Male FVB mice, 8 weeks old, were anesthetized by exposure to 3% isoflurane. $2 \times 10^5$ cancer cells suspended in 100 µL of DPBS were injected into the left ventricle of the heart of the mouse. Injections were performed using a 30G½ needle and a 1 mL syringe. To confirm the presence of cells in the systemic circulation, animals were imaged using IVIS LUMINA XR system (Caliper Life Sciences, Hopkinton Mass.). A successful intracardiac injection was indicated by systemic bioluminescence distributed through the animal body. Mice not properly injected were removed from the study. In order to in vivo imaging mice, animals received the substrate of luciferase, DLuciferin (Gold Biotechnology), at 15 mg/mL in PBS by intraperitoneal injection of 10 µL of Luciferin stock solution per gram of body weight (manufacturer's recommendation) and were anesthetized by exposure to 3% isoflurane. At 10-15 minutes after D-luciferin injection animals were placed inside the camera box of the IVIS Lumina XR (Caliper Life Sciences, Hopkinton Mass.) and received continuous exposure to 2.5% isoflurane. Imaging times ranges from 5 seconds (for later time points) to 5 minutes (for earlier time points), depending on the bioluminescence of metastatic lesion. Only one mouse was imaged ventrally. Results were analyzed using Living Image 3.0 software. For ex vivo BLI, D-Luciferin was diluted in PBS to final concentration of 300 µg/mL and used to soak freshly isolated organs for 2 to 3 minutes before imaging. Animal experiments were approved by the Thomas Jefferson University's IACUC.

Radiographic Analysis of Bone Metastasis and CT

Development of bone metastasis was monitored by X-ray radiography using IVIS Lumina XR (Caliper Life Sciences). Mice were anesthetized, arranged in prone position and exposed to an X-ray for 5 min. Administration of Maraviroc (antagonist of CCR5). Male FVB mice received an oral dose of Maraviroc (Selleck Chemicals LLC) of 8 mg/kg every 12 hours since 5 days before inoculation of cancer cells as well as after is injection until euthanasia. The drug was dissolved in water containing 5% DMSO and 0.5% 1N HCl. Control mice were maintained on an identical dosing schedule and received same injection of volume of vehicle.

Invasion Assay

The three-dimensional invasion assay was performed as previously reported. Briefly, 100 ml of 1.67 mg/ml Rat Tail collagen type I (BD Biosciences) was pipetted into the top chamber of a 24-well 8 mm pore transwell (Corning, Lowell, Mass.). The transwell was incubated at 37° C. overnight to allow the collagen to solidify. 30,000 cells were then seeded on the bottom of the transwell membrane and allowed to attach. Serum-free growth medium was placed into the bottom chamber, while 10 ug/ml osteopontin (R&D System), or 15 ng/ml CCL5 (R&D System), or 10% FBS was used as a chemo attractant in the medium of the upper chamber. The cells were then chemo attracted across the filter through the collagen above for three days. Cells were fixed in 4% formaldehyde, permeabilized with 0.2% Triton-X in PBS and then stained with 40 mg/ml propidium iodide (PI) for 2 h. Fluorescence was analyzed by confocal z sections (one section every 20 mm) at 10× magnification from the bottom of the filter using a Zeiss LSM 510 Meta inverted confocal microscope at the Kimmel Cancer Center Bioimaging Facilit.

Histological Analysis

Tumor samples and soft tissues were fixed in 4% paraformaldehyde (PFA, Fisher) and processed for paraffin bedding, sectioning, H&E and immunohistochemistry (IHC). Bones were fixed in 4% PFA at 4° C. for 72 h, decalcified in 0.5M EDTA (pH 8) for 7 days at 4° C., and embedded in paraffin (19). vWF staining on tumor sections was performed by the Pathology Core Facility of KCC. CK14 (Covance) PRB-155P and CK8 (clone1E8, Covance) MMS-162P staining was performed after deparaffinization and rehydration without performing the antigen retrieval treatment on bones and brains samples to distinguish basal from luminal prostate epithelial cells. TRAP (tartrate-resistant acid phosphatase) staining was performed after deparaffinization and rehydratation as directed by the manufacturer (Sigma-Aldrich) to identify active osteoclasts at the surface between metastatic lesion and compact bone (5) (20). Tetrachrome method was performed on bones to identify woven bone in the osteoblastic lesion areas (5,21). (RV202, Santa Cruz Biotechnology) staining was performed only on brain samples to discriminate sarcoma from carcinoma.

Laser Capture Microdissection and RNA Extraction

Whole brains and legs after removing skin and muscles were flash-frozen in optimal cutting temperature media (OCT compound Tissue Tek) and stored at −80° C. Tissues were sectioned on a cryostat ( ) and mounted on membrane slides NF 1.0 PEN. LCM was performed using PALM Microbeam system (Carl Zeiss) and PALM Robo v4.2 software. The frozen sections were stained with cresyl violet (LCM staining kit, Ambion). The capture was completed within 2 hours from the staining step to assure quality RNA. Tissue collected in the adhesive caps (Carl Zeiss) was directly stored at −80° C. with the cap down. Captured cells were lysed and RNA extracted as manufacturer's recommendations (RNeasy Micro Kit Qiagen). (see Bos, P. D. et al. Nature 2009, 459, 1005-1009; and Wang, W. Z. et al. BMC molecular biology 2009, 10, 69). The integrity of RNA was checked using 2100 Bioanalyzer (Agilent) by Nucleic Acids Facility at KCC. RNA quality assessment is based on the RNA Integrity Number (RIN).

Microarray Analysis Methods

Preprocessing and Differential Expression Analysis. Microarray data was preprocessed using background correction, quantile normalization, and summarization were performed on the Mouse Gene 1.0 ST gene expression microarrays using the Robust Multichip Analysis (RMA) workflow in Affymetrix Expression Console version 1.1 [Affymetrix, Inc., Santa Clara, Calif.]. Differentially expressed genes were identified for each of the four overexpressing cell lines, by performing pairwise comparisons against the Pec control cell line. These comparisons were performed using significance analysis of microarrays (SAM) with a false discovery rate cutoff of 1% and two-fold change cutoff.

Western Blot

Western blot assays were performed in PEC cells as indicated. Cells were pelleted and lysed in buffer (50 mM HEPES, pH 7.2, 150 mM NaCl, 1 mM EDTA, 1 mM EGTA, 1 mM DTT, 0.1% Tween 20) supplemented with protease inhibitor cocktail (Roche Diagnostics, Mannheim, Germany). Antibodies used for Western blot are: AR (H-280, Santa Cruz Biotechnology).

CGH Data Summary

From the CGH data, copy gains and losses were determined for metastatic Src-transformed cells recovered from brains and bones relative to oncogene transformed cell lines. Genomic copy variation regions were identified as genomic segments where all three replicate samples of the metastatic Src-transformed cell line demonstrated a gain or loss relative to the Src transformed cell line. Copy number data was summarized by plotting the frequency of gains and losses across the mouse genome.

PET Imaging:

Animal Imaging was performed according to the Institutional Animal Care and Use Committee. Flurine-18, Sodium fluoride (F-18-NaF) in isotonic solution was obtained from IBA Molecular (Ashburn, Va.). 210±9.54 µCi of F-18-NaF in 150 µl was injected through lateral tail vain to unanesthetized mice. One hour later animals were anesthetized with 1.5% sulfuring in 98.5% $O_2$ and imaged with Inveon micro-PET scanner (Siemens Hoffman estate, IL). A high spatial resolution (1 mm in full width at half maximum) and sensitivity (>10%) PET scanner on average 1.5 Million counts was obtained in 10 minute imaging. An ordered-subset expectation maximization 3-dimensional (3D) algorithm with 5 iterations and 8 subset was used for demonstration.

Statistical Analysis.

Comparisons between groups were analyzed by two-sided t-test. A difference of $P<0.05$ was considered to be statistically significant. All analyses were done with SPSS 11.5 software. Data are expressed as mean±SEM.

Microarray Analysis Methods. Preprocessing and Differential Expression Analysis.

Microarray data was preprocessed using background correction, quantile normalization, and summarization were performed on the Mouse Gene 1.0 ST gene expression microarrays using the Robust Multichip Analysis (RMA) [45] workflow in Affymetrix Expression Console version 1.1 [Affymetrix, Inc., Santa Clara, Calif.]. Differentially expressed genes were identified for each of the four over-expressing cell lines, c-Myc, NeuT, Ha-Ras, and v-Src, by performing pairwise comparisons against the PEC control cell line. These comparisons were performed using significance analysis of microarrays (SAM) with a false discovery rate cutoff of 1% and two-fold change cutoff.

Comparison with Fibroblasts and Mammary Tumors Breast Cancer Cell Lines.

Differential expression patterns of the four oncogene over-expressing cell lines were compared against a previously published dataset including oncogene-transduced fibroblasts and induced mammary tumors [46]. This dataset was generated on the Affymetrix Murine 11K microarray A and B set and contains Ha-Ras-overexpressing samples, c-Myc overexpressing samples as well as normal controls. Raw data (Affymetrix .CEL files) from Huang et al. [46] were obtained from the publications website. The .CEL files were processed using RMA with updated probeset definition from the University of Michigan custom CDF website (Entrez probesets version 12, dated Jul. 30, 2009) [47]. A total of 6143 genes from this dataset were mapped to gene symbols and used for comparative analysis. Differential expression analysis was performed to identify differentially regulated genes specific to Ras and Myc cell lines vs. the controls using SAM with an FDR cutoff of 10%. The differentially expressed genes identified in this dataset were compared against our four oncogene over-expressing cell lines.

A receiver operating characteristic (ROC) curve was used to plot the sensitivity and specificity over the range of discriminative values for PSA at diagnosis and correlation with the c-Myc signature [29-31]. For the evaluation of PSA, samples with abnormal PSA and a clinical metastasis event were considered true positives, and samples with abnormal PSA and no clinical metastasis event were considered false positives. For the evaluation of the c-Myc signature, samples with high correlation with the signature and clinical metastasis were considered true positives, and samples with low or negative correlation and a clinical metastasis event were considered false positives.

Gene signatures exclusive to each of the four oncogene-transformed prostate cancer cell lines were compared against two previously published prostate datasets. The first dataset comprises 185 samples log 2 normalized mRNA expression data was downloaded from the MSKCC prostate cancer database website (http://cbio.mskcc.org/cancergenomics/prostate/data/) [20]. Gene profiles in this MSKCC dataset were median-centered and Pearson's correlation was computed between each MSKCC sample and the log 2 fold change profile for each oncogene-specific signature. The second prostate cancer dataset, including distant metastasis samples, was previously obtained from the MSKCC Gerald Laboratory and samples were processed as described in [33]. Briefly, microarray samples were processed using the Robust Multichip Average (RMA) procedure [45] with custom CDFs dated Jul. 30, 2009 (version 12) [47].

Comparison with Clinical Characteristics of Prostate Cancer.

The expression patterns of the four oncogene over-expressing cell lines were compared against expression data for clinical traits including disease stage, grade, and recurrence, previously published by Lapointe et al. [3]. The dataset was downloaded from the publications website. This dataset contains 5153 probesets and 112 prostate cancer samples with annotations including tumor grade, tumor stage, and disease recurrence. Probeset annotations were updated using the Array Information Library Universal Navigator GPL3044 annotation file dated Jul. 9, 2009 [48]. Probetsets lacking gene symbol annotations were eliminated as well as probesets with at least 25% missing values, resulting in a total of 4232 features for 3327 unique genes. Differential expression analysis was performed for advanced stage vs. early stage, high grade vs. low grade, and recurrent vs. nonrecurrent disease, using SAM with an FDR cutoff of 25%. The differentially expressed genes identified in this dataset were compared against the four oncogene over-expressing prostate cancer cell lines. Significance in the overlap between the differentially expressed genes from the LaPointe dataset and genes in our data was evaluated using the hypergeometric test.

All upregulated genes meeting at least a twofold change cut off from the four oncogene over-expressing cell lines were investigated for their relationship to disease recurrence by using a previously published microarray dataset with clinical data for recurrence-free survival [11]. Microarray data that was processed with Affymetrix Microarray Suite v.5.0, as described in [11], and clinical data for each prostate sample were downloaded from the supplementary information section of the author's website (http://www.ordwayresearch.org/Glinsky-Supplemental12.html). Data was $\log_2$ transformed and for each of the four cell lines, and genes with multiple probesets were handled by averaging them together and scaling them to the probeset with the largest variance. Genes with variance in the lowest $50^{th}$ percentile were filtered out of the analysis. The average expression for each of the four lines over-expression signatures in the recurrence dataset was used to divide the population into the high (upper $25^{th}$ percentile) and low (lower $75^{th}$ percentile) expression group. Recurrence-free survival curves were plotted for the high and low expression populations, and significant p values were calculated using the log rank test.

Oncogene Transformed Prostate Cell Lines Convey Contact-Independent Growth.

Primary prostate epithelial cell cultures were established from the ventral prostates of FVB mice (FIG. 1A). Cells were transduced with retroviral expression vectors encoding a single distinct oncogene (c-Myc, Ha-Ras (V-12), v-Src and NeuT, an activating mutant of ErbB2). The cellular morphology of the prostate epithelial cells was altered over the four-week period (FIG. 1B). Individual colonies of oncogene-transduced cells were selected and characterized. Cellular growth assays were conducted by cell counting (FIG. 1C). A substantial growth advantage was observed in each oncogene transduced cell line compared with primary prostate epithelial cells.

Western blot analysis was conducted to examine the relative expression of each of the oncogenes used to transduce the PEC. The presence of oncogenic c-Myc, Ha-Ras, ErbB2 and v-Src was identified by Western blot. The increase in abundance of each oncogene was specific to each cell line (FIG. 2A). The relative abundance of Src was increased in each of the lines compared to primary PEC and was approximately 2-fold greater in v-Src transformed PEC compared with the other tumor cell lines (Shorter exposure, FIG. 2A). Oncogene transformation of fibroblasts or murine epithelial cells conveys contact-independent growth in solid agar. The oncogene transduced PEC lines were examined for growth in soft agar. Colony size and number were characterized for each oncogene (FIG. 2B) [27]. Non-transformed PECs failed to grow in soft agar as previously described [27]. Oncogene transduction increased the size and number of colonies (FIG. 2C, D).

Lung Metastases of Prostate Cancer Cell Lines.

Tumor formation studies were conducted in FVB mice. A subcutaneous injection of $1\times10^6$ cells resulted in tumor growth. Serial measurements were conducted by vernier calipers. Each of the prostate tumor lines grew subcutaneously in immune competent mice. Growth was sustained for c-Myc, Ha-Ras and v-Src transformed PECs (FIG. 3A). The extirpated tumors were hemorrhagic (FIG. 3B) with histological features of poorly differentiated prostate adenocarcinoma (FIG. 3C, Supplement 1). Immunostaining of tumors for Von Willebrand factor (VWF) confirmed angiogenesis and demonstrated significantly greater VWF staining in tumors induced by Ha-Ras (Supplement 2A, B). The tumor stained for CK5, AR, MUC1 and MGK (the murine homologue of PSA) (Supplement 2C). Lung metastases were characterized at autopsy by histopathological assessment as described in the Materials and Methods (FIG. 4A). The number of lung metastases derived from the primary PECs were increased in the Ha-Ras, v-Src and c-Myc sublines (FIG. 4B).

Oncogene Specific Molecular Signatures in Prostate Cancer Cell Lines.

Figure 5:
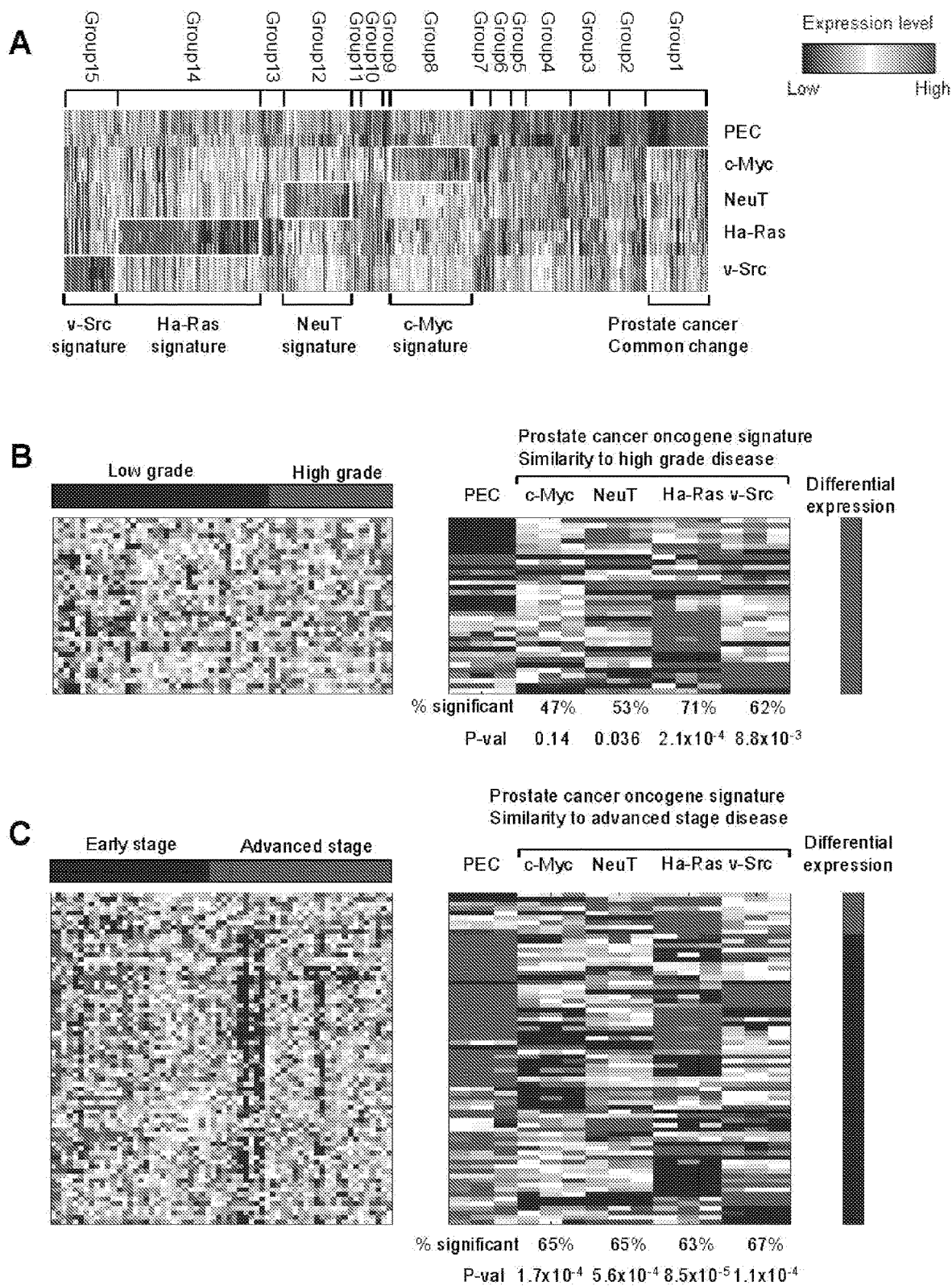
FIG. 5 illustrates hierarchical clustering of microarray gene expression.

In order to further characterize the molecular genetic signaling pathways regulated by specific oncogenes in prostate epithelial cells, mRNA was prepared from the oncogene transformed PEC cell lines. Microarray analysis identified a total of 2635 out of 22115 genes that were significantly altered in expression (at least two-fold change) in oncogene over-expressing cell lines when compared with non-transformed prostate epithelial cell control samples (FIG. 5). The heatmap of genes identified as significantly different in their expression (at least 2-fold change) is shown in FIG. 5. The rows of the heatmap represent unique genes and are displayed by their pattern of up- and down-regulation for all four of the oncogene induced cell lines A sizable number of up- and down-regulated genes were shared amongst all four cell lines (Group 1; 251 genes). For example Group 1 contains genes that share differential expression patterns across all four cell lines, while group 15 contains genes whose differential expression is specific to the Src cell lines. Genes with up and down-regulation specific to Ha-Ras were the most prevalent (Group 14; 584 genes), followed by c-Myc-specific genes (Group 8; 332 genes), NeuT-specific genes (Group 12; 277 genes), and v-Src-specific genes (Group 15; 215 genes).

The Murine Prostate Oncogene Expression Signature in High Grade and Advanced Stage Human Prostate Cancer.

Figure 6:
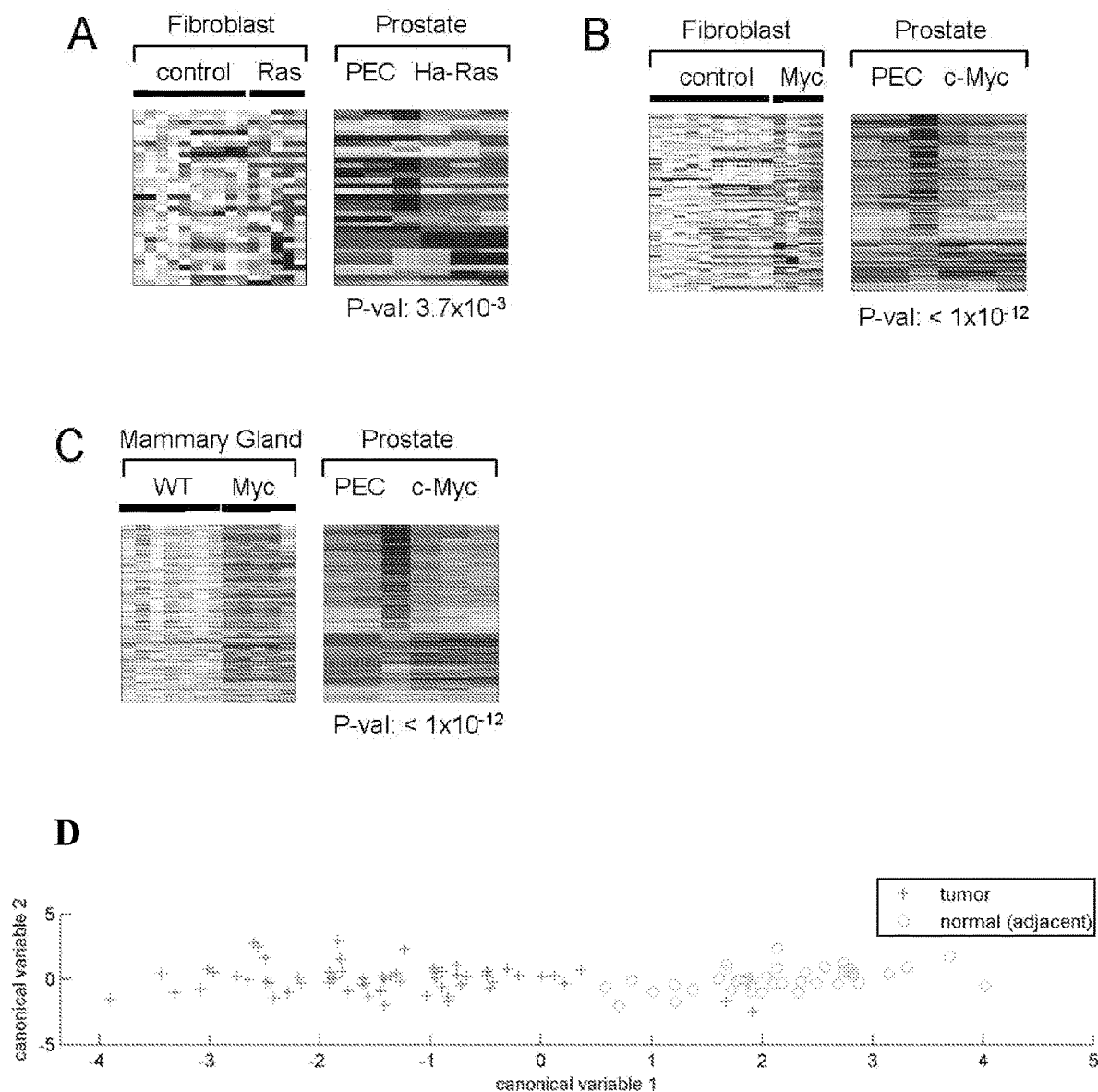
FIG. 6 illustrates c-Myc- and Ha-Ras-specific oncogene signatures in prostate tumors are conserved in other tissues.
Figure 6:
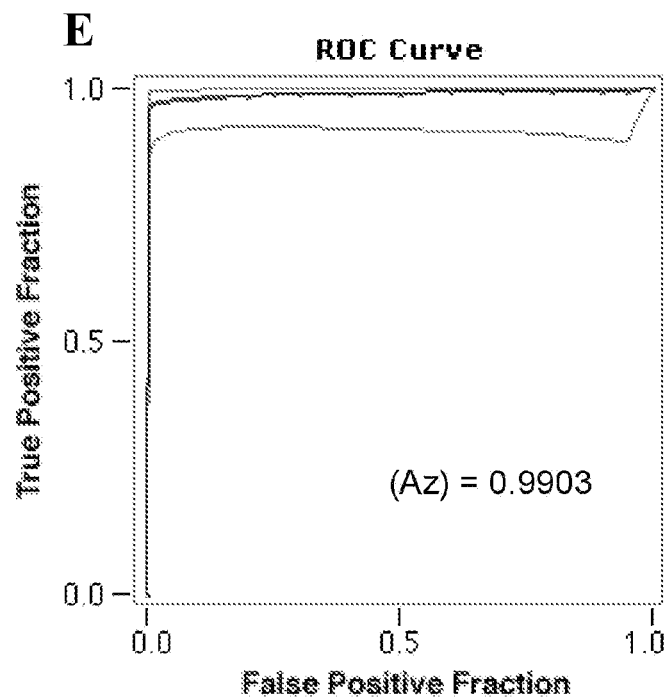
Figure 6:
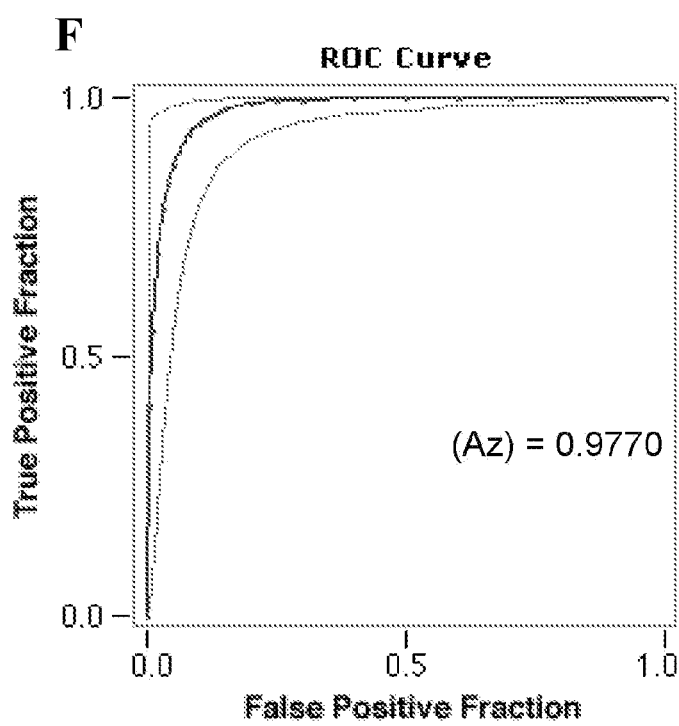
Figure 7:
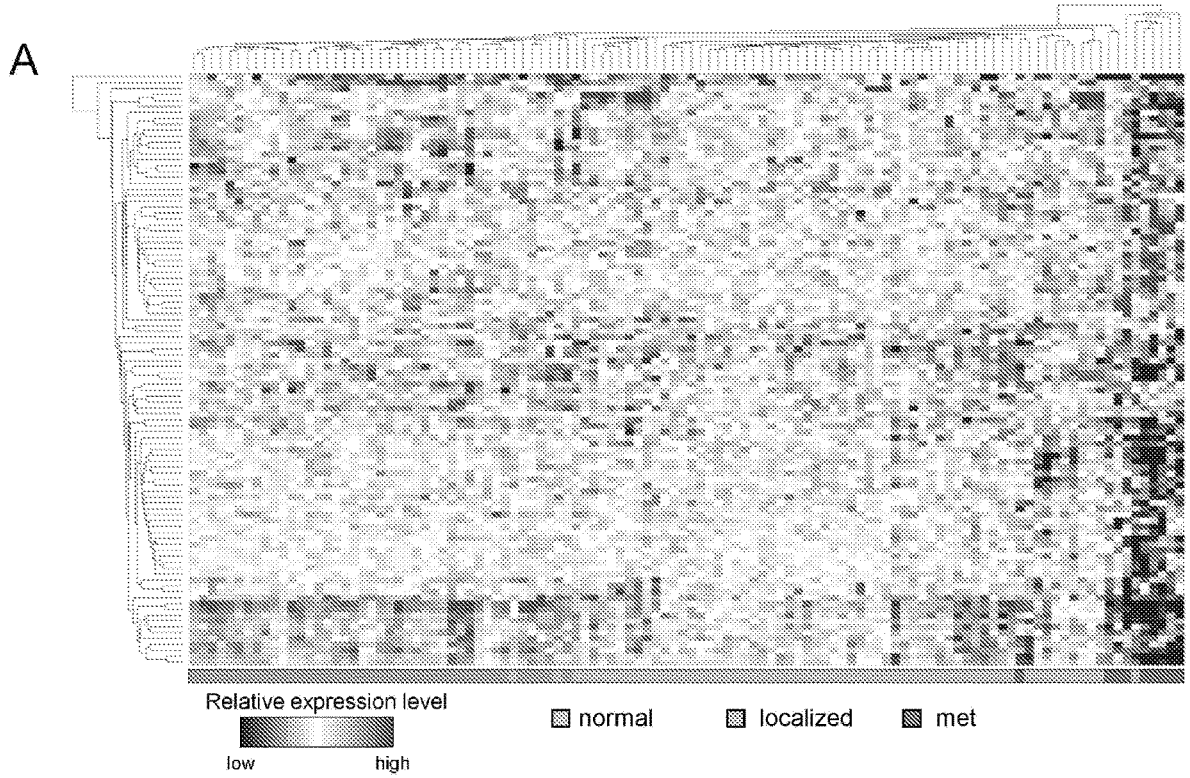
FIG. 7 illustrates gene expression correlates of oncogene transformed prostate cancer cell lines with recurrence-free survival.
Figure 7:
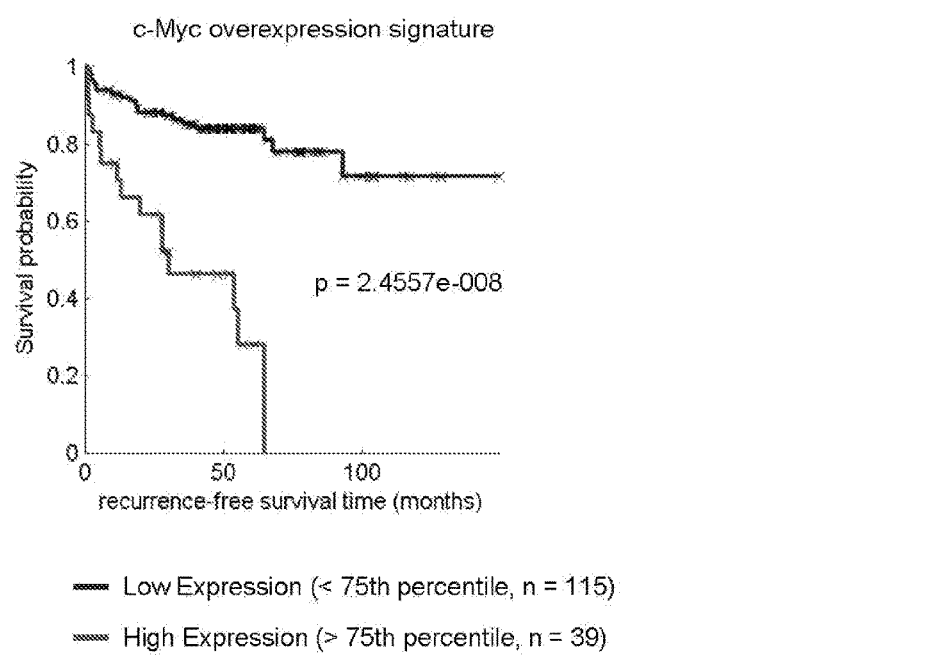
Figure 8:
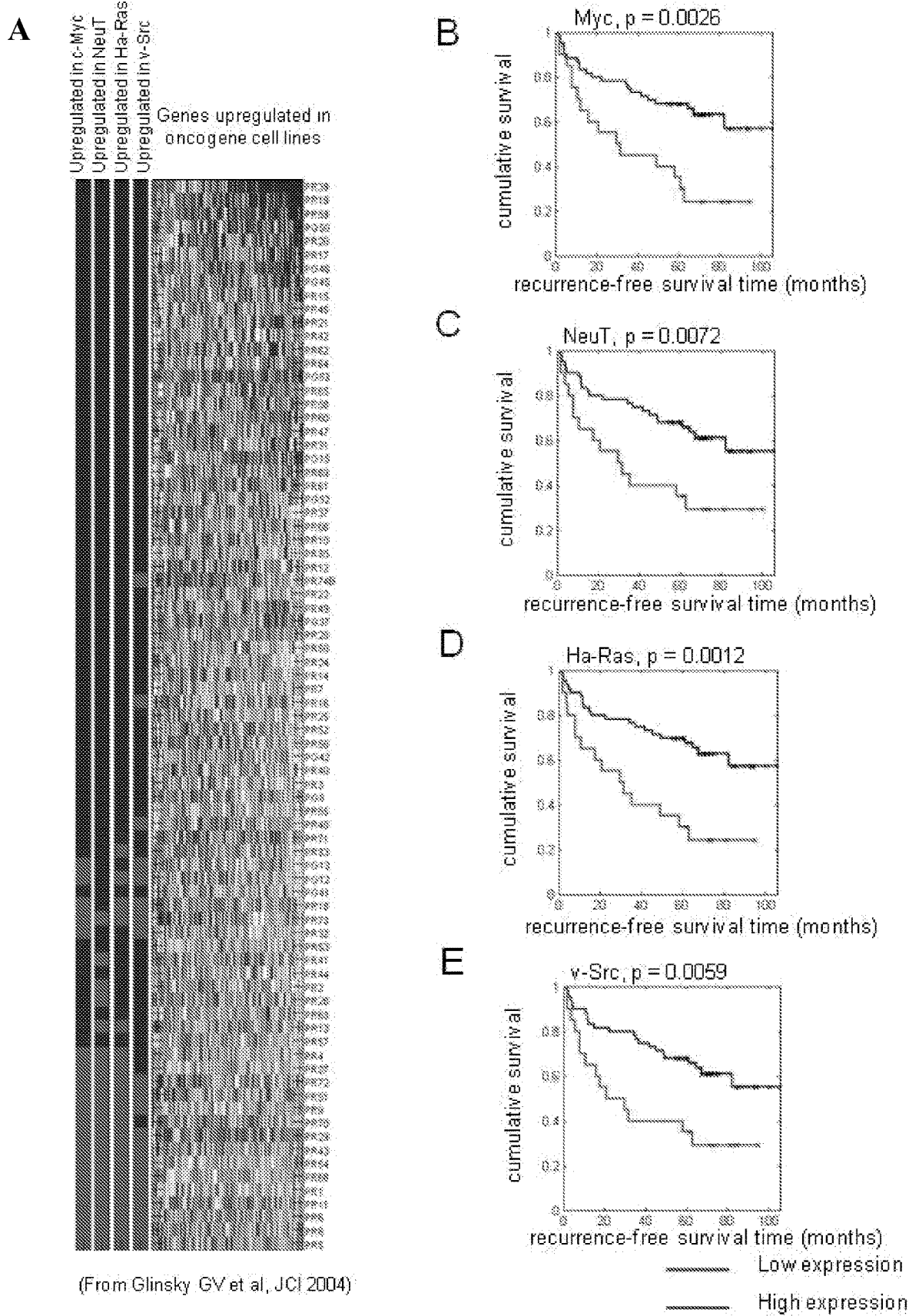
FIG. 8 illustrates gene expression correlates of oncogene transformed prostate cancer cell lines with recurrence-free survival.

The prostate "oncogene expression signature" was defined as genes that were significantly altered in expression level and that were uniquely altered in expression by a specific oncogene compared with primary prostate epithelial cells (FIG. 5). The oncogene expression signature thereby identified was compared to gene signatures obtained from other published databases to identify similarities to other well-studied disease phenotypes and cell lines. Comparisons were performed against gene signatures representative of differential expression in advanced state vs. early stage prostate cancer, high grade vs low grade prostate cancer, recurrent vs. nonrecurrent prostate cancer [3]. The gene signature heatmaps representing advanced stage/early stage, high grade/low grade, and recurrent/nonrecurrent prostate cancer phenotypes [3] (FIG. 6A,B) are shown on the left and the heatmaps on the right represent genes that are differentially expressed in the prostate oncogene expression signature. The heatmaps in FIGS. 6-8 are labeled with the percentage of genes within the "oncogene expression signature" that are differentially expressed. P values for the statistical significance of the similarity between the genes expressed in the prostate cancer cell lines and the gene signature of the disease phenotype are shown. P values are based on the hypergeometric distribution and represent the probability of these genes being differentially expressed in the disease phenotype if they were selected at random. Low p values indicate a degree of similarity between an oncogene cell line and a disease phenotype that is unlikely to occur merely by chance.

A "high grade" prostate cancer gene signature was previously determined from 61 primary prostate tumors [3]. FIG. 6A shows that 34 genes from the prostate oncogene expression signature were common to the high grade gene signature ($p=2.97\times10^{-5}$). For each oncogene induced prostate cancer cell line, the proportion of significant genes contributing to that cell line is shown. For example, the overlap between the prostate oncogene expression signature and high grade disease includes a combination of genes that are significant genes in c-Myc (47%), NeuT (53%), Ha-Ras (71%), and v-Src (62%). FIG. 6B depicts the 72 genes that were common between the prostate oncogene signature and the advanced stage gene signature ($p=4.13\times10^{-8}$). These results indicate a significant degree of similarity between the prostate oncogene expression signature and high-grade disease ($p=2.97\times10^{-5}$) and between the oncogene expression signature and the advanced stage disease phenotype ($p=4.13\times10^{-8}$).

No significant overlap was identified between the prostate oncogene expression signature and the recurrent/nonrecurrent disease signature identified by Lapointe et al. [3]. When the prostate oncogene expression signature was compared with the Lapointe data, the Ha-Ras cell line captured the highest level of similarity with high grade disease (71%), while the v-Src cell line showed the highest similarity with advanced stage disease (67%).

c-Myc Specific Gene Expression Signature in Prostate Cancer Epithelial Cells Resembles the c-Myc Signature in Fibroblasts and Mammary Tumors.

In previous studies we identified gene expression signatures that were specific to the oncogene used to transform fibroblasts (3T3 cells) that were recapitulated in mammary tumors induced by c-Myc or Ha-Ras [28]. The previously defined c-Myc and Ha-Ras induced molecular signature was compared with the gene expression signature induced by these oncogenes in the prostate cancer epithelial cells. The heatmaps in FIG. 7A depicts the genes shared between c-Myc transduced fibroblasts (FIG. 7A), c-Myc-induced mammary tumors (FIG. 7C) (left-hand heatmaps) and the c-Myc induced prostate oncogene expression signature (right-hand heatmaps). A significant overlap was identified between the prostate oncogene expression signature and the genes differentially regulated by c-Myc transduction in mouse fibroblasts (108 genes, hypergeometric $p=5.84\times10^{-12}$) or mammary tumors (363 genes; hypergeometric p=7.5916e-012). Within the prostate oncogene expression signature, c-Myc cell lines demonstrated the largest proportion of similarity with both the Myc transduced fibroblasts (92%) (FIG. 7A) and the c-Myc-induced mammary tumors (85%) (FIG. 7C).

Comparisons of the prostate oncogene expression signature against Ha-Ras transduced fibroblasts (FIG. 7B). Significant overlap was identified between the prostate oncogene expression signature and genes differentially expressed upon Ras oncogene transduction in the mouse fibroblasts (64 genes, hypergeometric $p=5.65\times10^{-9}$). Surprisingly, the Ha-Ras transformed prostate epithelial cell lines showed less commonality with the Ha-Ras transduced fibroblast signature (52%) (FIG. 7C) than the v-Src, c-Myc, and NeuT cell lines.

A Receiver Operating Characteristic (ROC) Curve (FIG. 7D) was Used to Evaluate the Discriminative Potential of PSA and the c-Myc Signature to Identify Metastatic Disease.

ROC curves have been used previously to evaluate the diagnostic ability of PSA [29, 30] as well as its ability to identify metastatic disease [31]. In the MSKCC PCa samples, the c-Myc signature ROC curve exhibited better sensitivity/specificity characteristics than PSA, as evident in the area under the ROC curves. The area under the ROC curve represents the potential of a variable to discriminate between two conditions [32], indicating that the c-Myc signature performs as a better discriminator of metastatic disease than serum PSA levels.

The c-Myc Signature Correlates with Metastatic Prostate Cancer.

All the samples were obtained from publically available prostate cancer datasets [11, 20, 33]. This comparison showed that the c-Myc signature shows a positive correlation in a subset of tumor samples that is more evident in advanced stage tumors and anticorrelated with normal prostate tissue (FIG. 7E). In contrast, the Ha-Ras and v-Src signatures are most consistently correlated with expression profiles within normal prostate tissue, and their correlation among tumor samples is more heterogeneous.

Prostate Oncogene Induced Gene Expression and Recurrence Free Survival in Human Prostate Cancer.

In order to examine the relationship between genes expressed in the oncogene transformed cell lines and survival rates from human prostate cancer, a previously published microarray dataset of human prostate tumor samples with known clinical recurrence-free survival time was used [11]. Genes in this published dataset that correspond to those upregulated in each of the four oncogene transformed prostate cancer cell lines, were used to assign the samples as high (upper $25^{th}$ percentile) or low (lower $75^{th}$ percentile). Kaplan Meier analysis was used to evaluate the difference in recurrence-free survival associated with high expression versus low expression of these genes. FIG. 8A provides a heatmap showing the expression profiles of genes in the human prostate cancer samples from the Glinsky's data set, which was upregulated in the oncogene-transformed prostate cancer cell lines. Genes that were highly expressed in each of the four prostate oncogene cell lines had a significant association with poor outcome ($p<0.005$) (FIG. 8B,E).

FIGURE LEGENDS

FIG. 1: Establishment of Oncogene Transformed Prostate Cancer Cell Lines.

(A) (I) FVB mice, (II) prostates were used to establish Primary prostate epithelial cells (PEC) as shown by phase contrast microscopy (ventral prostates of male FVB mice at 12 weeks of age). (B) Schematic representation of the methods deployed and phase contrast microscopy of oncogene induced cell lines derived from PEC transduced by distinct oncogenes (c-Myc, NeuT, Ha-Ras, v-Src). Photo of individual colonies derived from oncogene-transduced PEC that were selected and characterized. (C) Growth curves of PEC lines determined by cell counting. Data are mean±SEM of N>3 separate experiments.

Figure 2:
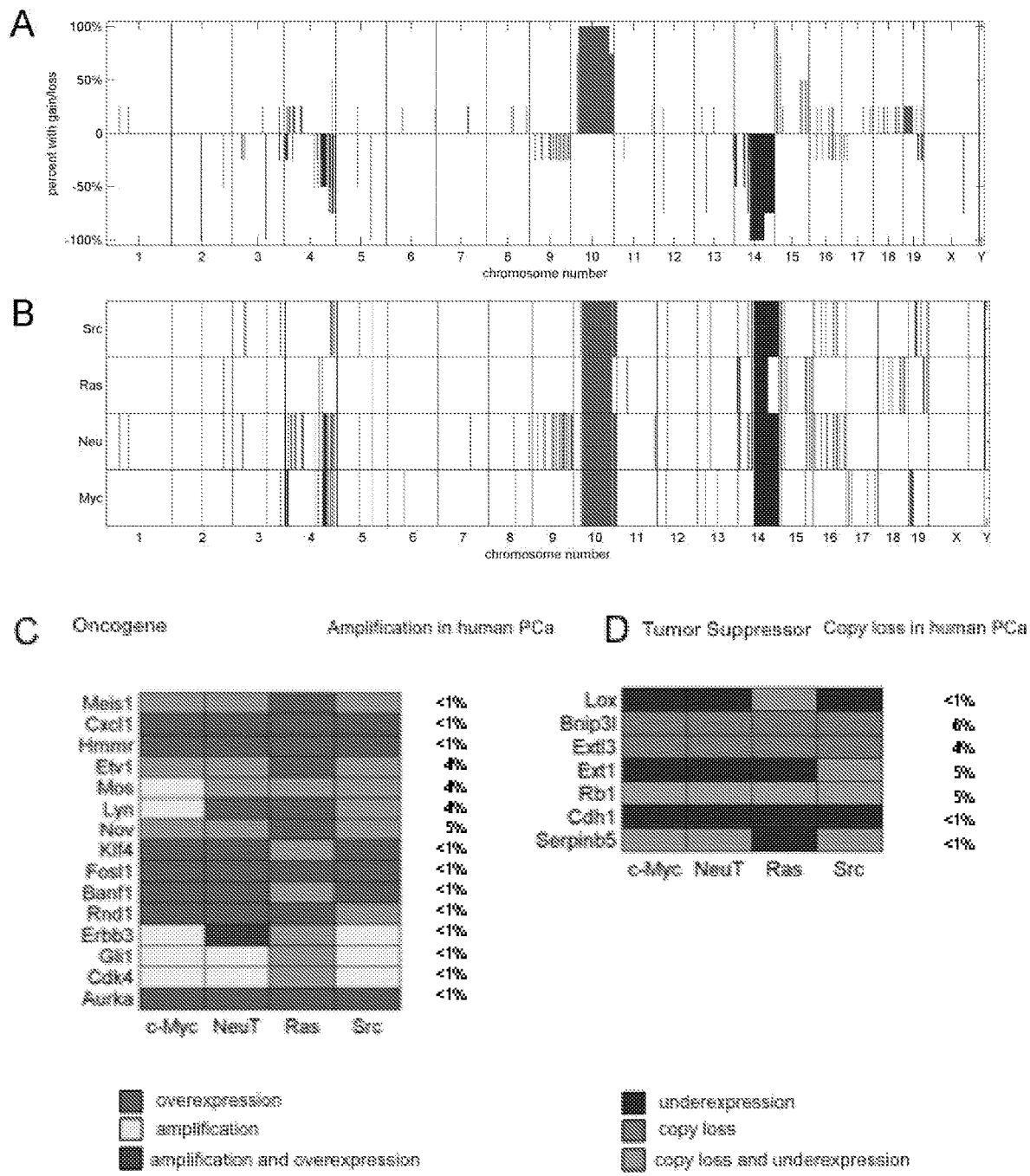
FIG. 2 illustrates copy number aberrations in the four oncogene cell lines assessed by array CGH.

FIG. 2: Oncogene Transduced PEC Lines Form Colonies in Soft Agar.

(A) Western Blot analysis of 3 separate clones of each oncogene induced PEC shows antibodies were used for the detection of c-Myc, NeuT, Ha-Ras and v-Src as shown. GDI is used as a protein loading control. (B) Soft agar assays of oncogene transduced PEC. Non-transformed PEC failed to grow in soft agar. (C), (D) The size (C) and number (D) of colonies from oncogene transduced PEC lines are shown as mean±SEM of N>5 separate experiments.

Figure 3:
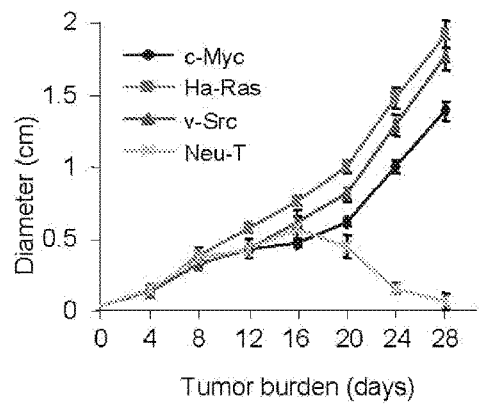
FIG. 3 illustrates prostate epithelial cell lines grow in immune competent mice.
Figure 3:
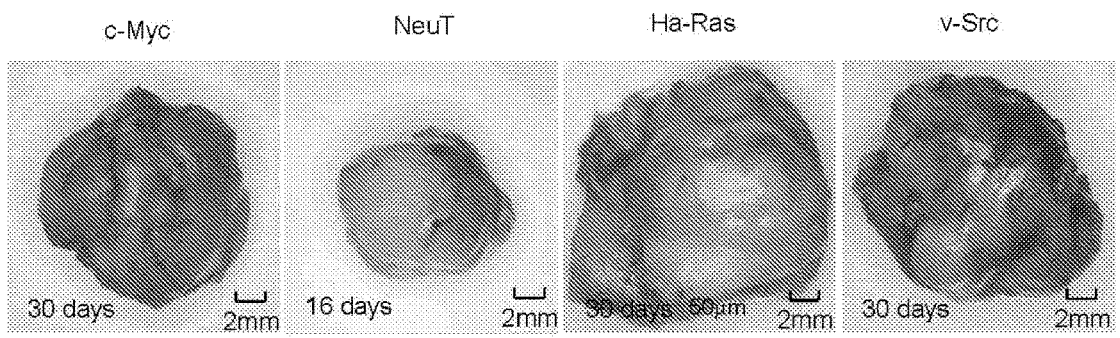
Figure 3:
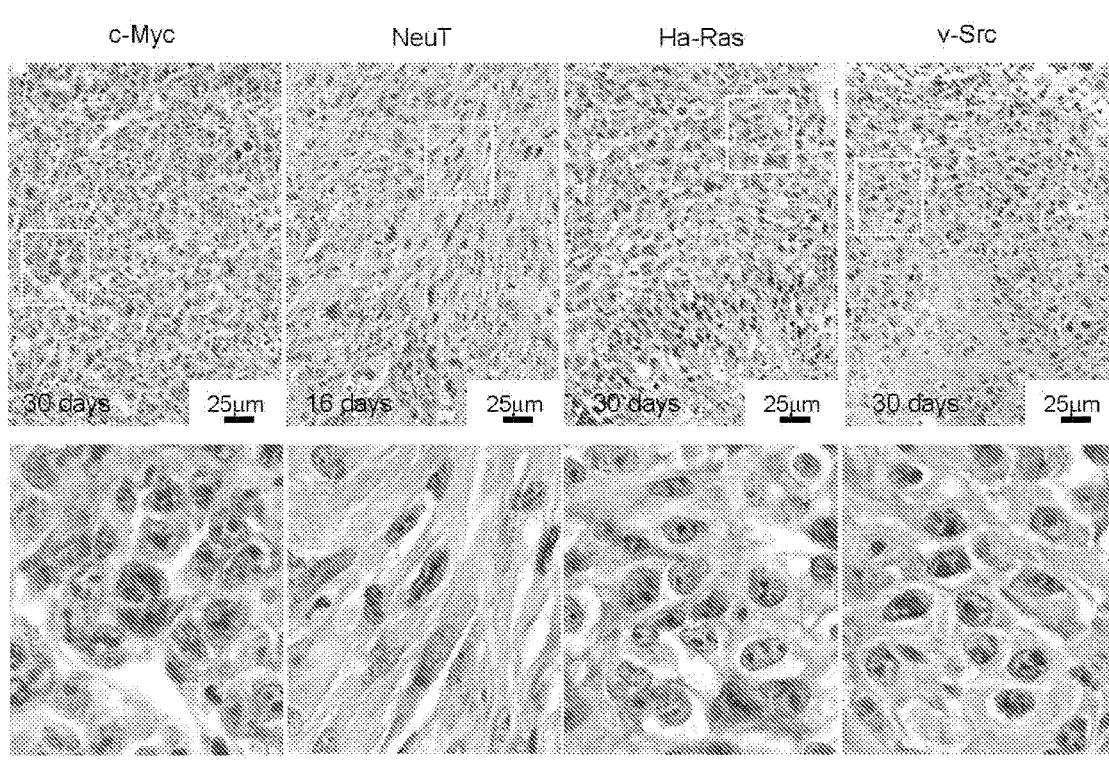

FIG. 3: Prostate Epithelial Cell Lines Grow in Immune Competent Mice.

(A) PEC tumor diameter, determined by vernier caliper measurement, is shown as days after inoculation in FVB mice. The diameter mean±SEM for N>5 separate experiments. The NeuT tumors grew for 2 weeks then decreased in size. (B) Photograph of representative tumor derived from oncogene-induced lines. NeuT induced tumors were harvested at 15 days after cell injection. (C) Hemotoxylin and eosin and (D) VWF staining of PEC demonstrates poorly differentiated prostate adenocarcinoma with local vascularity.

Figure 4:
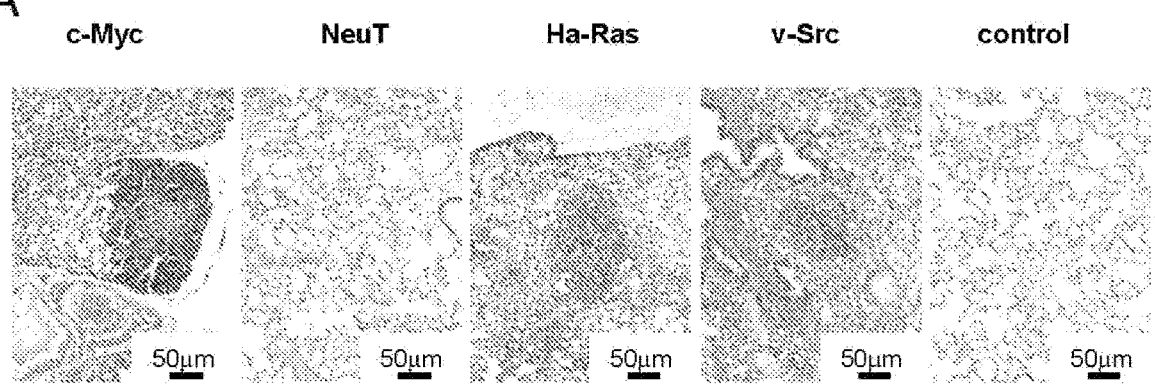
FIG. 4 illustrates oncogene transformed prostate epithelial cell tumors metastasize to lung.
Figure 4:
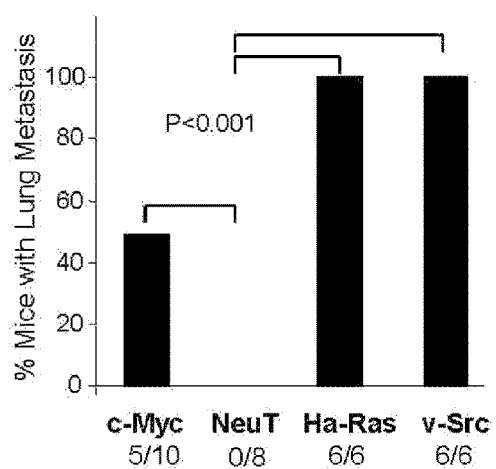

FIG. 4: Oncogene Transformed Prostate Epithelial Cell Tumors Metastasize to Lung.

(A) Hemotoxylin and eosin stain of murine lung post tumor implantation demonstrating representative example of lung metastasis. (B) Frequency of lung metastases were detected in mice for c-Myc, NeuT and v-Src PEC groups 5 weeks after subcutaneous injection. The rates were 100% frequency in Ha-Ras and v-Src groups.

FIG. 5: Hierarchical Clustering of Microarray Gene Expression.

(A) Overview of the two-way hierarchical clustering of three separate clones of four distinct oncogene transformed cell lines. Comparison is shown with primary (non-transformed) PEC. Moving average plots for the T test statistic. FVB mice injected intravenously with equal number of PEC. Differentially expressed genes are organized into patterns of up- and down-regulation in each of the four oncogene over-expressing cell lines. Data are mean±SEM of N>3 separate experiments for a total of N=30 mice.

FIG. 6: Genes Associated with High Grade and Advanced Stage Human Prostate Cancer.

Heatmaps of genes that are differentially expressed in the four oncogene transformed PEC lines and differentially expressed genes in (A) high grade vs low grade and (B) advanced stage vs early stage prostate cancer [3]. Heatmaps of the left-hand side represent the prostate cancer high grade and advanced stage signatures, while heatmaps on the right represent genes that are differentially expressed in at least one of the four prostate cancer cell lines. The percentage of these genes that are differentially expressed within each individual prostate cancer cell line is shown in the respective columns along with the p value for the degree of similarity with the high grade and advanced stage phenotypes.

FIG. 7: C-Myc and Ha-Ras Specific Oncogene Signature in Prostate Tumors is Conserved in Fibroblasts.

Heatmaps of (A) and (B) show the genes that are differentially expressed in the oncogene-induced prostate cancer cell lines and in c-Myc and Ha-Ras transduced fibroblasts (3T3 cell line) [46]. Heatmaps of the left-hand side represent the transduced fibroblasts gene signatures, while heatmaps on the right represent genes that are differentially expressed in at least one of the four prostate cancer cell lines. Heatmap of (C) shows the intersection of genes that are differentially expressed in the c-Myc prostate cancer cell line and in the respective c-Myc-induced mouse mammary tumor samples [46]. Heatmaps of the left-hand side represent the tumor sample gene signatures, while heatmaps on the right represent genes that are differentially expressed in the prostate cancer cell lines. The p values shown under each prostate cell line heatmap represent the significance of the overlap between the prostate and mammary cancer datasets. (D) ROC curve for the utility of PSA (orange) and the c-Myc signature (green) to identify metastatic disease. The x-axis represents the false positive rate (1-specificity) and the y-axis represents the true positive rate (sensitivity). The dashed line represents no discriminative ability. (E) A heatmap depicts the consistency between each of the four prostate cancer cell line signatures and samples in MSKCC prostate cancer datasets. Red indicates positive Pearson correlation, while blue indicates negative Pearson correlation.

FIG. 8: Gene Expression Correlates of Oncogene Transformed Prostate Cancer Cell Lines with Recurrence-Free Survival.

(A) Expression profile of human prostate cancer samples [11] that were upregulated in the oncogene transferred prostate cancer cell lines. Bars along the bottom of the heatmap indicate whether a sample has high (upper $25^{th}$ percentile) or low expression (lower $75^{th}$ percentile) based on genes upregulated in each of the four oncogene-transformed cell lines. Kaplan Meier curves are shown for high and low expression populations for (B) c-Myc upregulated genes, (C) NeuT upregulated genes, (D) Ha-Ras upregulated genes, (E) v-Src upregulated genes.

Supplement 2: VWF Staining.

(A) Immunohistochemical (IHC) staining of PEC tumors for VWF as a marker of neoangiogenesis. Representative example of IHC for VWF for each cell line. (B) The relative concentration of blood vessels are shown for the four oncogene induced mouse prostate tumors. Quantitation of VWF staining from oncogene-induced prostate tumors. Data are mean±SEM for N>3 separate tumors. In the NeuT group, the blood vessel concentration is lower and Ha-Ras vascularity is greater ($p<0.01$).

Supplement 3: Method for Making Oncogene Transformed Prostate Cancer Cell Lines:

(A) Mouse Prostate Epithelial Cell Culture

Medium for primary culture comprised F-12 500 ml, 10% FBS, Insulin 5 ug/ml, EGF 10 ng/ml, Hydrocortisone 1 ug/ml, transferrin 5 ng/ml, bovine pituitary extraction 30 ug/ml, 1× pen-strep, and 1× Gentamicin. Mice prostate derived from 12 weeks old FVB mice, ventral prostate, was removed, washed in PBS, the prostate tissues were chopped in a 6 cm plate for several minutes using razor blades. The chopped tissues were added in 0.5 mg/ml collagenase solution and the plates were put in 37° C., 5% CO2 incubator for 16 h. The digested tissues were washed with PBS and the resulting cells pellet resuspended using the medium, and then planted in 10 cm cell plates.

(B) Transformed the Mouse Prostate Epithelial Cells with pBABE-IRES-cMyc, pBABE-IRES-NeuT, pBABE-IRES-h-RAS, pBABE-IRES-vSrc Plasmids pBABE-IRES-target gene was transfected into 293T cells by calcium phosphate precipitation. DNA and CaCl2 were mixed in HBS buffer, and the mixture made up to a final volume of 1 ml, which was allowed to stand for 20 mins at RT. This mixture was then mixed into 293T cells and the cells put into incubator for 5 hours then the incubation medium was removed and replace with fresh medium. After 48 hours, the supernatant of 293T cells was collected, mixed with equal volume of fresh medium, and the resulting mixture was filtered by 0.45 um filter. Polybrene (final concentration 8 ug/ml) was then added into the mixture, which was then added into prostate epithelial cells which were in passage one. After another 48 hours of infection, the medium was removed and replace with fresh medium (DMEM, 10% FBS).

(C) Selected Positive Clones

To a culture medium comprised DMEM, 10% FBS, and 1× pen-strep. was added puromysin, and the final concentration was made up to 1~2 ug/ml. The cells were repeatedly treated with puromysin for at least 1 month, until the negative cells were dead, and the positive clones with oncogene expression were left. When the clones were big enough, picked the clones by were picked by cloning cylinders (Specialty Media, cat #TR-1004), and the cells were appropriately marked. The cells were then grown for at least 25 passages. Characterized in assays of growth in tissue culture soft agar, in vivo implantation, metastasis, microarray and histopathology.

FIG. 1 illustrates oncogene transduced PEC lines form colonies in soft agar. FIG. 1A illustrates phase contrast microscopy of oncogene induced cell lines were transduced by distinct oncogenes (c-Myc, NeuT, Ha-Ras, v-Src). Photo of individual colonies derived from oncogene-transduced PEC that were selected and characterized. FIG. 1B illustrates growth curves of PEC lines determined by cell counting. Data are mean±SEM of N>3 separate experiments. FIGS. 1C and 1D describe Western Blot analysis of 3 separate clones of each oncogene induced PEC with antibodies as shown for detection of c-Myc, NeuT, Ha-Ras and v-Src and FIG. 1D describes markers of basal (CK5) vs luminal (CK8) prostate cancer. GDI is used as a protein loading control. FIG. 1E describes soft agar assays of oncogene transduced PEC. Non-transformed PEC failed to grow in soft agar. The size (FIG. 1E) and number (FIG. 1F) of colonies from oncogene transduced PEC lines are shown as mean±SEM of N>5 separate experiments.

FIG. 2 depicts copy number aberrations in the four oncogene cell lines assessed by array CGH. FIG. 2A illustrates the percentage of the four cell lines sharing copy gain or loss regions is shown as a function of genomic position. FIG. 2B illustrates regions of copy gain (red) or loss (blue) for each of the four cell lines are shown as a function of genomic position. In FIG. 2C oncogenes are identified with mRNA overexpression (red), DNA amplification (yellow), or both (purple) among the four oncogene cell lines, with corresponding amplification in the MKSCC prostate cancer database (listed on righthand side). In FIG. 2D, tumor suppressor genes are identified with mRNA underexpression (blue), DNA copy loss (pink), or both (orange) among the four oncogene cell lines, with corresponding copy loss in the MKSCC prostate cancer database (listed on right-hand side).

FIG. 3 illustrates prostate epithelial cell lines grow in immune competent mice.

In FIG. 3A PEC tumor diameter determined by vernier caliper measurement is shown as days after inoculation in FVB 30 mice. The diameter mean±SEM for N>5 separate experiments. FIG. 3B shows photograph of representative tumor derived from oncogene-induced lines. NeuT induced tumors were harvested at 15 days after cell injection. FIG. 3C shows Hematoxylin and eosin staining at low and high magnification (see also supplemental data 1-4).

FIG. 4 shows oncogene transformed prostate epithelial cell tumors metastasize to lung. FIG. 4A shows Hematoxylin and eosin stain of murine lung post tumor implantation demonstrating representative example of lung metastasis. FIG. 4B shows Frequency of lung metastases were detected in mice for c-Myc, NeuT and v-Src PEC groups 5 weeks after subcutaneous injection. The rates were 100% frequency in Ha-Ras and v-Src groups.

FIG. 5 shows hierarchical clustering of microarray gene expression. FIG. 5A shows an overview of the two-way hierarchical clustering of three separate clones of four distinct oncogene transformed cell lines. Comparison is shown with primary (non-transformed) PEC. Differentially expressed genes are organized into patterns of up- and down-regulation in each of the four oncogene overexpressing cell lines. Data are mean±SEM of N>3 separate experiments for a total of N=30 mice. Heatmaps of genes that are differentially expressed in the four oncogene transformed PEC lines and differentially expressed genes in (FIG. 5B) high grade vs low grade and (FIG. 5C) advanced stage vs early stage prostate cancer (8). Heatmaps of the left-hand side represent the prostate cancer high grade and advanced stage signatures, while heatmaps on the right represent genes that are differentially expressed in the four prostate cancer cell lines. The percentage of these genes that are differentially expressed within each individual prostate cancer cell line is shown in the respective columns along with the p value for the degree of similarity with the high grade and advanced stage phenotypes.

FIG. 6 shows c-Myc- and Ha-Ras-specific oncogene signatures in prostate tumors are conserved in other tissues. Heatmaps show genes that are differentially expressed in the oncogene-induced prostate cancer cell lines and in FIG. 6A Ha-Ras and FIG. 6B c-Myc fibroblasts (3T3 cell line). In FIG. 6C A heatmap shows the intersection of genes that are differentially expressed in the c-Myc prostate cancer cell line and mouse mammary tumor samples. The p values shown under each prostate cell line heatmap represent the significance of the overlap between the prostate and fibroblast/mammary tumor signatures. FIG. 6D shows a classifier based on canonical analysis of c-Myc signature distinguishes human tumor (red) from normal tissue (light blue), along the x-axis, in the Lapointe 2004 dataset. ROC curves for the classifier performance are shown for E) the Lapointe 2004 dataset and F) the Taylor 2010 MSKCC dataset, with AUC values of 0.990 and 0.977, respectively.

FIG. 7 shows gene expression correlates of oncogene transformed prostate cancer cell lines with recurrence-free survival. FIG. 7A shows expression profile of human prostate cancer samples (13) that were upregulated in the oncogene transferred prostate cancer cell lines. Bars along the bottom of the heatmap indicate whether a sample has high (upper 25th percentile) or low expression (lower 75th percentile) based on genes upregulated in each of the four oncogene transformed cell lines. Kaplan Meier curves are shown for high and low expression populations for (FIG. 7B) c-Myc upregulated genes.

FIG. 8 illustrates gene expression correlates of oncogene transformed prostate cancer cell lines with recurrence-free survival.

Figure 9:
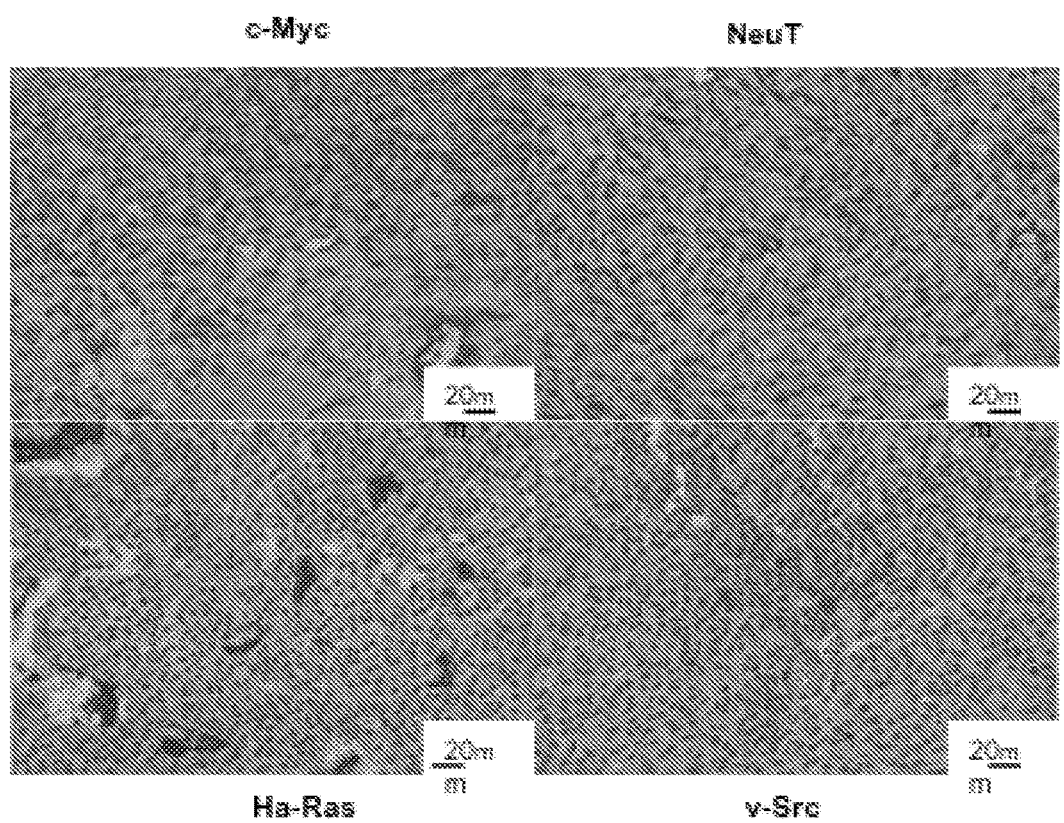
FIG. 9 illustrates histological features of poorly differentiated prostate adenocarcinoma.
Figure 9:
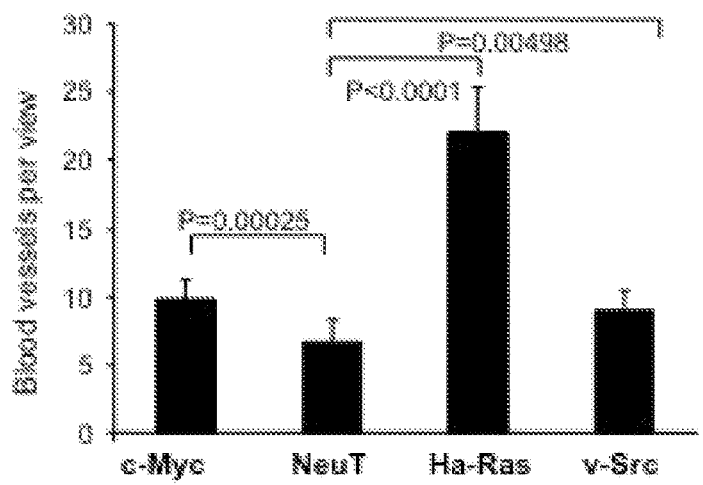

FIG. 9 illustrates histological features of poorly differentiated prostate adenocarcinoma.

FIGS. 10A-10D demonstrate that Src enhances 3D matrigel invasion of isogenic prostate cancer cell lines. The isogenic prostate cancer cell lines were derived from transduction of murine epithelial and prostate epithelial cells in retro viruses encoding either oncogenic NeuT, Ha-Ras, or c-Src. As shown in FIG. 10A, these cells conveyed the ability to migrate into a wound with the NeuT line, conveying the most rapid wound closure. While FIG. 10A illustrates wounding assay of cellular migration showing wound, FIG. 10B illustrates quantitation of closure for N=3 separate experiments. FIG. 10C illustrates 3-D invasion assay using prostate cancer cell lines in matrigel. FIG. 10D shows mean distances of invasion±SEM from 3 independent experiments for PEC lines (PEC-NeuT, PEC-Ras, and PEC-Src). As shown in FIGS. 10C and 10D, invasion into matrigel was more efficient for the c-Src transduced line. Statistical analysis of the results shown was conducted using the Student's t test.

Figure 11A:
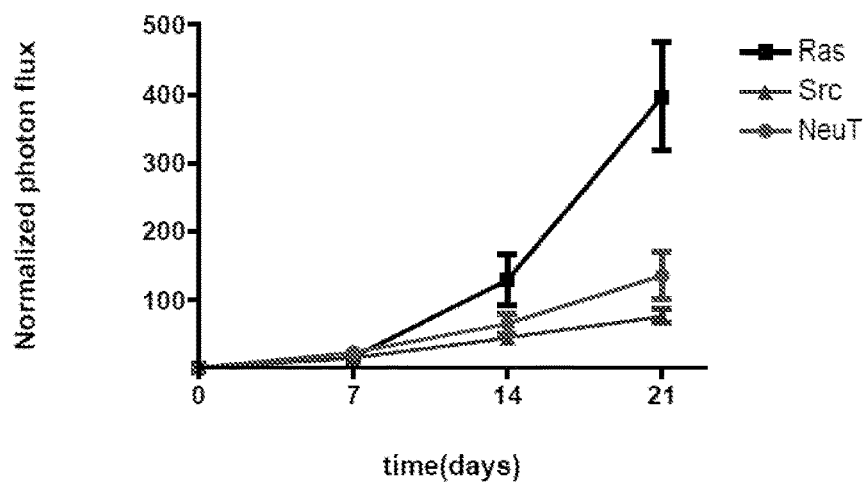
FIG. 11A illustrates subcutaneous tumor growth in NCR nude mice, quantitated over 3 weeks following subcutaneous innoculation of $1\times10^5$ cells for each of the 3 lines using normalized photon flux to quantitate tumor volume.
Figure 11B:
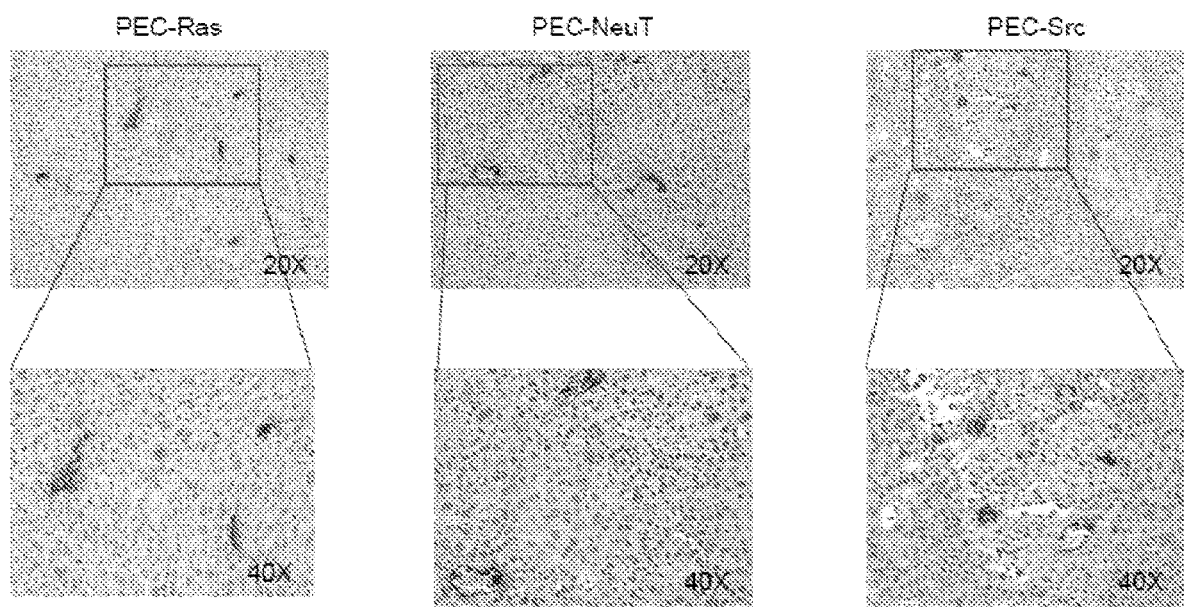
FIG. 11B illustrates immunohistochemical staining for von Willebrand factor (WF) showing vascularity of the lines with enhanced VWF staining of the Ras line.

FIGS. 11A and 11B demonstrate isogenic prostate cancer cell line tumors are vascular. In FIG. 11A subcutaneous tumor growth in NCR nude mice was quantitated over 3 weeks following subcutaneous innoculation of $1 \times 10^5$ cells for each of the 3 lines (PEC-NeuT, PEC-Ras, and PEC-Src) using normalized photon flux to quantitate tumor volume. Mean sizes±SEM from 3 independent experiments for PEC lines are shown. Associated with enhanced Src kinase activity, the lines grew as subcutaneous tumors in NCR nude mice; the relative size as determined by photon flux suggested more rapid growth amongst the Ras-derived lines Statistical analysis of the data was conducted using the Student's t test.

In FIG. 11B, immunohistochemical staining for von Willebrand factor (WF) showed vascularity of the lines with enhanced VWF staining of the Ras line. In other words, the enhanced tumor growth rate of the Ras line was associated with increased angiogenesis, as evidenced by increased von Willebrand factor, (VWF) staining.

Figure 12A:
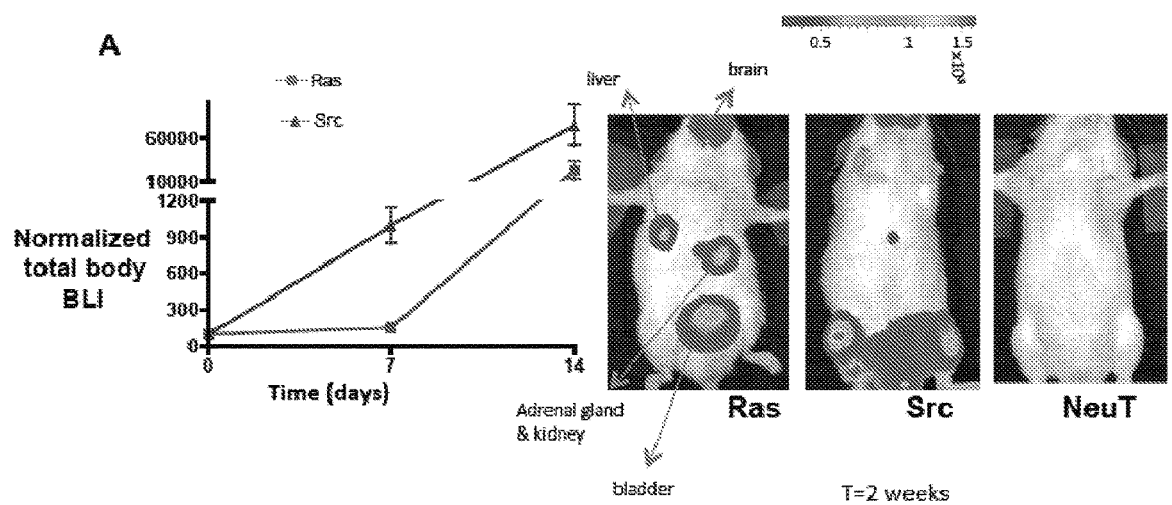
FIG. 12A illustrates representative total body bioluminescence images of at two weeks after intracardiac injection of prostate epithelial cells.

FIGS. 12A-12E demonstrate prostate cancer lines develop metastasis. Tomato-Red. Cells were injected into the left cardiac ventricle of 16 mice for each cell line. Bioluminescence images were acquired and quantified 14 days after xenografting. Representative in vivo images of mice are shown in FIG. 12A. As shown, upon introduction of tumors into the arterial circulation via the left ventricle of the heart (I.C. Injection), tumors developed rapidly in multiple organs, including liver, brain, bladder, adrenal gland and kidney, within two weeks of injection.

Figures 12B, 12C, 12D:
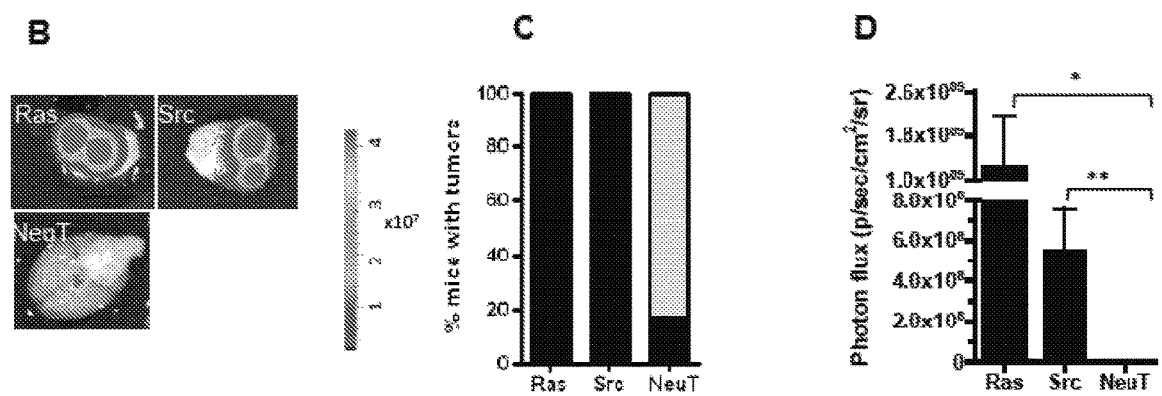
FIG. 12B illustrates representative images of brain metastasis in mice following intracardiac injection of the isogenic prostate cancer lines.
FIG. 12C illustrates quantification (mean±SEM, n=6) of Bioluminescence Imaging (BLI) shown as proportion of mice with tumors.
FIG. 12D illustrates mean total proton flux as a measure of metastatic brain tumor burden for each of the isogenic lines.

FIG. 12B shows representative images of brain metastasis in mice following the intracardiac injection of the isogenic prostate cancer lines. FIG. 12C shows quantification (mean±SEM, n=6) of Bioluminescence Imaging (BLI) as proportion of mice with tumors. (Statistical comparison was performed using Student's t test with Welch's correction for heterogeneous variances)

FIG. 12D shows mean total proton flux as a measure of metastatic brain tumor burden for each of the isogenic lines (data are mean±SEM, n=5).

Figure 12E:
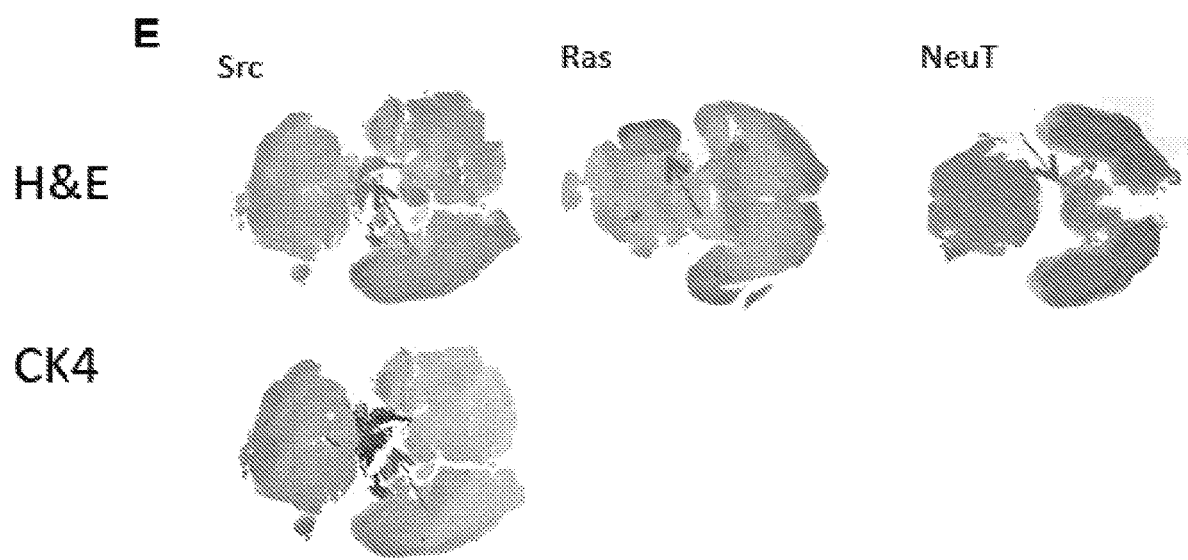
FIG. 12E illustrates Haematoxylin Eosin ("H&E") staining of brain metastasis formed after 2 weeks of PEC-Src and PEC-NeuT intracardiac injection and Cytokeartin 14 ("CK14") staining corroborating the presence of prostate epithelial cells within the brain.

FIG. 12E shows H&E staining of brain metastasis formed after 2 weeks of PEC-Src and PEC-NeuT intracardiac injection. Also, CK14 staining corroborated the presence of prostate epithelial cells within the brain (arrow).

Photonic emission evidenced metastasis in the brains of mice injected with the Ras and Src prostate cancer cell lines. Less frequent metastasis occurred to the brains of mice injected with the NeuT lines. The relative frequency of metastasis amongst the mice demonstrated 100% of the Ha-Ras and Src lines developed tumors in mice, and the relative tumor burden was $1 \times 10^9$ for Ras, $5 \times 10^8$ in c-Src, with $1 \times 10^4$ for NeuT. As shown in FIG. 3E, histological analysis of the brain metastasis of the mice injected with the Ras or Src PEC lines showed the primary histology was adenocarcinoma.

Figure 13A:
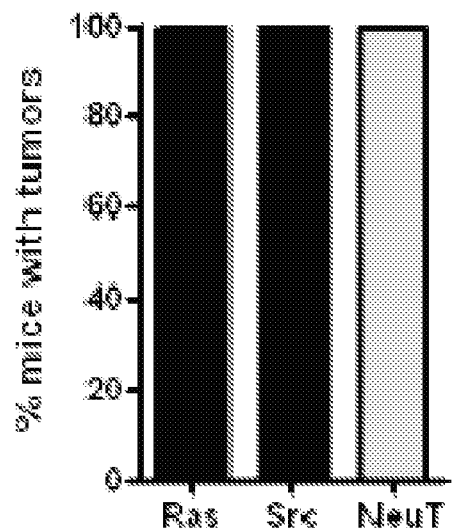
FIG. 13A illustrates the percentage of mice with liver tumors.
Figure 13B:
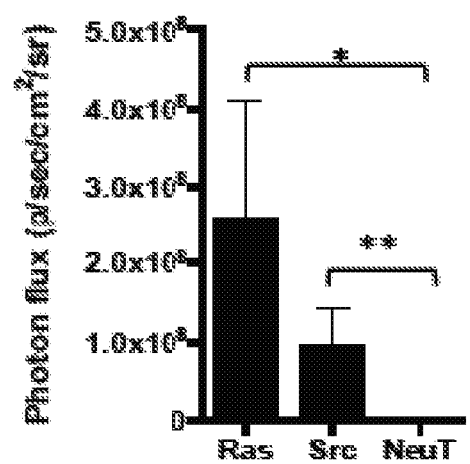
FIG. 13B illustrates the tumor size determined by photonflux.
Figure 13C:
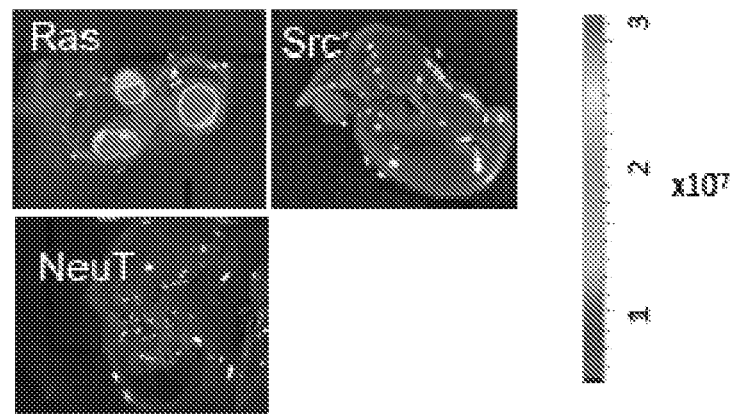
FIG. 13C illustrates representative mice images showing liver metastasis.

FIGS. 13A-13C demonstrate liver metastasis of prostate tumor cell lines. Isogenic PEC lines expressing the Luc2-Tomato-Red fusion protein were injected into the ventricle of FVB mice and the in vivo bioluminescent signal quantified. FIG. 12A illustrates the percentage of mice with liver tumors. Hepatic metastasis in the mice injected with the Ras and Src PEC lines developed liver metastasis (~100% of the animals). Although the NeuT tumors grew subcutaneously, none developed liver metastasis. FIG. 12B illustrates the tumor size determined by photonflux and FIG. 13C illustrates representative mice images showing liver metastasis.

Kidney metastasis were identified in the mice injected with the Ras and Src derived lines. FIG. 13D illustrates the percentage of mice with kidney tumors. FIG. 13E illustrates size of kidney tumors by photon flux and FIG. 13F illustrates representative images of kidney metastasis.

Figure 14A:
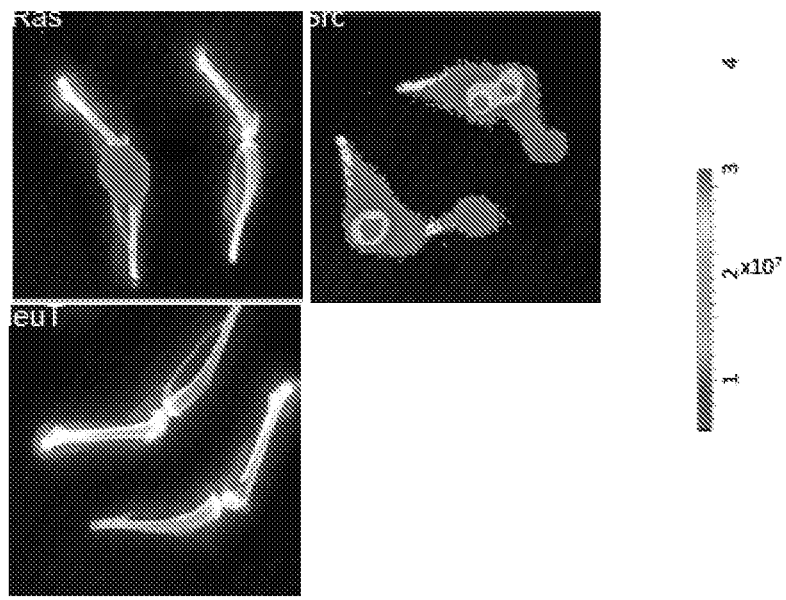
FIG. 14A illustrates representative in vivo images of FVB mice that underwent intracardiac injection of PEC lines expressing Luc2-Tomato-Red fusion protein and the in vivo bioluminescent signal was quantified.
Figure 14B:
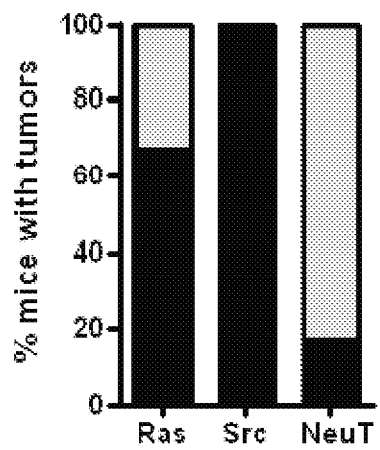
FIG. 14B illustrates quantification (mean±SEM, n=6) of Bioluminescence Imaging (BLI) as proportion of mice with tumors.
Figure 14C:
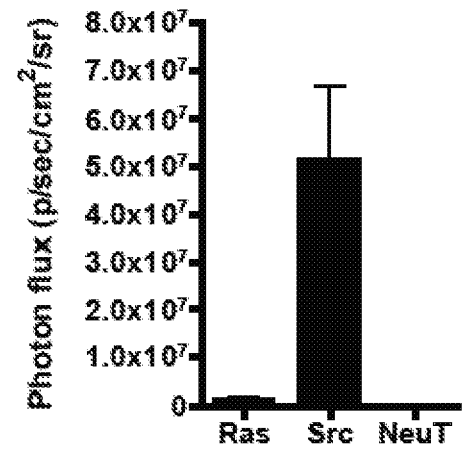
FIG. 14C illustrates size of tumor mass on photon flux.

FIGS. 14A-14C demonstrate isogenic prostate cancer cell lines develop osteolytic bone metastases. FIG. 14A illustrates representative in vivo images of FVB mice that underwent intracardiac injection of PEC lines expressing Luc2-Tomato-Red fusion protein and the in vivo bioluminescent signal was quantified.

As shown in FIG. 14A, the bony metastasis of the mice were osteolytic in nature. FIG. 14B shows quantification (mean±SEM, n=6) of BLI as proportion of mice with tumors. As illustrated, 100% of the mice injected with the c-Src tumors developed bony metastasis, 65% amongst the Ha-Ras, and 15% amongst NeuT. The bony photon flux was dramatically enhanced in the c-Src tumors, with total photon flux $5 \times 10^7$ vs. Ha-Ras $1 \times 10^6$ and NeuT $1 \times 10^4$. FIG. 14C illustrates the size of-tumor mass on photon flux. Histological analysis of the osteolytic bone lesions of the prostate tumors evidenced, adenocarcinoma resembling the primary tumor.

FIGS. 15A-15F demonstrate Src enhances osteolytic prostate cancer bone metastases. FVB mice 2 weeks after PEC-Src intracardiac injection developed osteolytic bone lesions. FIG. 15A shows tumor area in bones was significantly increased in the PEC-Src group compared with PEC-Ras and PEC-NeuT. The area of the tumor was six-fold greater in c-Src compared to Ras driven tumors.

FIG. 15B illustrates representative X-Rays before (t0) and 14d (t14) after intracardiac injection of cells. Low density areas colocalized with the metastatic tumors (arrowhead) indicating osteolytic lesions. The bone lesions were found primarily at the epiphyseal junction as osteolytic lesions at two weeks.

Hisological analysis confirmed adenocarcinoma at the site of bony metastasis. Tartrate resistant acid phosphatase ("TRAP") staining, shown in FIG. 15C, corroborated the presence of osteoblast (arrows) in the bone-tumor interface. FIG. 15D shows Haematoxylin Eosin ("H&E") staining of bone metastasis formed after. FIGS. 15E and 15F, show cytokeratin (CK) 14 staining and CK8 staining respectively, both corroborating the presence of epithelial cells within bone.

Figures 16A, 16B, 16C:
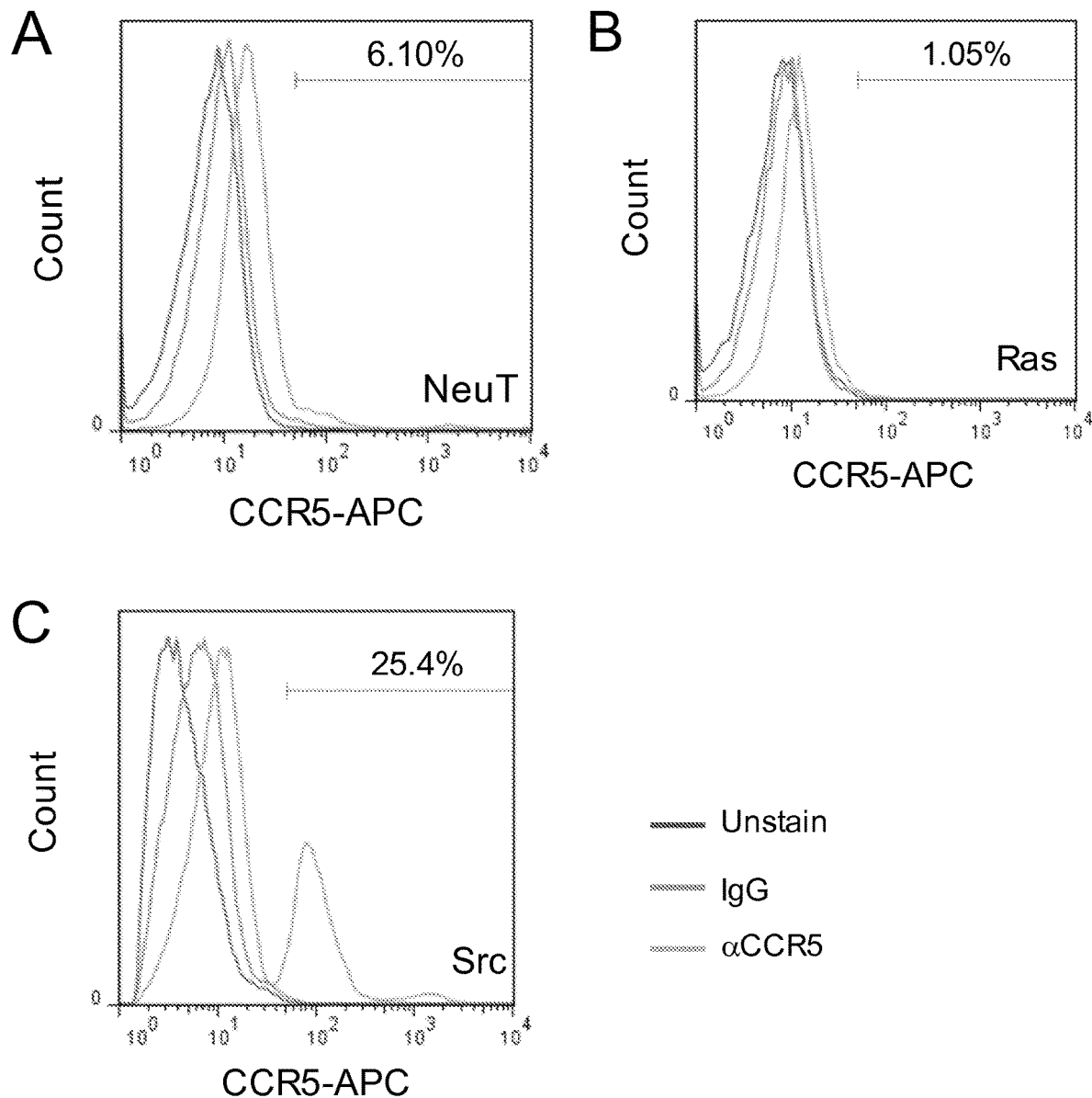
FIGS. 16A-16C illustrate fluorescence activated cell sorter ("FACS") analysis of CCR5 expression on PEC lines.

FIGS. 16A-16G demonstrate osteolytic prostate cancer cell lines express function CCL5 and osteopontin ("OPN") receptors. FIGS. 16A-16C show Fluorescence-Activated Cell Sorting ("FACS") analysis of CCR5 expression on PEC lines. As shown, FACS analysis using a CCR5 specific antibody confirmed the presence of the CCR5 receptor in PEC lines.

Figure 16G:
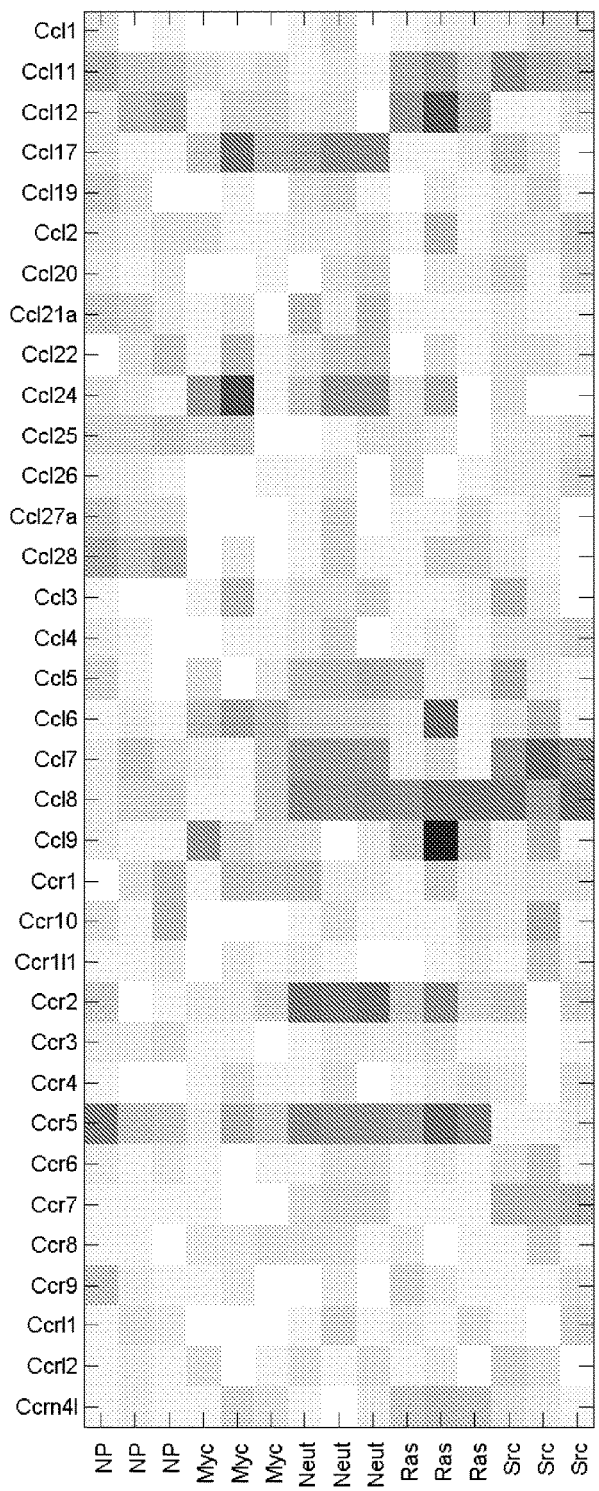
FIG. 16G illustrates relative abundance of cytokine ligands and receptors after subcutaneous implantation compared with expression in tissue culture.
Figure 16H:
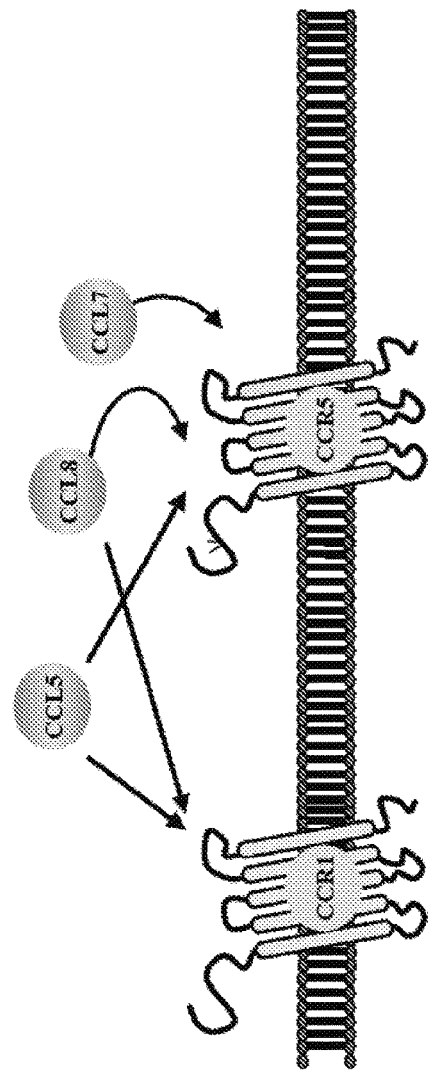
FIG. 16H illustrates that CCL7, CCL8 and CCL5 are ligands for CCR5, and CCL8 and CCL5 are ligands for for CCR1.

FIG. 16D shows results of Matrigel invasion assays of the PEC-Src line conducted using OPN as CD44 ligand and CCL5 as CCR5 ligand and quantified as mean±SEM (FIG. 16E). As shown in FIGS. 16D and 16E, the addition of OPN or CCR5 enhanced PEC invasiveness into matrigel. For the comparison to tissue, the in vivo tumor gene expression in the oncogene transformed PEC was compared with the expression in vivo in the dorsolateral ventral prostate of mice with the same strain. FIG. 16F shows chemokine receptor and ligand gene expression of prostate tumor cell lines in tissue culture. And FIG. 16G shows chemokine receptor and ligand gene expression of prostate tumor cell lines after subcutaneous implantation. The gene expression showed a notable up regulation in vivo of the cytokine and chemokines. Specifically upregulation of CCR5 and CCR2 was observed in the c-Myc, NeuT and Src PEC lines. Upregulation of the receptor ligands CCL2, CCL7, and CCL8 was observed (2- to 3-fold). CCL7, CCL8 and CCL5 are ligands for CCR5, CCL8 and CCL5 for CCR1 (FIG. 16H). These studies indicate the induction of cytokine receptor and ligand expression in PEC tumors in vivo compared with tissue culture marked in red square.

Therefore, the microarray based gene expression profiling showed activation of a CCR5 signaling module when the PEC lines were grown in vivo vs tissue culture.

CCL2 binds CCR2 and CCR4. Given that CCR5 and its ligands CCL5, CCL7 and CCL8 were induced in the PEC in vivo, the effect of the CCR5 antagonist on prostate tumor growth was examined.

Figures 17A, 17B:
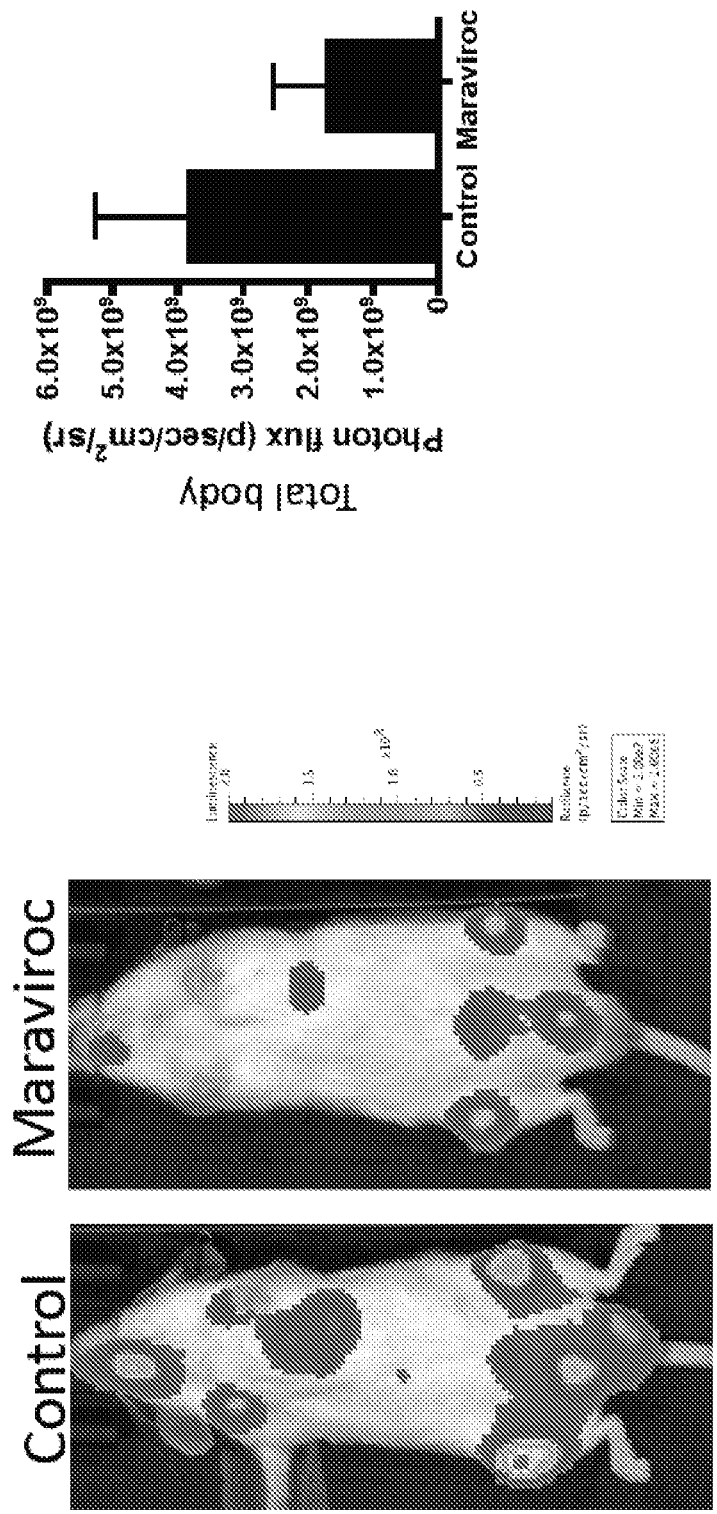
FIG. 17A illustrates representative examples of mice from each group are shown (Mice were treated with oral maraviroc (8 mg/kg) or control)
FIG. 17B illustrates photon flux as a volumetric analysis of total tumor mass.

FIGS. 17A-17D demonstrate that CCR5 antagonists block spinal osteolytic prostate cancer metastasis. PEC lines transduced with vectors expressing the Luc2-Tomato-Red fusion protein were injected into the ventricle of FVB mice and the in vivo bioluminescent signal was quantified after 2 weeks. Mice were treated with oral maraviroc (8 mg/kg) or control. FIG. 17A illustrates representative examples of mice from each group. FIG. 17B illustrates photon flux as a volumetric analysis of total tumor mass and FIG. 17C illustrates lower limb bony mass in the mice. The data shown are mean±SEM for N=8 separate mice in each group, $P<0.05$.

Figure 19A:
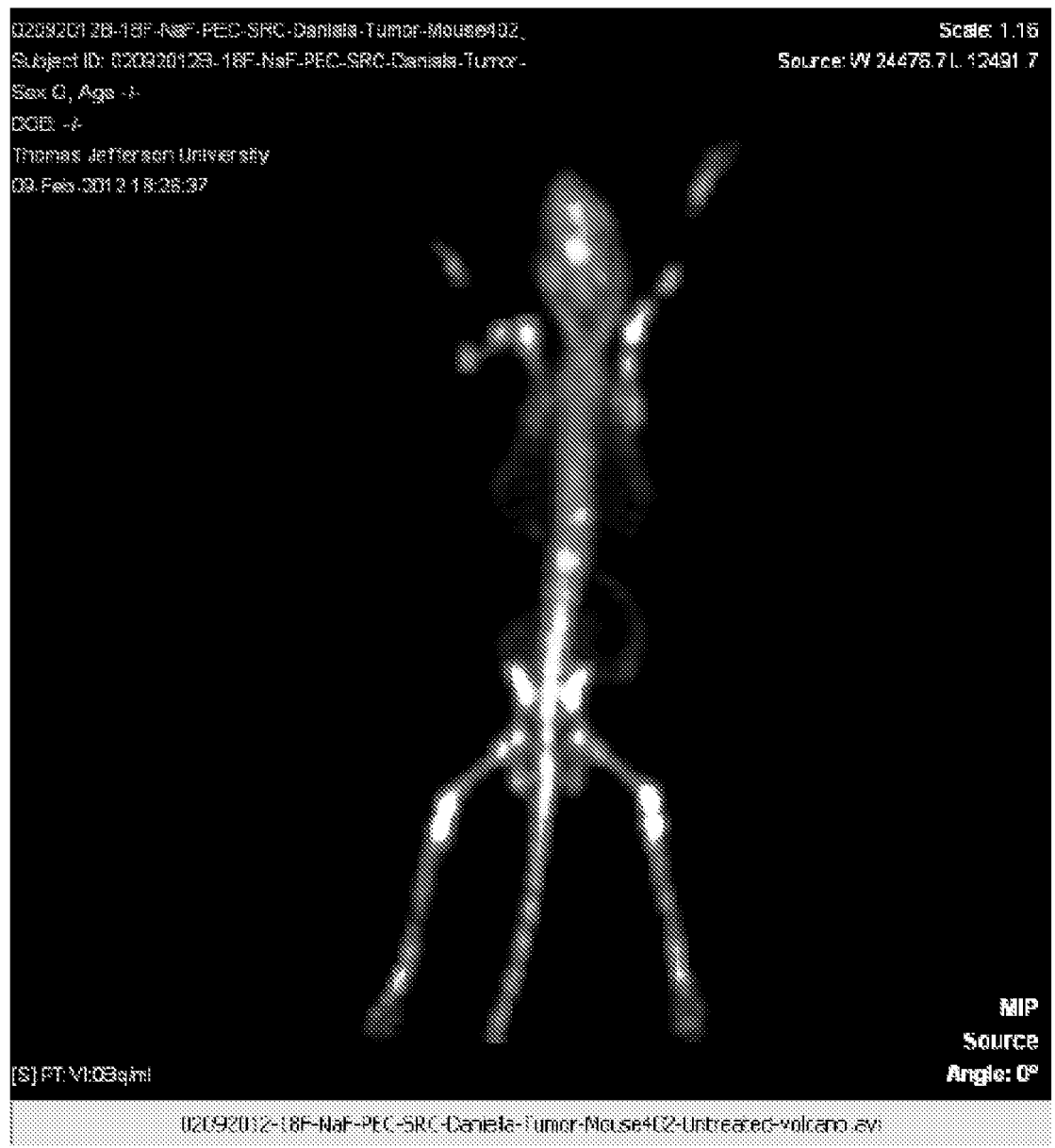
FIGS. 19A and 19B shows daily oral treatment with Maraviroc reduced spine metastasis by >90%.
Figure 19B:
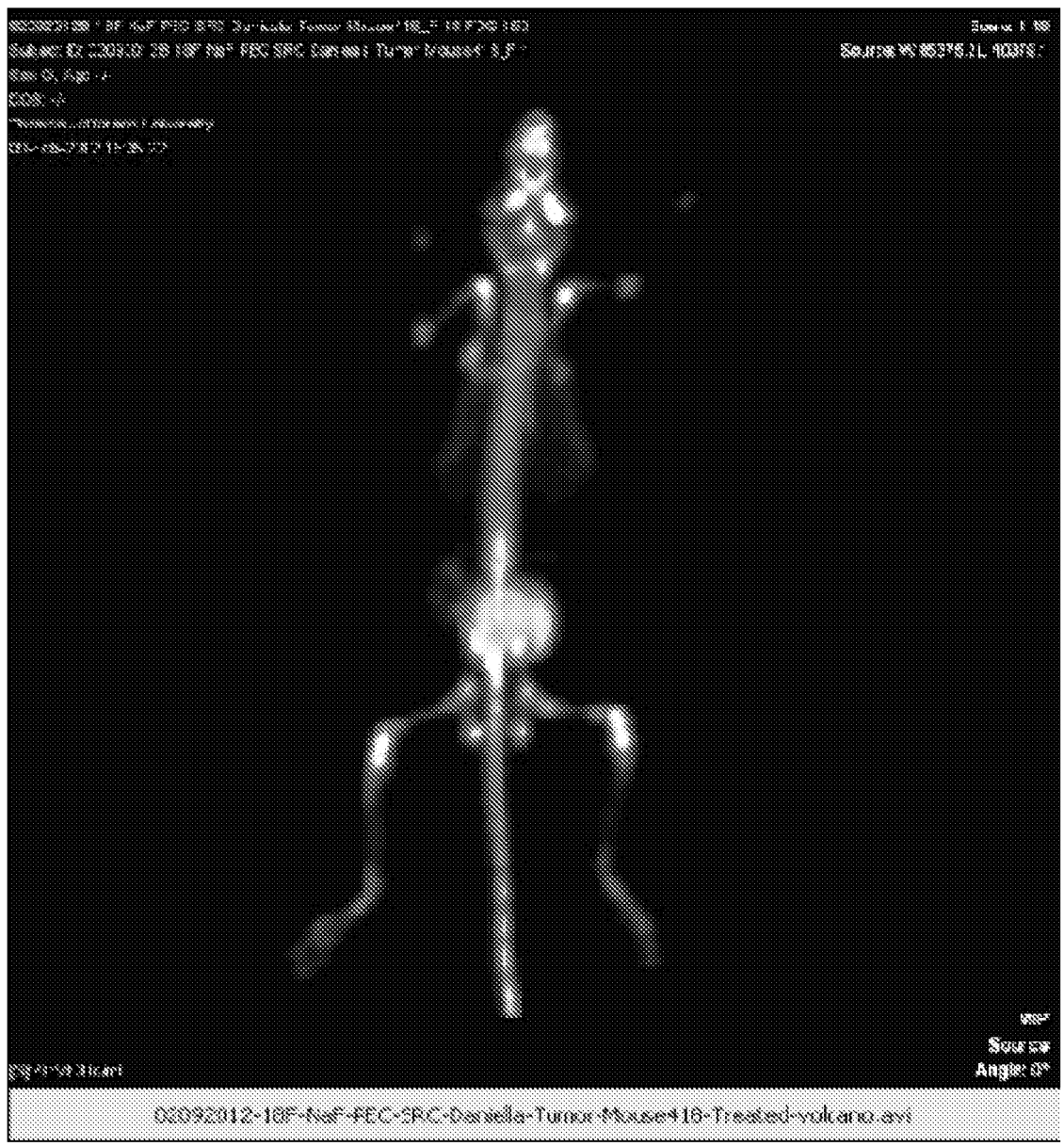

As shown in FIGS. 17A and 17B, the CCR5 antagonist Maraviroc (8 mg/kg oral) reduced total body metastatic burden by >50% and reduced bony metastasis by >50% (see FIGS. 17C and 17D). Further, Flurine-18, Sodium fluoride ("F-18-NaF") imaging correlated with X-ray analysis demonstrated the presence of spine metastasis (FIGS. 18A-18H). Daily oral treatment with Maraviroc reduced spine metastasis by >90% (FIGS. 19A-19B).

REFERENCES

1. Jemal, A., et al., *Cancer statistics*, 2003. CA Cancer J Clin, 2003. 53(1): p. 5-26.
2. Singh, D., et al., *Gene expression correlates of clinical prostate cancer behavior*. Cancer Cell, 2002. 1(2): p. 203-9.
3. Lapointe, J., et al., *Gene expression profiling identifies clinically relevant subtypes of prostate cancer*. Proc Natl Acad Sci USA, 2004. 101(3): p. 811-6.
4. Kattan, M. W., T. M. Wheeler, and P. T. Scardino, *Postoperative nomogram for disease recurrence after radical prostatectomy for prostate cancer*. J Clin Oncol, 1999. 17(5): p. 1499-507.
5. Kattan, M. W., et al., *A preoperative nomogram for disease recurrence following radical prostatectomy for prostate cancer*. J Natl Cancer Inst, 1998. 90(10): p. 766-71.
6. Graefen, M., et al., *Early prostate-specific antigen relapse after radical retropubic prostatectomy: prediction on the basis of preoperative and postoperative tumor characteristics*. Eur Urol, 1999. 36(1): p. 21-30.
7. Dhanasekaran, S. M., et al., *Delineation of prognostic biomarkers in prostate cancer*. Nature, 2001. 412(6849): p. 822-6.
8. Varambally, S., et al., *The polycomb group protein EZH2 is involved in progression of prostate cancer*. Nature, 2002. 419(6907): p. 624-9.

9. Henshall, S. M., et al., *Survival analysis of genome-wide gene expression profiles of prostate cancers identifies new prognostic targets of disease relapse.* Cancer Res, 2003. 63(14): p. 4196-203.
10. LaTulippe, E., et al., *Comprehensive gene expression analysis of prostate cancer reveals distinct transcriptional programs associated with metastatic disease.* Cancer Res, 2002. 62(15): p. 4499-506.
11. Glinsky, G. V., et al., *Gene expression profiling predicts clinical outcome of prostate cancer.* J Clin Invest, 2004. 113(6): p. 913-23.
12. Jenkins, R. B., et al., *Detection of c-Myc oncogene amplification and chromosomal anomlies in metastatic prostatic carcinoma by fluorescence in situ hybridization.* Cancer Res., 1997. 57(3): p. 524-31.
13. Qian, J., R. B. Jenkins, and D. G. Bostwick, *Detection of chromosomal anomalies and c-myc gene amplification in the cribriform pattern of prostatic intraepithelial neoplasia and carcinoma by fluorescence in situ hybridization.* Mod Pathol, 1997. 10(11): p. 1113-9.
14. Ellwood-Yen, K., et al., *Myc-driven murine prostate cancer shares molecular features with human prostate tumors.* Cancer Cell, 2003. 4(3): p. 223-38.
15. Creighton, C. J., *Multiple oncogenic pathway signatures show coordinate expression patterns in human prostate tumors.* PLoS One, 2008. 3(3): p. e1816.
16. Gumerlock, P. H., et al., *Activated ras alleles in human carcinoma of the prostate are rare.* Cancer Res, 1991. 51(6): p. 1632-7.
17. Carter, B. S., J. I. Epstein, and W. B. Isaacs, *ras gene mutations in human prostate cancer.* Cancer Res, 1990. 50(21): p. 6830-2.
18. Uzgare, A. R., P. J. Kaplan, and N. M. Greenberg, *Differential expression and/or activation of P38MAPK, erk1/2, and jnk during the initiation and progression of prostate cancer.* Prostate, 2003. 55(2): p. 128-39.
19. Le Page, C., et al., *Expression and localisation of Akt-1, Akt-2 and Akt-3 correlate with clinical outcome of prostate cancer patients.* Br J Cancer, 2006. 94(12): p. 1906-12.
20. Taylor, B. S., et al., *Integrative genomic profiling of human prostate cancer.* Cancer Cell, 2010. 18(1): p. 11-22.
21. Weber, M. J. and D. Gioeli, *Ras signaling in prostate cancer progression.* J Cell Biochem, 2004. 91(1): p. 13-25.
22. Ware, J. L., et al., *Differential reactivity with anti-c-erbB-2 antiserum among human malignant and benighn prostatic tissue [abstract].* Proc Am Assoc Cancer Res, 1989. 30: p. 1737.
23. Hughes, C., et al., *Molecular pathology of prostate cancer.* J Clin Pathol, 2005. 58(7): p. 673-84.
24. Paronetto, M. P., et al., *Expression of a truncated form of the c-Kit tyrosine kinase receptor and activation of Src kinase in human prostatic cancer.* Am J Pathol, 2004. 164(4): p. 1243-51.
25. Bull, J. H., et al., *Identification of potential diagnostic markers of prostate cancer and prostatic intraepithelial neoplasia using cDNA microarray.* Br J Cancer, 2001. 84(11): p. 1512-9.
26. Cohen, S, and B. S. Rabin, *Psychologic stress, immunity, and cancer.* J Natl Cancer Inst, 1998. 90(1): p. 3-4.
27. Lawson, D. A., et al., *Isolation and functional characterization of murine prostate stem cells.* Proc Natl Acad Sci USA, 2007. 104(1): p. 181-6.
28. Huang, E. S., et al., *Gene expression phenotypes of oncogenic signaling pathways.* Cell Cycle, 2003. 2(5): p. 415-7.
29. Catalona, W. J., et al., *Selection of optimal prostate specific antigen cutoffs for early detection of prostate cancer: receiver operating characteristic curves.* J Urol, 1994. 152(6 Pt 1): p. 2037-42.
30. Thompson, I. M., et al., *Effect of finasteride on the sensitivity of PSA for detecting prostate cancer.* J Natl Cancer Inst, 2006. 98(16): p. 1128-33.
31. Akimoto, S., et al., *Relationship between prostate-specific antigen, clinical stage, and degree of bone metastasis in patients with prostate cancer: comparison with prostatic acid phosphatase and alkaline phosphatase.* Int J Urol, 1997. 4(6): p. 572-5.
32. Hanley, J. A. and B. J. McNeil, *The meaning and use of the area under a receiver operating characteristic (ROC) curve.* Radiology, 1982. 143(1): p. 29-36.
33. Sharma, A., et al., *Novel functions of the retinoblastoma tumor suppressor in controlling lethal tumor phenotypes. (In Press).* J Clin Invest, 2010: p. (In Press).
34. Neve, R. M., et al., *A collection of breast cancer cell lines for the study of functionally distinct cancer subtypes.* Cancer Cell, 2006. 10(6): p. 515-27.
35. Chin, K., et al., *Genomic and transcriptional aberrations linked to breast cancer pathophysiologies.* Cancer Cell, 2006. 10(6): p. 529-41.
36. Welsh, J. B., et al., *Analysis of gene expression identifies candidate markers and pharmacological targets in prostate cancer.* Cancer Res, 2001. 61(16): p. 5974-8.
37. Mori, S., et al., *Utilization of genomic signatures to identify phenotype-specific drugs.* PLoS One, 2009. 4(8): p. e6772.
38. Sato, K., et al., *Clinical significance of alterations of chromosome 8 in high-grade, advanced, nonmetastatic prostate carcinoma.* J Natl Cancer Inst, 1999. 91(18): p. 1574-80.
39. Casimiro, M., et al., *ErbB-2 induces the cyclin D1 gene in prostate epithelial cells in vitro and in vivo.* Cancer Res, 2007. 67(9): p. 4364-72.
40. Gioeli, D., S. Kraus, and M. J. Weber, *Signal Transduction by the Ras-MAP Kinase Pathway in Prostate Cancer Progression, in Prostate cancer: signaling networks, genetics, and new treatment strategies,* R. G. Pestell and M. T. Nevalainen, Editors. 2008, Humana Press: Totowa, N.J. p. 223-256.
41. Scherl, A., et al., *Prostatic intraepithelial neoplasia and intestinal metaplasia in prostates of probasin-RAS transgenic mice.* Prostate, 2004. 59(4): p. 448-59.
42. Ilio, K. Y., et al., *The primary culture of rat prostate basal cells.* J Androl, 1998. 19(6): p. 718-24.
43. Li, Z., et al., *Cyclin D1 regulates cellular migration through the inhibition of thrombospondin 1 and ROCK signaling.* Mol Cell Biol, 2006. 26(11): p. 4240-56.
44. Liu, M., et al., *p21CIP1 attenuates Ras-and c-Myc-dependent breast tumor epithelial mesenchymal transition and cancer stem cell-like gene expression in vivo.* Proc Natl Acad Sci USA, 2009. 106(45): p. 19035-9.
45. Irizarry, R. A., et al., *Summaries of Affymetrix GeneChip probe level data.* Nucleic Acids Res, 2003. 31(4): p. e15.
46. Huang, E., et al., *Gene expression phenotypic models that predict the activity of oncogenic pathways.* Nat Genet, 2003. 34(2): p. 226-230.
47. Dai, M., et al., *Evolving gene/transcript definitions significantly alter the interpretation of GeneChip data.* Nucleic Acids Res, 2005. 33(20): p. e175.

48. Chen, R., L. Li, and A. J. Butte, *AILUN: reannotating gene expression data automatically*. Nat Methods, 2007. 4(11): p. 879.

What is claimed is:

1. A method of inhibiting spinal metastatic lesions and total body metastatic burden from prostate cancer in an immunocompetent subject at risk for developing metastatic lesions from the prostate cancer, the method comprising:
    administering maraviroc daily to said immunocompetent subject at risk for developing metastatic lesions, thereby inhibiting spinal metastatic lesions by at least 90% and reducing total body metastatic burden by at least 50% as compared to a subject at risk for developing metastatic lesions that is not administered maraviroc.

2. The method of claim 1, wherein the maraviroc inhibits spinal metastatic lesions and metastatic lesions in one or more organs selected from the group consisting of liver, brain, bladder, lung, adrenal gland, kidney and combinations thereof.

3. The method of claim 1, further comprising determining whether the immunocompetent subject is at risk for developing spinal metastatic lesions from the cancer before the administration of the maraviroc, the determining step comprising:
    a) measuring a level of expression of CCR5 in a prostate tumor sample obtained from the subject;
    b) comparing the expression level of CCR5 in the prostate tumor sample with an expression level of CCR5 in a control sample;
    wherein the subject is determined to be at risk for developing spinal metastatic lesions from prostate cancer if the expression level of CCR5 in the prostate tumor sample is elevated compared to the expression level of CCR5 in the control sample.

4. A method of inhibiting spinal metastatic lesions and total body metastatic burden from prostate cancer in an immunocompetent subject having non-metastatic prostate cancer, the method comprising:
    administering to the immunocompetent subject a therapeutically effective amount of maraviroc daily to inhibit spinal metastatic lesions from the prostate cancer, thereby inhibiting spinal metastatic lesions by at least 90% and reducing total body metastatic burden by at least 50% as compared to a subject having non-metastatic prostate cancer that is not administered maraviroc.

5. The method of claim 4, wherein administering a therapeutically effective amount of maraviroc daily inhibits spinal metastatic lesions and metastatic lesions in one or more organs selected from the group consisting of liver, brain, bladder, lung, adrenal gland, and kidney.

6. The method of claim 1, wherein the immunocompetent subject is a human.

7. The method of claim 4, wherein the immunocompetent subject is a human.

* * * * *

UNITED STATES PATENT AND TRADEMARK OFFICE
CERTIFICATE OF CORRECTION

PATENT NO. : 10,952,415 B2
APPLICATION NO. : 14/003384
DATED : March 23, 2021
INVENTOR(S) : Richard G. Pestell Page 1 of 1

It is certified that error appears in the above-identified patent and that said Letters Patent is hereby corrected as shown below:

In the Specification

Column 1, Line 15, please replace the entirety of the GOVERNMENT LICENSE RIGHTS paragraph with the following: "This invention was made with government support under Grant Numbers CA70896, CA75503, CA86072, CA56036, and CA132115 awarded by the National Institutes of Health. The government has certain rights in the invention."

Signed and Sealed this
Twenty-seventh Day of August, 2024

Katherine Kelly Vidal
*Director of the United States Patent and Trademark Office*